US012698534B2

(12) United States Patent (10) Patent No.: US 12,698,534 B2

Ramos et al. (45) Date of Patent: Aug. 4, 2026

(54) SYSTEMS AND METHODS FOR CHARACTERIZING AND TREATING DISEASE

(71) Applicant: Arizona Board of Regents on Behalf of the University of Arizona, Tucson, AZ (US)

(72) Inventors: Kenneth Ramos, Tucson, AZ (US); Emma Bowers, Tucson, AZ (US); Patrick Silva, Tucson, AZ (US); Brian McKay, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 927 days.

(21) Appl. No.: 17/420,602

(22) PCT Filed: Dec. 30, 2019

(86) PCT No.: PCT/US2019/068952

§ 371 (c)(1),
(2) Date: Jul. 2, 2021

(87) PCT Pub. No.: WO2020/143436

PCT Pub. Date: Jul. 9, 2020

(65) Prior Publication Data

US 2022/0081726 A1 Mar. 17, 2022

Related U.S. Application Data

(60) Provisional application No. 62/787,444, filed on Jan. 2, 2019.

(51) Int. Cl.
*C12Q 1/6886* (2018.01)

(52) U.S. Cl.
CPC ..... *C12Q 1/6886* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 5,225,326 A | 7/1993 | Bresser et al. | |
| 5,545,524 A | 8/1996 | Trent et al. | |
| 6,121,489 A | 9/2000 | Dorner et al. | |
| 6,573,043 B1 | 6/2003 | Cohen et al. | |
| 8,658,396 B2 | 2/2014 | Turner et al. | |
| 2012/0309018 A1 | 12/2012 | Skolnick et al. | |
| 2014/0031250 A1* | 1/2014 | Ting | C12Q 1/6886 |
| | | | 435/6.12 |
| 2017/0356054 A1 | 12/2017 | Ting et al. | |

FOREIGN PATENT DOCUMENTS

| | | |
|---|---|---|
| WO | WO 2014/160032 | 10/2014 |
| WO | WO 2017/172839 | 10/2017 |

OTHER PUBLICATIONS

Bowers et al. 58th Annual Meeting. Society of Toxicology Annual Meeting. Poster #1465, poster presented Mar. 11, 2019, published Jan. 28, 2019, available via URL: <discovery.northernlight.com/document.php?datasource=PHE&docid=PE20190308350000050&context=proquest%40northernlight.com> (Year: 2019).*
Sauter, E.R. Transl Cancer Research. 2017. 6 (Sppl 8), S1316-S1320 (Year: 2017).*
Castellanos-Rizaldos et al. Clin Cancer Res. p. 1-7 (Year: 2018).*
Kalluri, R. J Clin Invest. 126(4): 1208-1215 (Year: 2016).*
International Search Report and Written Opinion for PCT/US19/68952. Mailed May 15, 2020. 17 pages.
Abdelmohsen et al., RNA-binding protein nucleolin in disease. RNA Biol. Jun. 2012;9(6):799-808.
Agassandian et al., VCAM-1 is a TGF-β1 inducible gene upregulated in idiopathic pulmonary fibrosis. Cell Signal. Dec. 2015;27(12):2467-73.
An et al., Active retrotransposition by a synthetic L1 element in mice. Proc Natl Acad Sci U S A. Dec. 5, 2006;103(49):18662-7.
Arif et al., 32P-Postlabeling analysis of lipophilic DNA adducts resulting from interaction with (+/−)-3-hydroxy-trans-7,8-dihydroxy-9,10-epoxy-7,8,9,10-tetrahydrobenzo [a]pyrene. Chem Biol Interact. Apr. 1, 1999;118(2):87-97.
Awan et al., Identification of Circulating Biomarker Candidates for Hepatocellular Carcinoma (HCC): An Integrated Prioritization Approach. PLoS One. Sep. 28, 2015;10(9):e0138913. 26 pages.
Badge et al., ATLAS: a system to selectively identify human-specific L1 insertions. Am J Hum Genet. Apr. 2003;72(4):823-38.
Baik et al., Estrogen signaling in lung cancer: an opportunity for novel therapy. Cancers (Basel). Sep. 25, 2012;4(4):969-88.
Balaj et al., Tumour microvesicles contain retrotransposon elements and amplified oncogene sequences. Nat Commun. Feb. 1, 2011;2:180. 1-9.
Banasiwicz et al., Identification and quantitation of benzo[a]pyrene-derived DNA adducts formed at low adduction level in mice lung tissue. Anal Biochem. Nov. 15, 2004;334(2):390-400.
Barchitta et al., LINE-1 hypomethylation in blood and tissue samples as an epigenetic marker for cancer risk: a systematic review and meta-analysis. PLoS One. Oct. 2, 2014;9(10):e109478. 1-18.
Bates et al., G-quadruplex oligonucleotide AS1411 as a cancer-targeting agent: Uses and mechanisms. Biochim Biophys Acta Gen Subj. May 2017;1861(5 Pt B):1414-1428.
Bates et al., G-rich oligonucleotides for cancer treatment. Methods Mol Biol. 2009;542:379-92.

(Continued)

*Primary Examiner* — Carla J Myers
(74) *Attorney, Agent, or Firm* — Casimir Jones, S.C.; Robert A. Goetz

(57) ABSTRACT

Provided herein are composition and methods for characterizing and treating disease. In particular, provided herein are compositions and methods for characterizing and treating disease (e.g., cancer) associated with activation of LINE-1 retroelements.

4 Claims, 22 Drawing Sheets

Specification includes a Sequence Listing.

(56)                    References Cited

OTHER PUBLICATIONS

Beck et al., LINE-1 elements in structural variation and disease. Annu Rev Genomics Hum Genet. 2011;12:187-215.

Beck et al., LINE-1 retrotransposition activity in human genomes. Cell. Jun. 25, 2010;141(7):1159-70.

Belancio et al., The impact of multiple splice sites in human L1 elements. Gene. Mar. 31, 2008;411(1-2):38-45.

Benedetti et al., Nucleolin antagonist triggers autophagic cell death in human glioblastoma primary cells and decreased in vivo tumor growth in orthotopic brain tumor model. Oncotarget. Dec. 8, 2015;6(39):42091-104.

Berger et al., The roles of nucleolin subcellular localization in cancer. Biochimie. Jun. 2015;113:78-85.

Birmpas et al., Nucleolin mediates the antiangiogenesis effect of the pseudopeptide N6L. BMC Cell Biol. Nov. 13, 2012;13:32. 10 pages.

Bodak et al., Regulation of LINE-1 in mammals. Biomol Concepts. Oct. 2014;5(5):409-28.

Bojang et al., Epigenetic reactivation of LINE-1 retrotransposon disrupts NuRD corepressor functions and induces oncogenic transformation in human bronchial epithelial cells. Mol Oncol. Aug. 2018;12(8):1342-1357.

Bojang et al., Reprogramming of the HepG2 genome by long interspersed nuclear element-1. Mol Oncol. Aug. 2013;7(4):812-25.

Branton et al., The potential and challenges of nanopore sequencing. Nat Biotechnol. Oct. 2008;26(10):1146-53.

Brockstedt et al., Identification of apoptosis-associated proteins in a human Burkitt lymphoma cell line. Cleavage of heterogeneous nuclear ribonucleoprotein A1 by caspase 3. J Biol Chem. Oct. 23, 1998;273(43):28057-64.

Brouha et al., Hot L1s account for the bulk of retrotransposition in the human population. Proc Natl Acad Sci U S A. Apr. 29, 2003;100(9):5280-5.

Bruno et al., Lung cell-specific expression of the murine surfactant protein A (Sp-A) gene is mediated by interactions between the SP-A promoter and thyroid transcription factor-1. J Biol Chem. Mar. 24, 1995;270(12):6531-6.

Burger et al., Epidemiology and risk factors of urothelial bladder cancer. Eur Urol. Feb. 2013;63(2):234-41.

Carlson et al., Insertional mutagenesis in mice: new perspectives and tools. Nat Rev Genet. Jul. 2005;6(7):568-80.

Chalfin et al., Nucleolin Staining May Aid in the Identification of Circulating Prostate Cancer Cells. Clin Genitourin Cancer. Jun. 2017;15(3):e477-e481. 5 pages.

Chen et al., Prognostic value of LINE-1 retrotransposon expression and its subcellular localization in breast cancer. Breast Cancer Res Treat. Nov. 2012;136(1):129-42.

Cheung et al., Integration of cytogenetic landmarks into the draft sequence of the human genome. Nature. Feb. 15, 2001;409(6822):953-8.

Clayton et al., Patterns of Transposable Element Expression and Insertion in Cancer. Front Mol Biosci. Nov. 16, 2016;3:76. 11 pages.

Conigliaro et al., CD90+ liver cancer cells modulate endothelial cell phenotype through the release of exosomes containing H19 lncRNA. Mol Cancer. Aug. 14, 2015;14:155. 11 pages.

Cordaux et al., The impact of retrotransposons on human genome evolution. Nat Rev Genet. Oct. 2009;10(10):691-703.

Coulton et al., In Situ Hybridization: Medical Applications. Kluwer Academic Publishers, Boston. 1992. TOC only. 4 pages.

De Cola et al., N6L pseudopeptide interferes with nucleophosmin protein-protein interactions and sensitizes leukemic cells to chemotherapy. Cancer Lett. Jan. 1, 2018;412:272-282.

De Koning et al., Repetitive elements may comprise over two-thirds of the human genome. PLoS Genet. Dec. 2011;7(12):e1002384. 12 pages.

De Luca et al., Enhanced expression of LINE-1-encoded ORF2 protein in early stages of colon and prostate transformation. Oncotarget. Jan. 26, 2016;7(4):4048-61.

Deroo et al., Global DNA methylation and one-carbon metabolism gene polymorphisms and the risk of breast cancer in the Sister Study. Carcinogenesis. Feb. 2014;35(2):333-8.

Destouches et al., A simple approach to cancer therapy afforded by multivalent pseudopeptides that target cell-surface nucleoproteins. Cancer Res. May 1, 2011;71(9):3296-305.

Destouches et al., Multivalent pseudopeptides targeting cell surface nucleoproteins inhibit cancer cell invasion through tissue inhibitor of metalloproteinases 3 (TIMP-3) release. J Biol Chem. Dec. 21, 2012;287(52):43685-93.

Dhez et al., Targeted therapy of human glioblastoma via delivery of a toxin through a peptide directed to cell surface nucleolin. J Cell Physiol. May 2018;233(5):4091-4105.

Diamantopoulou et al., Multivalent cationic pseudopeptide polyplexes as a tool for cancer therapy. Oncotarget. Sep. 30, 2017;8(52):90108-90122.

Dombroski et al., Isolation of an active human transposable element. Science. Dec. 20, 1991;254(5039):1805-8.

Drmanac et al., Accurate sequencing by hybridization for DNA diagnostics and individual genomics. Nat Biotechnol. Jan. 1998;16(1):54-8.

Du et al., Receptor-type protein tyrosine phosphatases in cancer. Chin J Cancer. Feb. 2015;34(2):61-9.

Dupuy et al., Transposition and gene disruption in the male germline of the mouse. Genesis. Jun. 2001;30(2):82-8.

Dutta et al., Men and mice: Relating their ages. Life Sci. May 1, 2016;152:244-8.

Eberwine et al., In Situ Hybridization: In Neurobiology; Advances in Methodology, Oxford University Press Inc., England. 1994. TOC only. 4 pages.

Eid et al., Real-time DNA sequencing from single polymerase molecules. Science. Jan. 2, 2009;323(5910):133-8.

Fadloun et al., Chromatin signatures and retrotransposon profiling in mouse embryos reveal regulation of LINE-1 by RNA. Nat Struct Mol Biol. Mar. 2013;20(3):332-8.

Farazi et al., Hepatocellular carcinoma pathogenesis: from genes to environment. Nat Rev Cancer. Sep. 2006;6(9):674-87.

Faulkner et al., The regulated retrotransposon transcriptome of mammalian cells. Nat Genet. May 2009;41(5):563-71.

Feitelson et al., Genetic mechanisms of hepatocarcinogenesis. Oncogene. Apr. 11, 2002;21(16):2593-604.

Feng et al., Human L1 retrotransposon encodes a conserved endonuclease required for retrotransposition. Cell. Nov. 29, 1996;87(5):905-16.

Gasior et al., The human LINE-1 retrotransposon creates DNA double-strand breaks. J Mol Biol. Apr. 14, 2006;357(5):1383-93.

Gelboin et al., Benzo[alpha]pyrene metabolism, activation and carcinogenesis: role and regulation of mixed-function oxidases and related enzymes. Physiol Rev. Oct. 1980;60(4):1107-66.

Gilles et al., Nucleolin Targeting Impairs the Progression of Pancreatic Cancer and Promotes the Normalization of Tumor Vasculature. Cancer Res. Dec. 15, 2016;76(24):7181-7193.

Ginsberg et al., DNA adduct formation in mouse tissues in relation to serum levels of benzo(a)pyrene-diol-epoxide after injection of benzo(a)pyrene or the diol-epoxide. Cancer Res. Feb. 15, 1990;50(4):1189-94.

Grimaldi et al., Members of the Kpnl family of long interspersed repeated sequences join and interrupt alpha-satellite in the monkey genome. Nucleic Acids Res. Jan. 25, 1983;11(2):321-38.

Guerra et al., Morbidity and mortality associated with the restrictive spirometric pattern: a longitudinal study. Thorax. Jun. 2010; 65(6):499-504.

György et al., Membrane vesicles, current state-of-the-art: emerging role of extracellular vesicles. Cell Mol Life Sci. Aug. 2011;68(16):2667-88.

Hammoudi et al., Proteomic profiling of a mouse model of acute intestinal Apc deletion leads to identification of potential novel biomarkers of human colorectal cancer (CRC). Biochem Biophys Res Commun. Oct. 25, 2013;440(3):364-70.

Han et al., A highly active synthetic mammalian retrotransposon. Nature. May 20, 2004;429(6989):314-8.

(56)             References Cited

OTHER PUBLICATIONS

Hao et al., Correlation of telomere length shortening with TP53 somatic mutations, polymorphisms and allelic loss in breast tumors and esophageal cancer. Oncol Rep. Jan. 2013;29(1):226-36.

Harris et al., Single-molecule DNA sequencing of a viral genome. Science. Apr. 4, 2008;320(5872):106-9.

Haugen. Women who smoke: are women more susceptible to tobacco-induced lung cancer? Carcinogenesis. Feb. 2002;23(2):227-9.

He et al., Integrated immunoisolation and protein analysis of circulating exosomes using microfluidic technology. Lab Chip. Oct. 7, 2014;14(19):3773-80.

Henschke et al., Women's susceptibility to tobacco carcinogens. Lung Cancer. Jan. 2004;43(1):1-5.

Hogg. Why does airway inflammation persist after the smoking stops? Thorax. Feb. 2006;61(2):96-7.

Holmes et al., Studies on p40, the leucine zipper motif-containing protein encoded by the first open reading frame of an active human LINE-1 transposable element. J Biol Chem. Oct. 5, 1992;267(28):19765-8.

Hornef et al., DNAH5 mutations are a common cause of primary ciliary dyskinesia with outer dynein arm defects. Am J Respir Crit Care Med. Jul. 15, 2006;174(2):120-6.

Hsu et al., Estrogen, Estrogen Receptor and Lung Cancer. Int J Mol Sci. Aug. 5, 2017;18(8):1713. 17 pages.

Hussain et al., TP53 mutations and hepatocellular carcinoma: insights into the etiology and pathogenesis of liver cancer. Oncogene. Apr. 2, 2007;26(15):2166-76.

Ikuta et al., Zinc finger transcription factor Slug is a novel target gene of aryl hydrocarbon receptor. Exp Cell Res. Nov. 1, 2006;312(18):3585-94.

Imperatori et al., LINE-1 hypomethylation is associated to specific clinico-pathological features in Stage I non-small cell lung cancer. Lung Cancer. Jun. 2017;108:83-89.

Iskow et al., Natural mutagenesis of human genomes by endogenous retrotransposons. Cell. Jun. 25, 2010;141(7):1253-61.

Jachowicz et al., LINE-1 activation after fertilization regulates global chromatin accessibility in the early mouse embryo. Nat Genet. Oct. 2017;49(10):1502-1510.

Jain et al., Targeting nucleolin for better survival in diffuse large B-cell lymphoma. Leukemia. Mar. 2018;32(3):663-674.

Jakobsen et al., Exosomal proteins as potential diagnostic markers in advanced non-small cell lung carcinoma. J Extracell Vesicles. Mar. 2, 2015;4:26659. 10 pages.

Jia et al., New perspectives of physiological and pathological functions of nucleolin (NCL). Life Sci. Oct. 1, 2017;186:1-10.

Jonna et al., Molecular diagnostics and targeted therapies in non-small cell lung cancer (NSCLC): an update. Discov Med. Mar. 2019;27(148):167-170.

Jordan et al., Origin of a substantial fraction of human regulatory sequences from transposable elements. Trends Genet. Feb. 2003;19(2):68-72.

Jurka. Repeats in genomic DNA: mining and meaning. Curr Opin Struct Biol. Jun. 1998;8(3):333-7.

Kabirian-Dehkordi et al., AS1411-conjugated gold nanoparticles affect cell proliferation through a mechanism that seems independent of nucleolin. Nanomedicine. Oct. 2019;21:102060. 11 pages.

Kang et al., Quercetin inhibits benzo[a]pyrene-induced DNA adducts in human Hep G2 cells by altering cytochrome P-450 1A1 gene expression. Nutr Cancer. 1999;35(2):175-9.

Kapitulnik et al., Tumorigenicity studies with diol-epoxides of benzo(a)pyrene which indicate that (+/−)-trans-7beta, 8alpha-dihydroxy-9alpha, 10alpha-epoxy-7,8,9,10-tetrahydrobenzo(a)pyrene is an ultimate carcinogen in newborn mice. Cancer Res. Feb. 1978;38(2):354-8.

Kasala et al., Benzo(a)pyrene induced lung cancer: Role of dietary phytochemicals in chemoprevention. Pharmacol Rep. Oct. 2015;67(5):996-1009.

Kato. Impact of the next generation DNA sequencers. Int J Clin Exp Med. Jul. 8, 2009;2(2):193-202.

Kazazian et al., Haemophilia A resulting from de novo insertion of L1 sequences represents a novel mechanism for mutation in man. Nature. Mar. 10, 1988;332(6160):164-6.

Khalid et al., Line-1: Implications in the etiology of cancer, clinical applications, and pharmacologic targets. Mutat Res Rev Mutat Res. Oct.-Dec. 2018;778:51-60.

Klinger et al., Rapid detection of chromosome aneuploidies in uncultured amniocytes by using fluorescence in situ hybridization (FISH). Am J Hum Genet. Jul. 1992;51(1):55-65.

Knudson et al., Changes in the normal maximal expiratory flow-volume curve with growth and aging. Am Rev Respir Dis. Jun. 1983;127(6):725-34.

Knudson et al., The maximal expiratory flow-volume curve. Normal standards, variability, and effects of age. Am Rev Respir Dis. May 1976;113(5):587-600.

Kogure et al., Intercellular nanovesicle-mediated microRNA transfer: a mechanism of environmental modulation of hepatocellular cancer cell growth. Hepatology. Oct. 2011;54(4):1237-48.

Kondo et al., Genetic instability and aberrant DNA methylation in chronic hepatitis and cirrhosis—A comprehensive study of loss of heterozygosity and microsatellite instability at 39 loci and DNA hypermethylation on 8 CpG islands in microdissected specimens from patients with hepatocellular carcinoma. Hepatology. Nov. 2000;32(5):970-9.

Korlach et al., Selective aluminum passivation for targeted immobilization of single DNA polymerase molecules in zero-mode waveguide nanostructures. Proc Natl Acad Sci U S A. Jan. 29, 2008;105(4):1176-81.

Kuo et al., Detection of aneuploidy involving chromosomes 13, 18, or 21, by fluorescence in situ hybridization (FISH) to interphase and metaphase amniocytes. Am J Hum Genet. Jul. 1991;49(1):112-9.

Lander et al., Initial sequencing and analysis of the human genome. Nature. Feb. 15, 2001;409(6822):860-921.

Lange et al., Alu and LINE-1 methylation and lung function in the normative ageing study. BMJ Open 2012; 2: e00123. 7 pages.

Lebowitz et al., Tucson epidemiologic study of obstructive lung diseases. I: Methodology and prevalence of disease. Am J Epidemiol. Aug. 1975;102(2):137-52.

Levene et al., Zero-mode waveguides for single-molecule analysis at high concentrations. Science. Jan. 31, 2003;299(5607):682-6.

Li et al., TGFβ1 in fibroblasts-derived exosomes promotes epithelial- mesenchymal transition of ovarian cancer cells. Oncotarget. Oct. 6, 2017;8(56):96035-96047.

Lin et al., Association of aryl hydrocarbon receptor and cytochrome P4501B1 expressions in human non-small cell lung cancers. Lung Cancer. Dec. 2003;42(3):255-61.

Lin et al., DNA methylation markers of surfactant proteins in lung cancer. Int J Oncol. 2007, vol. 31, No. 1 pp. 181-191.

Liu et al., The CC Chemokine Ligand 2 (CCL2) Mediates Fibroblast Survival through IL-6. Am J Resp Cell Mol Biol 2007; 37, 121-128.

Lu et al., Identification of genes differentially expressed in vascular smooth muscle cells following benzo[a]pyrene challenge: implications for chemical atherogenesis. Biochem Biophys Res Commun. Dec. 30, 1998;253(3):828-33.

Lu et al., Redox regulation of a novel L1Md-A2 retrotransposon in vascular smooth muscle cells. J Biol Chem. Jul. 25, 2003;278(30):28201-9.

Maclean et al., Application of 'next-generation' sApplication of 'next-generation' sequencing technologies to microbial genetics. Nat Rev Microbiol. Apr. 2009;7(4):287-96.

Margulies et al., Genome sequencing in microfabricated high-density picolitre reactors. Nature. Sep. 15, 2005;437(7057):376-80.

Masyuk et al., Exosomes in the pathogenesis, diagnostics and therapeutics of liver diseases. J Hepatol. Sep. 2013;59(3):621-5.

Mathias et al., Reverse transcriptase encoded by a human transposable element. Science. Dec. 20, 1991;254(5039):1808-10.

Maxam et al., A new method for sequencing DNA. Proc Natl Acad Sci USA. Feb. 1977;74(2):560-4.

Meyer et al., Characterization of the AhR-hsp90-XAP2 core complex and the role of the immunophilin-related protein XAP2 in AhR stabilization. Biochemistry. Jul. 13, 1999;38(28):8907-17.

(56)                    References Cited

OTHER PUBLICATIONS

Milara et al., Cigarette smoke exposure up-regulates endothelin receptor B in human pulmonary artery endothelial cells: molecular and functional consequences. Br J Pharmacol. Dec. 2010;161(7):1599-615.

Miller et al., Persistent airway inflammation and emphysema progression on CT scan in ex-smokers observed for 4 years. Chest. Jun. 2011;139(6):1380-1387.

Mollerup et al., Sex differences in risk of lung cancer: Expression of genes in the PAH bioactivation pathway in relation to smoking and bulky DNA adducts. Int J Cancer. Aug. 15, 2006;119(4):741-4.

Montoya-Durango et al., Epigenetic control of mammalian LINE-1 retrotransposon by retinoblastoma proteins. Mutat Res. Jun. 1, 2009;665(1-2):20-8.

Montoya-Durango et al., L1 retrotransposon and retinoblastoma: molecular linkages between epigenetics and cancer. Curr Mol Med. Jul. 2010;10(5):511-21.

Montoya-Durango et al., LINE-1 silencing by retinoblastoma proteins is effected through the nucleosomal and remodeling deacetylase multiprotein complex. BMC Cancer. Jan. 25, 2016;16:38. 8 pages.

Moon et al., CCN1 secretion and cleavage regulate the lung epithelial cell functions after cigarette smoke. Am J Physiol Lung Cell Mol Physiol. Aug. 15, 2014;307(4):L326-37.

Moorthy et al., Pentachlorophenol enhances 9-hydroxybenzo [a] pyrene-induced hepatic DNA adduct formation in vivo and inhibits microsomal epoxide hydrolase and glutathione S-transferase activities in vitro: likely inhibition of epoxide detoxication by pentachlorophenol. Arch Toxicol. 1996;70(11):696-703.

Moorthy et al., Polycyclic aromatic hydrocarbons: from metabolism to lung cancer. Toxicol Sci. May 2015;145(1):5-15.

Moran et al., Exon shuffling by L1 retrotransposition. Science. Mar. 5, 1999;283(5407):1530-4.

Moran et al., High frequency retrotransposition in cultured mammalian cells. Cell. Nov. 29, 1996;87(5):917-27.

Naufer et al., Protein-nucleic acid interactions of LINE-1 ORF1p. Semin Cell Dev Biol. Feb. 2019; 86: 140-149.

Nebert et al., Analysis of the glutathione S-transferase (GST) gene family. Hum Genomics. Nov. 2004;1(6):460-4.

Ostertag et al., Biology of mammalian L1 retrotransposons. Annu Rev Genet. 2001;35:501-38.

Papasotiriou et al., L1 retrotransposon expression in circulating tumor cells. PLoS One. Feb. 6, 2017;12(2):e0171466. 8 pages.

Patchsung et al., Long interspersed nuclear element-1 hypomethylation and oxidative stress: correlation and bladder cancer diagnostic potential. PLoS One. 2012;7(5):e37009. 9 pages.

Pauler et al., H3K27me3 forms BLOCs over silent genes and intergenic regions and specifies a histone banding pattern on a mouse autosomal chromosome. Genome Res. Feb. 2009;19(2):221-33.

Peddigari et al., hnRNPL and nucleolin bind LINE-1 RNA and function as host factors to modulate retrotransposition. Nucleic Acids Res. Jan. 7, 2013;41(1):575-85.

Pellegrino et al., Interpretative strategies for lung function tests. Eur Respir J. Nov. 2005;26(5):948-68.

Percharde et al., A LINE1-Nucleolin Partnership Regulates Early Development and ESC Identity. Cell. Jul. 12, 2018;174(2):391-405. e19. 1-35.

Pichiorri et al., In vivo NCL targeting affects breast cancer aggressiveness through miRNA regulation. J Exp Med. May 6, 2013;210(5):951-68.

Pickup et al., The roles of TGFβ in the tumour microenvironment. Nat Rev Cancer. Nov. 2013;13(11):788-99.

Ramos et al., Computational and biological inference of gene regulatory networks of the LINE-1 retrotransposon. Genomics. Aug. 2007;90(2):176-85.

Ramos et al., The Intersection of Genetics and Epigenetics: Reactivation of Mammalian LINE-1 Retrotransposons by Environmental Injury. Environmental Epigenomics in Health and Disease: Epigenetics and Disease Origins. Heidelberg, Springer, 2013; pp. 127-160.

Rangasamy et al., Activation of LINE-1 Retrotransposon Increases the Risk of Epithelial-Mesenchymal Transition and Metastasis in Epithelial Cancer. Curr Mol Med. 2015;15(7):588-97.

Reck et al., Management of non-small-cell lung cancer: recent developments. Lancet. Aug. 24, 2013;382(9893):709-19.

Rengarajan et al., Exposure to polycyclic aromatic hydrocarbons with special focus on cancer. Asian Pac J Trop Biomed 2015; 5(3): 182-189.

Reyes-Reyes et al., A new paradigm for aptamer therapeutic AS1411 action: uptake by macropinocytosis and its stimulation by a nucleolin-dependent mechanism. Cancer Res. Nov. 1, 2010;70(21):8617-29.

Reyes-Reyes et al., LINE-1 couples EMT programming with acquisition of oncogenic phenotypes in human bronchial epithelial cells. Oncotarget. Oct. 23, 2017;8(61):103828-103842.

Reyes-Reyes et al., The aryl hydrocarbon receptor agonist benzo(a)pyrene reactivates LINE-1 in HepG2 cells through canonical TGF-β1 signaling: implications in hepatocellular carcinogenesis. Am J Cancer Res. May 1, 2016;6(5):1066-77.

Rhee et al., Prognostic significance of promoter CpG island hypermethylation and repetitive DNA hypomethylation in stage I lung adenocarcinoma. Virchows Arch. Jun. 2015;466(6):675-83.

Risch et al., Are female smokers at higher risk for lung cancer than male smokers? A case-control analysis by histologic type. Am J Epidemiol. Sep. 1, 1993;138(5):281-93.

Rodic et al., Long interspersed element-1 protein expression is a hallmark of many human cancers. Am J Pathol. May 2014;184(5):1280-6.

Ronaghi et al., Real-time DNA sequencing using detection of pyrophosphate release. Anal Biochem. Nov. 1, 1996;242(1):84-9.

Ross et al., Hypomethylation of repeated DNA sequences in cancer. Epigenomics. Apr. 2010;2(2):245-69.

Ruparel et al., Design and synthesis of a 3'-O-allyl photocleavable fluorescent nucleotide as a reversible terminator for DNA sequencing by synthesis. Proc Natl Acad Sci U S A. Apr. 26, 2005;102(17):5932-7.

Sanger et al., DNA sequencing with chain-terminating inhibitors. Proc Natl Acad Sci U S A. Dec. 1977;74(12):5463-7.

Schauer et al., L1 retrotransposition is a common feature of mammalian hepatocarcinogenesis. Genome Res. May 2018;28(5):639-653.

Scott et al., Origin of the human L1 elements: proposed progenitor genes deduced from a consensus DNA sequence. Genomics. Oct. 1987;1(2):113-25.

Shigematsu et al., Clinical and biological features associated with epidermal growth factor receptor gene mutations in lung cancers. J Natl Cancer Inst. Mar. 2, 2005;97(5):339-46.

Shiizaki et al., Modulation of benzo[a]pyrene-DNA adduct formation by CYP1 inducer and inhibitor. Genes Environ. Apr. 10, 2017;39:14. 8 pages.

Shukla et al., Endogenous retrotransposition activates oncogenic pathways in hepatocellular carcinoma. Cell. Mar. 28, 2013;153(1):101-11.

Singer et al., Homology between the Kpnl primate and BamH1 (M1F-1) rodent families of long interspersed repeated sequences. Nucleic Acids Res. Aug. 25, 1983;11(16):5739-45.

Singer. SINEs and LINEs: highly repeated short and long interspersed sequences in mammalian genomes. Cell. Mar. 1982;28(3):433-4.

Spira et al., Update in Lung Cancer 2014. Am J Respir Crit Care Med. Aug. 1, 2015;192(3):283-94.

Suter et al., Hypomethylation of L1 retrotransposons in colorectal cancer and adjacent normal tissue. Int J Colorectal Dis. Mar. 2004;19(2):95-101.

Symer et al., Human 11 retrotransposition is associated with genetic instability in vivo. Cell. Aug. 9, 2002;110(3):327-38.

Teneng et al., Context-specific regulation of LINE-1. Genes Cells. Oct. 2007;12(10):1101-10.

Teneng et al., Reactivation of L1 retrotransposon by benzo(a)pyrene involves complex genetic and epigenetic regulation. Epigenetics. Mar. 2011;6(3):355-67.

Thornburg et al., Transposable elements as a significant source of transcription regulating signals. Gene. Jan. 3, 2006;365:104-10.

(56)        References Cited

OTHER PUBLICATIONS

Tsay et al., Aryl hydrocarbon receptor and lung cancer. Anticancer Res. Apr. 2013;33(4):1247-56.

Tufarelli et al., LINE-1 activation and epigenetic silencing of suppressor genes in cancer: Causally related events? Mob Genet Elements. Sep. 1, 2013;3(5):e26832. 4 pages.

Voelkerding et al., Next-generation sequencing: from basic research to diagnostics. Clin Chem. Apr. 2009;55(4):641-58.

Ward et al., Rapid prenatal diagnosis of chromosomal aneuploidies by fluorescence in situ hybridization: clinical experience with 4,500 specimens. Am J Hum Genet. May 1993;52(5):854-65.

White et al., Sources of polycyclic aromatic hydrocarbons are associated with gene-specific promoter methylation in women with breast cancer. Environ Res. Feb. 2016;145:93-100.

Whongsiri et al., LINE-1 ORF1 Protein Is Up-regulated by Reactive Oxygen Species and Associated with Bladder Urothelial Carcinoma Progression. Cancer Genomics Proteomics. Mar.-Apr. 2018;15(2):143-151.

Wilhelm et al., Implications of LINE1 methylation for bladder cancer risk in women. Clin Cancer Res. Mar. 1, 2010;16(5):1682-9.

Wilkinson. In Situ Hybridization: A Practical Approach. Oxford University Press Inc., England. 1992. TOC only. 8 pages.

Witwer et al., Standardization of sample collection, isolation and analysis methods in extracellular vesicle research. J Extracell Vesicles. May 27, 2013;2. 25 pages.

Wolff et al., Hypomethylation of a LINE-1 promoter activates an alternate transcript of the MET oncogene in bladders with cancer. PLoS Genet. Apr. 22, 2010;6(4):e1000917. 13 pages.

Xia et al., LINE-1 retrotransposon-mediated DNA transductions in endometriosis associated ovarian cancers. Gynecol Oncol. Dec. 2017;147(3):642-647.

Xu et al., Prognostic significance of nuclear or cytoplasmic nucleolin expression in human non-small cell lung cancer and its relationship with DNA-PKcs. Tumour Biol. Aug. 2016;37(8):10349-56.

Xue et al., Variable Intra-Tumor Genomic Heterogeneity of Multiple Lesions in Patients With Hepatocellular Carcinoma. Gastroenterology. Apr. 2016;150(4):998-1008.

Yang et al., Identification of nucleolin and nucleophosmin as genotoxic stress-responsive RNA-binding proteins. Nucleic Acids Res. May 15, 2002;30(10):2251-60.

Yoshino et al., Induction of epithelial-mesenchymal transition-related genes by benzo[a]pyrene in lung cancer cells. Cancer. Jul. 15, 2007;110(2):369-74.

Zang et al., Differences in lung cancer risk between men and women: examination of the evidence. J Natl Cancer Inst. Feb. 21, 1996;88(3-4):183-92.

Zhang et al., LINE-1 Retrotransposition Promotes the Development and Progression of Lung Squamous Cell Carcinoma by Disrupting the Tumor-Suppressor Gene FGGY. Cancer Res. 2019; 79 (17): 4453-4465.

Zhang et al., Up-regulation of VCAM1 Relates to Neuronal Apoptosis After Intracerebral Hemorrhage in Adult Rats. Neurochem Res. May 2015;40(5):1042-52.

* cited by examiner

| Cells | Sex | Disease | Molecular phenotype |
|---|---|---|---|
| NCI-H460 | Male | NSCLC | wt p53 |
| NCI-H520 | Male | NSCLC | mut p53 |
| NCI-H1299 | Male | NSCLC | p53 Null |
| A549 | Male | NSCLC | wt p53, mut KRAS |
| BEAS-2B | Male | Non-malignant | SV40 T antigen |
| BZR | Male | Malignant | BEAS-2B, KRAS transformed |

A

B

| Cells | IC50 µM |
|---|---|
| NCI-H520 | 2.2 |
| NCI-H460 | 4.42 |
| NCI-1299 | 5.97 |
| BEAS-2B | 13.47 |
| BZR | 14.82 |

C

A

● Untreated  △ N6L

Tumor Size (mm3)

1400
1200
1000
800
600
400
200
0

*

2 4 6 8 10 12 14 16
Treatment days

B

● Untreated  -△- N6L

Weight (g)

35
30
25
20
15
10
5
0

5    10    15    20
Treatment days

C

|  | PBS | | | | N6L | | | |
| Tumor # | 7862 | 7869 | 7871 | 7874 | 7863 | 7864 | 7868 | 7872 |
| ORF1p | | | | | | | | |
| GAPDH | | | | | | | | |

A

Stacking Phase

B

C

SEQUENCE LISTING

<160> NUMBER OF SEQ ID NOS: 4

<210> SEQ ID NO 1
<211> LENGTH: 15

-continued

```
<212> TYPE: PRT
<213> ORGANISM: Artificial sequence
<220> FEATURE:
<223> OTHER INFORMATION: Synthetic

<400> SEQUENCE: 1

Met Gly Lys Lys Gln Asn Arg Lys Thr Gly Asn Ser Lys Thr Gln
1               5                   10                  15

<210> SEQ ID NO 2
<211> LENGTH: 26
<212> TYPE: DNA
<213> ORGANISM: Artificial sequence
<220> FEATURE:
<223> OTHER INFORMATION: Synthetic

<400> SEQUENCE: 2
ggtggtggtg gttgtggtgg tggtgg                                    26

<210> SEQ ID NO 3
<211> LENGTH: 21
<212> TYPE: DNA
<213> ORGANISM: Artificial sequence
<220> FEATURE:
<223> OTHER INFORMATION: Synthetic

<400> SEQUENCE: 3
ggucgucaua ccucagaagt t                                         21

<210> SEQ ID NO 4
<211> LENGTH: 21
<212> TYPE: DNA
<213> ORGANISM: Artificial sequence
<220> FEATURE:
<223> OTHER INFORMATION: Synthetic

<400> SEQUENCE: 4
cggugaaauu gauggaaaut t                                         21
```

SYSTEMS AND METHODS FOR CHARACTERIZING AND TREATING DISEASE

CROSS REFERENCE TO RELATED APPLICATIONS

This application is a U.S. 371 national phase entry of International Patent Application No. PCT/US2019/068952, filed Dec. 30, 2019, which claims priority to and the benefit of U.S. Provisional Application No. 62/787,444, filed Jan. 2, 2019, which are hereby incorporated by reference in their entireties.

SEQUENCE LISTING

The text of the computer readable sequence listing filed Jul. 2, 2021, titled "37218-252_ST25.txt", created Feb. 6, 2020, having a file size of 1,131 bytes, is hereby incorporated by reference in its entirety.

FIELD OF THE INVENTION

Provided herein are composition and methods for characterizing and treating disease. In particular, provided herein are compositions and methods for characterizing and treating disease (e.g., cancer) associated with activation of LINE-1 retroelements.

BACKGROUND OF THE INVENTION

Non-small cell lung cancers, which comprise 80-85% of lung cancer cases, have a five-year survival rate that is >90%, only if diagnosed early. Survival declines precipitously to less than 1% as diagnosis is delayed and the stage of disease progresses. Liver cancer is currently the second leading cause of cancer mortality worldwide, and the fifth leading cause of cancer deaths in the US, with hepatocellular carcinoma (HCC) by far the most common type of liver cancer. Low dose computerized tomography (LD-CT) improves early diagnosis of lung cancer, but has extremely high false positive rates, which have been documented to be as high as 95%, precipitating many unnecessary biopsies. In the developing world, hepatitis C virus (HCV) and hepatitis B virus (HBV) are the primary causes of HCC, while in the developed world alcohol abuse and nonalcoholic fatty liver disease are increasingly the major contributors. Over 520 million people worldwide are affected by HCV/HBV. HCC is curable by resection or ablation when diagnosed early, but unfortunately, most cases are diagnosed at advanced stages. To improve early lung and liver cancer diagnosis and treatment, it is therefore imperative to identify molecular biomarkers of cancer.

SUMMARY OF THE INVENTION

Advancing the early diagnosis of lung and liver cancer is imperative to improving the outcomes and survival of cancer patients and requires the discovery of novel biomarkers. LINE-1 (Long INterspersed nuclear Element-1) is a retrotransposon that is epigenetically silenced in healthy somatic cells but reactivated in cancer cells, where its expression is highly associated with lung cancer status, stage, and mortality. While measuring LINE-1 in lung biopsies is invasive and not practical for cancer screening, high throughput blood-based LINE-1 assays can be highly nonspecific. To overcome these obstacles, it is contemplated that examining LINE-1 in exosomes secreted from lung or liver epithelial cells serve as a proxy for LINE-1 levels in the tissue of origin.

To assess the feasibility of this hypothesis, experiments described herein used benzo[a]pyrene (BaP) to activate LINE-1 in lung cancer cells to assess whether exosomes are representative of cellular LINE-1 activation. LINE-1 mRNA and protein levels in cells and exosomes are highly correlated, indicating that lung-derived exosomes serve as a proxy of LINE-1 activation in the tissue. Thus, LINE-1 finds use as a biomarker in monitoring lung cancer status and response to treatment as well as the status of other diseases and conditions related to LINE-1.

Previous work established that tobacco carcinogens, including but not limited to, BaP reactivate LINE-1 in bronchial epithelial cells through displacement of NuRD corepressor complexes and interference with retinoblastoma-regulated epigenetic signaling. Experiments conducted during the course of developing embodiments for the present invention investigated whether LINE-1 in coordination with other genes within its regulatory network contribute to the in vivo genotoxic response to BaP remains. The results indicate that intratracheal instillation of transgenic ORFEUS$^{LSL}$ mice (mice that carry a single copy of human LINE-1) with BaP alone or in combination with adenovirus (adeno) CRE recombinase is genotoxic to the lung and associated with activation of the human LINE-1 transgene present in these mice. It was shown that LINE-1 reactivation modulated the expression of genes involved in oncogenic signaling and these responses were most pronounced in female mice compared to males and synergized by adeno-CRE recombinase. As such, these results implicate LINE-1 and genes within its oncogenic regulatory network with early sexually dimorphic responses of the lung in vivo.

Additional experiments demonstrated that EV LINE-1 content and RT activity can be quantified in cultured cells and clinical samples and supports the use of EV LINE-1 cargo as a biomarker of lung epithelial cell status.

Additional experiments demonstrated that higher circulating levels of L1-ORF1p are associated with lower lung function levels and increased risk for airflow limitation among former smokers.

Additional experiments determined that nucleolin (NCL) regulates expression of LINE1-ORF1p (L1-ORF1p) in non-small cell lung cancer (NSCLC) cells. Genetic knockdown of NCL significantly inhibited expression of L1-ORF1p in various NSCLC cell lines. Treatment with the investigational NCL antagonist N6L ablated L1-ORF1p expression in all cell lines constitutively expressing L1-ORFp. N6L displayed a stronger antiproliferative activity in NSCLC tumor cell lines expressing the highest L1-ORF1p protein levels. Moreover, N6L treatment of nude mice bearing NSCLC tumor xenografts blocked L1-ORF1p expression and effectively inhibited tumor growth. These data indicate that L1-ORF1p expression is regulated by NCL and identify NCL as a novel target for pharmacological inhibition of LINE1.

Accordingly, provided herein are compositions and methods for characterizing and treating disease (e.g., cancer) associated with activation of LINE-1 retroelements.

For example, in some embodiments, provided herein is a method of diagnosing lung and liver cancer, comprising: a) measuring the level of LINE-1 nucleic acids or polypeptides in a lung exosome isolated from a subject; and b) diagnosing lung cancer in the subject when the level of LINE-1 nucleic acids (e.g., mRNA) or polypeptides (e.g., ORF1p and/or ORF2p) are elevated. In some embodiments, the subject is a cigarette smoker. In some embodiments, the subject refrains from smoking for a period of time (e.g., 1 day, 1 week, one month, or more) prior to performing the method.

The present disclosure is not limited to a particular method of isolated exosomes. In some embodiments, exosomes are isolated using a method, comprising: i) centrifuging a blood sample from the subject to obtain a pellet; ii) subjecting the pellet to size exclusion chromatography to obtain an exosome fraction; and iii) performing immunocapture of exosomes on the exosome fraction. In some embodiments, the immunocapture is specific for exosomes from a specific tissue (e.g., cancerous or precancerous tissue) or cell. Exemplary sources of exosomes include, but are not limited to, lung tissue, liver tissue, bladder tissue, prostate tissue, breast tissue, ovarian tissue, colorectal tissue, esophageal tissue, stomach tissue, cancer cells, or cells infected with a virus. For example, in some embodiments, the immunocapture is specific for exosomes from lung cancer. In some embodiments, the immunocapture for lung exosomes comprises antibodies specific for one or more proteins selected, for example, SFTPA1, SFTPD, SCGB3A2, and DNAH5. In some embodiments, immunocapture for liver exosomes comprise antibodies specific for RDH16.

Further embodiments provide a method of diagnosing a disease or condition associated with altered LINE-1 levels in an exosome, comprising: a) measuring the level of LINE-1 nucleic acids or polypeptides in an exosome isolated from a subject; and b) diagnosing the disease or condition in the subject when the level of LINE-1 nucleic acids or polypeptides are elevated. The present disclosure is not limited to a particular disease. Examples include, but are not limited to, liver cancer, lung cancer, bladder cancer, prostate cancer, breast cancer, ovarian cancer, colorectal cancer, esophageal cancer, stomach cancer, COPD, or viral infection.

Additional embodiments provide a method for isolating exosomes from a blood sample, comprising: a) centrifuging a blood sample to obtain a pellet; b) subjecting the pellet to size exclusion chromatography to obtain an exosome fraction; and c) performing cell or tissue specific immunocapture of exosomes on the exosome fraction.

Yet other embodiments provide a method of treating a disease or condition associated with altered LINE-1 levels in an exosome, comprising: a) measuring the level of LINE-1 nucleic acids or polypeptides in an exosome isolated from a subject; and b) treating the disease or condition in the subject when the level of LINE-1 nucleic acids or polypeptides are elevated. In some embodiments, the treatment comprises a TGF-β1 inhibitor. In some embodiments, the treatment comprises a nucleolin antagonist (e.g., N6L).

Still other embodiments provide a method of monitoring treatment for a disease or condition associated with altered LINE-1 levels in an exosome, comprising: a) measuring the level of LINE-1 nucleic acids or polypeptides in an exosome isolated from a subject; b) treating the disease or condition in the subject when the level of LINE-1 nucleic acids or polypeptides are elevated; and c) repeating the step a) at least once (e.g., 1, 2, 3, 5, 10, or more times) after the b) treating. In some embodiments, step a) is repeated every day, week, month, or year or at another interval. In some embodiments, the results of the monitoring are used to alter the treatment based on the measuring. In some embodiments, the method further comprises performing a diagnostic assay based on the measuring.

For example, in some embodiments, levels of exosomal LINE-1 nucleic acids are polypeptides are used to select subjects with indeterminant nodules for liver lung biopsy, to select patients with liver tumors for biopsy or ablation therapy, to select patients with liver disease including HCV, HBV, and cirrhosis for treatment with interferon therapy, to select patients with liver disease or COPD for chemopreventive therapy with TGFb1 inhibitors, or as a prognostic indicator to guide the use of cytotoxic therapies to treat epithelial cancers (e.g., in some embodiments, LINE-1 drives "stem-ness" phenotype via genome plasticity. Cytotoxics or radiation therapy may result in adverse selection of stem-like cancer cells and thus resistant tumor recurrence. Thus, in some embodiments, these therapies are avoided in favor of targeted therapies). In some embodiments, the levels of exosomal LINE-1 nucleic acid or polypeptide levels are used in conjunction α-fetoprotein testing to improve ROC for liver cancer screening or in conjunction with low-dose CT to improve ROC for lung cancer screening.

In certain embodiments, provided herein is a method of preventing cancer, comprising detecting LINE-1 activation in a specific organ or cell suspected of being diseased to indicate high risk individuals (e.g., those with increased levels of exosomal LINE-1 nucleic acids or polypeptides) and then treating with TGF β 1 inhibitors, TGF β 1 effectors, PPAR gamma agonists, or nucleolin antagonists (e.g., N6L).

Also provided herein is the use of a TGF-β1 inhibitor to treat or prevent a disease or condition associated with altered LINE-1 levels in an exosome.

The present disclosure is not limited to a particular TGF-β1 inhibitor. Examples include, but are not limited to, pirfenidone, galunisertib, fresolumimab, trabederse, juglone and disitertide Additional embodiments are described herein.

Cell proliferation was determined by normalizing to the proliferation of untreated cells for each cell type. Error bars represent the SEM. Statistical significance was determined at 10 μM N6L comparing BEAS 2B versus H520, NCI-H460 and NCI-H1299 by ANOVA followed by Tukey's multiple comparisons test; n=4 ***p<0.0001 B) The half-maximal inhibitory concentration (IC50) of N6L was calculated after treatment for 72 h. C) Correlation between proliferation and L1-ORF1p protein levels.

Figure 15:
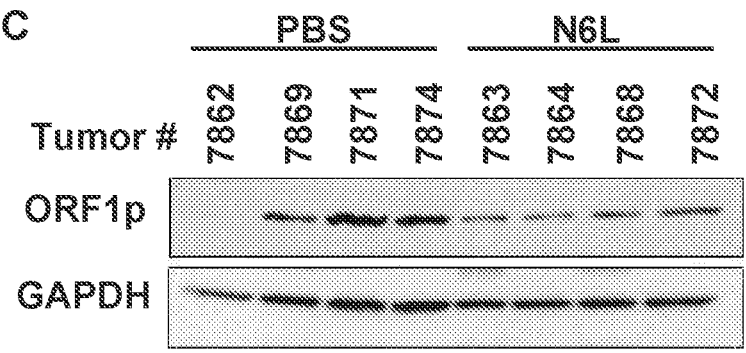

FIG. 15: Subcutaneous tumors were established after injection of 3×10$^6$ NCI-H520 cells into 5-week old male Nu/Nu mice. Mice were randomized into two groups and treated with either PBS or 10 mg/kg/day N6L in PBS three times per week given by intraperitoneal injection. A) Tumor volume; B) Body weights; C) LINE-1 expression in tumor tissue measured by immunoblotting using L1-ORF1p, and GAPDH antibodies. Statistical significance (*p=0.038) was determined by ANOVA followed by Tukey's multiple comparisons test. Error bars represent the SEM.

Figure 16:
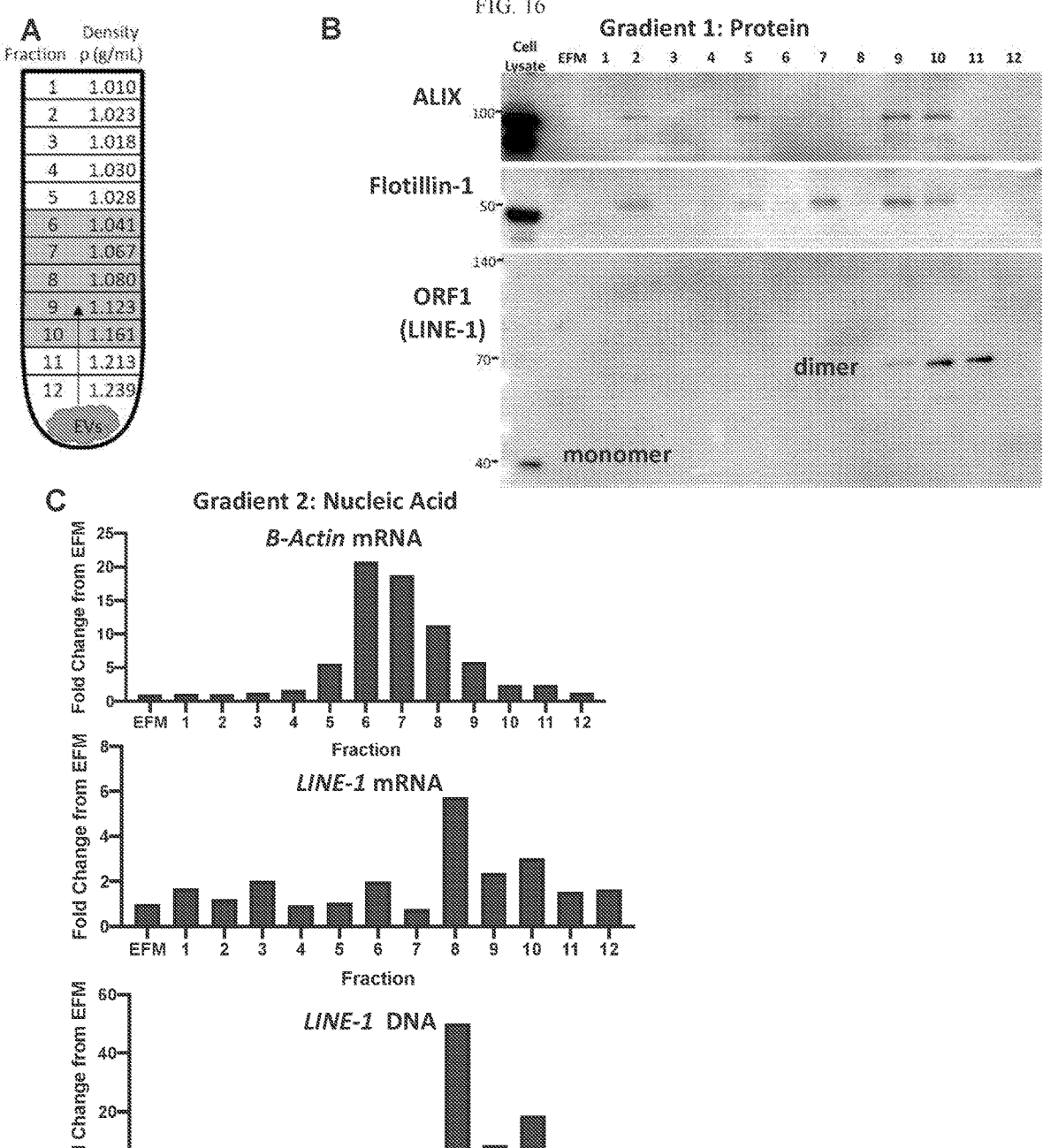

FIG. 16. LINE-1 mRNA and protein are present in EV iodixanol gradients. A. Iodixanol gradient fractions and average density. EVs were placed in the bottom fraction and rise to the level matching their density over an 18 h centrifugation period, which typically occurs between fractions 6-10, depending on the gradient. B. Proteins present in fractions 1-12 from Gradient #1. ALIX and Flotillin-1 are proteins typically enriched in EVs. ORF1p is visible as a dimer. Cell lysate shown as a positive control, EV-free media (EFM) as a negative control. C. Nucleic acids present in fractions 1-12 from Gradient #2, as determined by RT-qPCR and probe-based detection. All amplicons were expressed as fold change from EV-free medium (EFM). Representative images from two different experiments.

Figure 17:
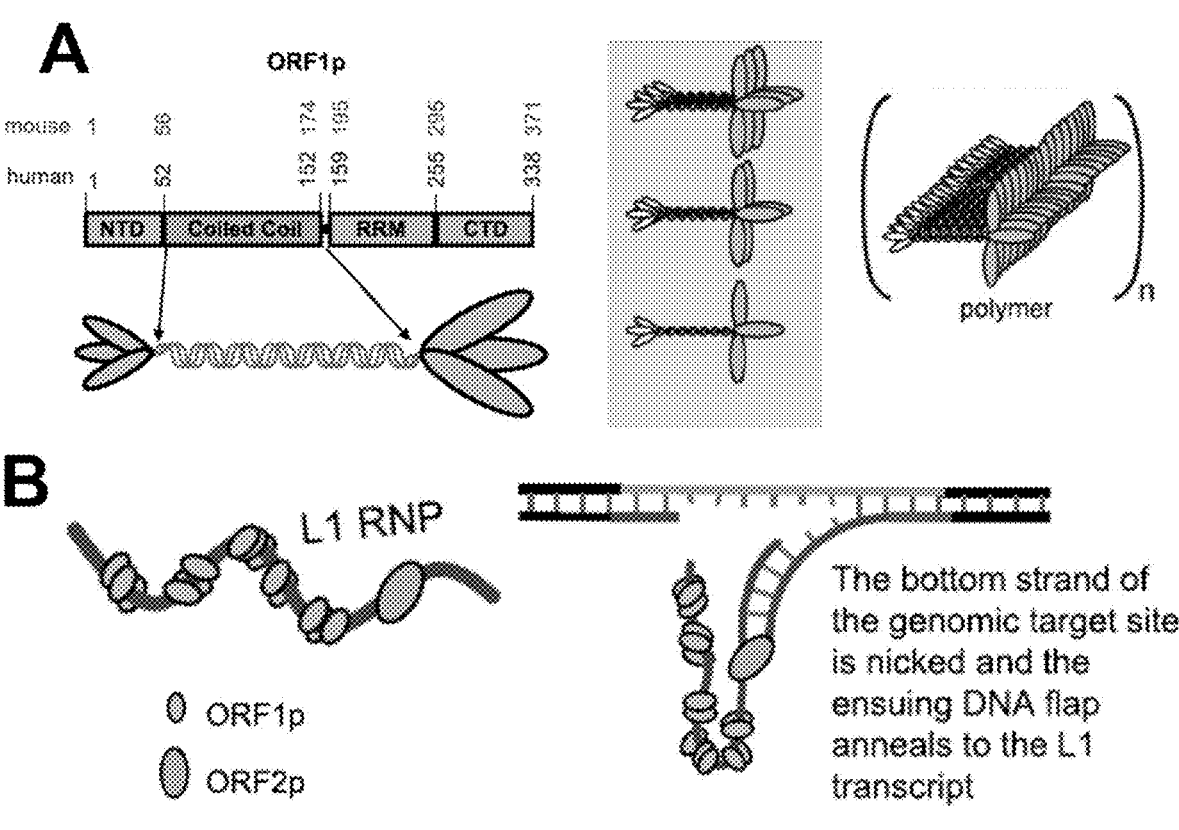

FIG. 17. LINE-1 ORF1 protein structure, multimeric binding, and LINE-1 ribonucleoprotein. From Naufer et al., 2019. A. ORF1 protein domains and trimer form, as well as higher order polymers. B. RNP structure and function.

Figure 18:
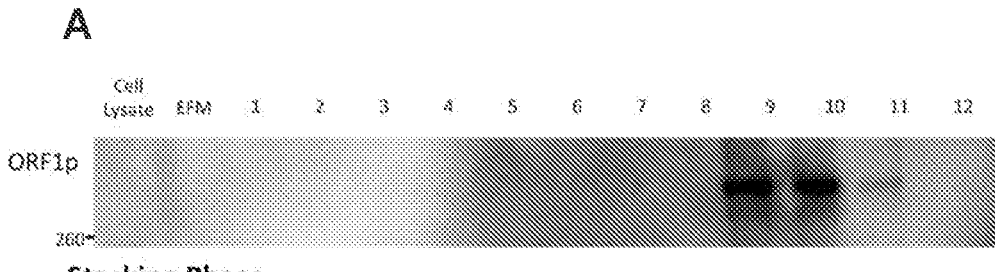
Figure 18:
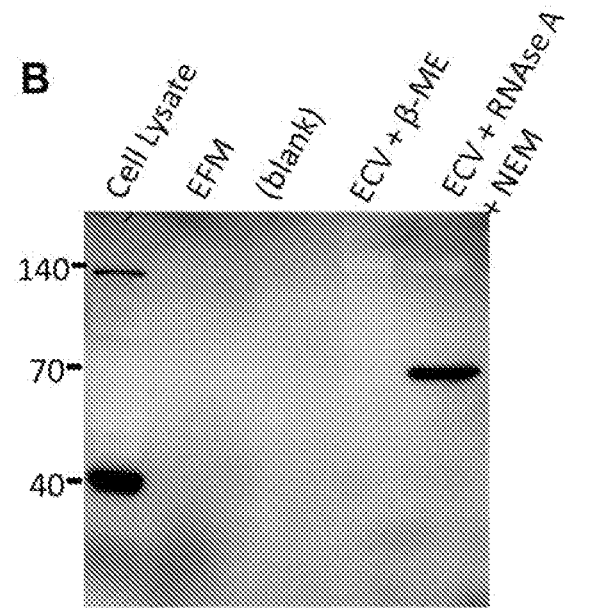
Figure 18:
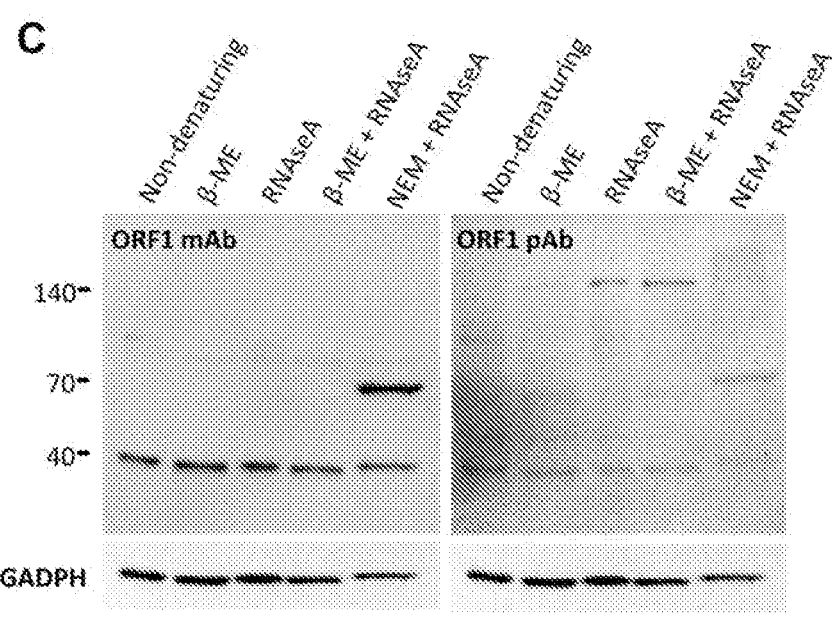

FIG. 18. Detection of ORF1p using SDS-PAGE. A. Initial SDS-PAGE of EV iodixanol fractions yielded a false negative signal for ORF1p and a large complex that could not enter the stacking phase of the gel. This complex was absent in the cell lysate (arrow). B. Efforts to break apart the ORF1p polymer or potential RNP required treatment of EV protein with RNAseA and N-ethylmaleimide to cap cysteine residues and to produce ORF1 dimers. C. Using cell lysate, the effects of RNAseA and NEM on ORF1p multimers were further investigated. RNAseA treatment resulted in formation of a ~140 kDa band that was detectable only with the polyclonal antibody (pAb). This complex is halved upon NEM treatment, yielding the ORF1p dimer.

Figure 19:
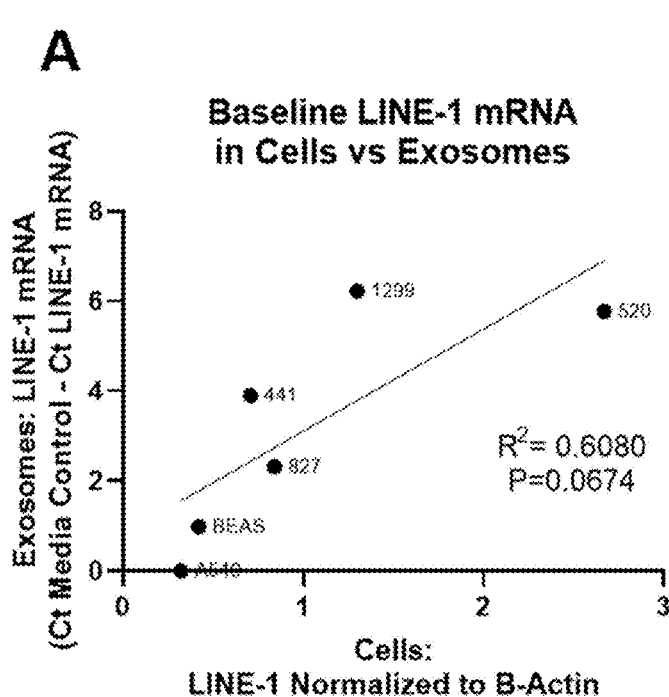
Figure 19:
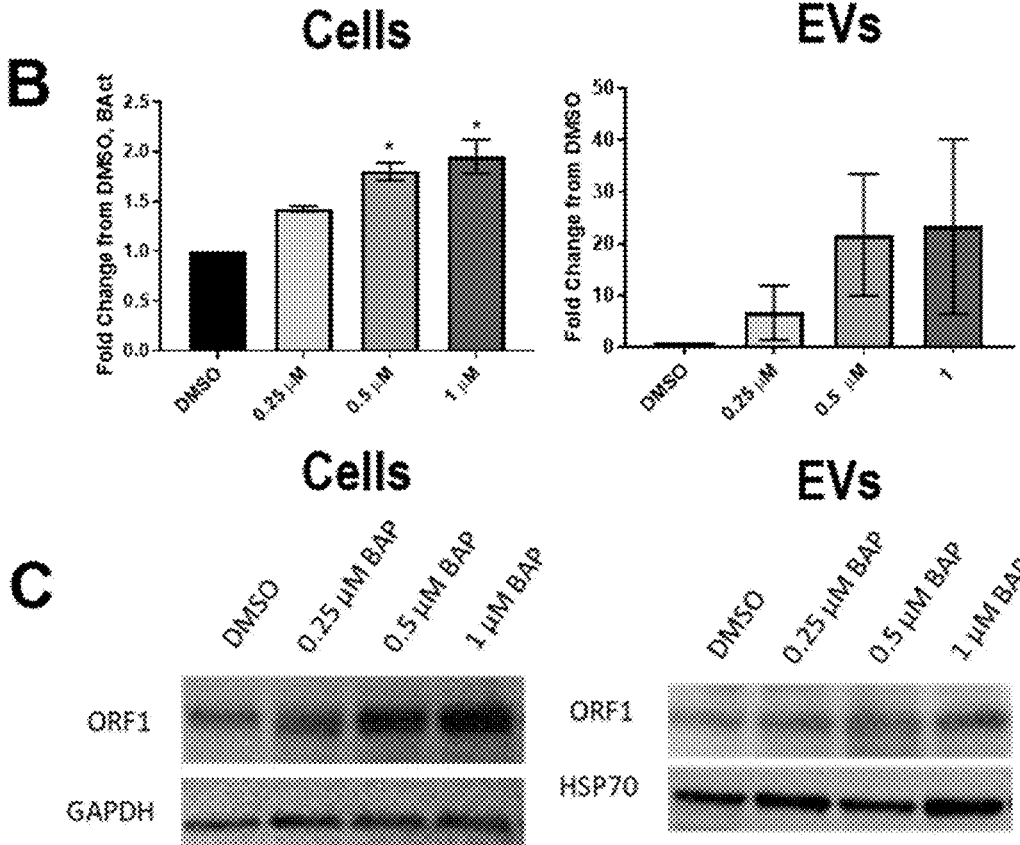

FIG. 19. Experiments demonstrating the biomarker potential of LINE-1 in EVs. A. Using a panel of six unstimulated lung epithelial cell lines, LINE-1 mRNA levels were quantified via qPCR in cells and EVs. For cells, LINE-1 mRNA values were normalized to B-Actin mRNA. For EVs, the LINE-1 mRNA Ct value was subtracted from the EFM media control. Mean shown, n=2-3. H460 cells were stimulated for 48 h with various concentrations of BaP to determine if cellular dose-dependent inductions were observed in EVs with respect to LINE-1 mRNA (B) and ORF1p (B). LINE-1 mRNA was quantified and expressed as a fold change from DMSO control. Mean shown. N=3.

Figure 20:
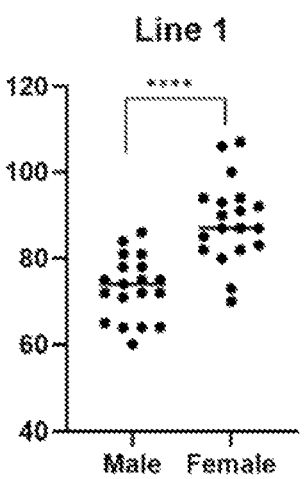
Figure 20:
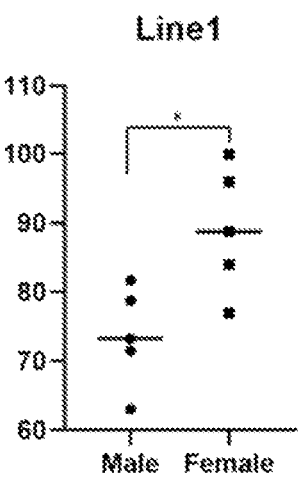

FIG. 20: tp53 mutant lung cancer samples (5 male and 5 female) were provided by the tissue acquisition and cellular/molecular analysis shared resource (tacmasr) of the ua cancer center. Formalin-fixed paraffin-embedded tissues from 5 male and 5 female lung cancers were processed for immunihistochemical detection of orf-1p using a custom-made antibody polyclonal antibody. Five different fields were examined per subject for a total of 50 assessments. Digital photomicrographs were acquired and analyzed with commercial image software to quantify signals. Statistical analysis revealed major differences in orf-1p expression, with females showing markedly increased signal intensities compared to males.

DEFINITIONS

To facilitate an understanding of the present invention, a number of terms and phrases are defined below:

As used herein, the terms "detect", "detecting" or "detection" may describe either the general act of discovering or discerning or the specific observation of a detectably labeled composition.

As used herein, the term "subject" refers to any organisms that are screened using the diagnostic methods described herein. Such organisms preferably include, but are not limited to, mammals (e.g., humans).

The term "diagnosed," as used herein, refers to the recognition of a disease by its signs and symptoms, or genetic analysis, pathological analysis, histological analysis, and the like.

As used herein, the term "stage of cancer" refers to a qualitative or quantitative assessment of the level of advancement of a cancer. Criteria used to determine the stage of a cancer include, but are not limited to, the size of the tumor and the extent of metastases (e.g., localized or distant).

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragments are retained. The term also encompasses the coding region of a structural gene and the sequences located adjacent to the coding region on both the 5' and 3' ends for a distance of about 1 kb or more on either end such that the gene corresponds to the length of the full-length mRNA.

Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues (e.g., biopsy samples), cells, and gases. Biological samples include blood products, such as plasma, serum and the like. Such examples are not however to be construed as limiting the sample types applicable to the present invention.

DETAILED DESCRIPTION OF THE INVENTION

Advancing the early detection of cancer is improved by the identification of molecular biomarkers that are highly precise, yet able to be implemented in high throughput screening.

Long Interspersed Nuclear Elements (LINEs) are a group of non-LTR (Long Terminal Repeat) retrotransposons widely distributed within the genome of eukaryotes (see, Jurka J. Curr Opinion Struct Biol 8:333-337, 1998; Singer M F. Cell 28:433-434, 1982). LINEs account for ~20% of the human genome sequence (see, Lander E S, et al., Nature 409:860-921, 2001), with most retroelements identified as molecular fossils devoid of activity (see, Grimaldi G, et al., Nucleic Acids Res 11:321-338, 1983; Lander E S, et al., Nature 409:860-921, 2001). About 100 full-length copies of human LINE-1 remain retrotransposition-competent and capable of mobilization through RNA intermediates (see, Badge R M, et al., Am J Hum Genet 72:823-838, 2003; Brouha B, et al., Proc Natl Acad Sci USA 100:5280-5285, 2003).

Full-length LINE-1 is ~6 kb in length, contains an internal bidirectional promoter, two open reading frames (ORFs) encoding ORF1 and ORF2, and a 3' poly-A tail. ORF1 is a 40 kDa protein with RNA-binding activity, while ORF2 is a 150 kDa protein with reverse transcriptase and endonuclease activities (see, Feng Q, et al., Cell 87:905-916, 1996; Mathias S L, et al., Science 254:1808-1810, 1991). Both proteins are required for retrotransposition (see, Mathias S L, et al., Science 254:1808-1810, 1991). The LINE-1 retrotransposition cycle entails three critical steps: 1) epigenetic reactivation and transcription of LINE-1; 2) cytoplasmic export of the mRNA for translation into proteins that bind the L1 transcript to form ribonucleoprotein complexes that return to the nucleus; and 3) cleavage of genomic DNA by ORF2p to create a free 3'-end for reverse transcription as well as new sites for genome integration (see, Ostertag E M, Kazazian H H. Biology of mammalian L1 retrotransposons. Annu Rev Genet 35:501-538, 2001).

LINE-1 'copies and pastes' itself and other DNAs into different loci throughout the genome via a reverse transcriptase-mediated mechanism. In a diploid human genome, 80-100 full-length retrotransposition-competent LINE-1s are present. In healthy somatic cells, LINE-1 is epigenetically silenced by repressive chromatin modifications and DNA methylation. These repressive marks can be removed by aberrant endogenous cellular processes and/or exposure to agents that induce DNA damage or perturb the epigenome. Reactivation of LINE-1 can reprogram the genome by causing insertion mutations or deletions that disrupt genome architecture and function. Additionally, LINE-1 activation can initiate aberrant gene expression changes that are independent of retrotransposition.

LINE-1 activation or hypomethylation have been observed in transformed epithelial cells (Belancio, V. P., et al, Gene. 2008; March 31; 411 (1-2): 38-45) from patient tumors of the liver (Shukla R, et al., Cell 153:101-111; B. Schauer S N, et al., Genome Research. 2018; 28 (5): 639-653), lung (Imperatori, A, et al., Lung Cancer. 2017; 108:83-89; D. Papasotiriou I, et al., PLoS ONE. 2017; 12 (2): e0171466; E. Clayton E A, et al., Frontiers in Molecular Biosciences. 2016; 3:76; F. Rhee, et al., Virchows Arch 2015; 466:675-83), intestines (Shukla et al., supra; Suter C M, et al., 2004; Int J Colorectal Dis 19:95-101; De Luca, C., et al., Oncotarget 2016; 7:4), bladder (Whongsiri P, et al., Cancer Genomics & Proteomics. 2018; 15 (2): 143-151;

Wolff, E M, et al., 2010; PLoS Genet 6: e1000917), ovarian (Xia Z, et al., Gynecol Oncol. 2017 December; 147 (3): 642-647), and breast (Clayton E A, et al., Frontiers in Molecular Biosciences. 2016; 3:76; DeRoo, L. A., et al., 2014; Carcinogenesis 35:333-338; White, A. J., et al., Environmental Research 2016; 145:93-100; Chen L., et al., Breast Cancer Res Treat. 2012; 136:129-42). The retrotransposition-independent effects of LINE-1 are mediated through the canonical TGF-β1 signaling pathway (mediated through TGFβR1/ALK5 and SMAD2/3), with an observable epithelial-to-mesenchymal transition (EMT) in liver (Reyes-Reyes E M, et al., Am J Cancer Res. 2016; 6 (5): 1066-107) and bronchial epithelial cells (Reyes-Reyes E. M., et al., Oncotarget. 2017 Oct. 23; 8 (61): 103828-103842). Ex vivo culture of human bronchial epithelial cells from smokers in the presence of cigarette smoke extract results in a TGFβ1 mediated EMT (Milara J, et al., Br J Pharmacol. 2010; December; 161 (7): 1599-615). Tobacco smoke constituents and inducers of oxidative stress reactivate LINE-1 in somatic tissues via epigenetic mechanisms (Milara et al., supra; Teneng I., et al., Epigenetics 2011; 6:355-367; Pauler, F. M., et al., Genome Res. 2009; 19:221; Ramos, K. S. and Bojang, P. Jr. LINE-1. Ref Module Biomed Sci, 2015). In fact, it has been shown that benzo (a) pyrene activated LINE-1 in HepG2 through the canonical TGFβ1 pathway in vitro (Reyes-Reyes et al., 2016, supra). Consistent with this observation in a HepG2 liver cell model system, ORF1p is correlated with hallmarks of EMT in staged liver tumors (Reyes-Reyes et al., 2016, supra), Breast cancer (DeRoo et al., supra; White et al., supra) and bladder cancer (Burger M, Catto J W F, et al., Eur Urol 2013; 63:234-241) have a higher incidence among smokers. In breast ductal tissue, ORF-2 protein encoded by LINE-1 is overexpressed in invasive ductal carcinomas (De Luca, C., et al., Oncotarget 2016; 7:4).

Hypomethylation of LINE-1 (an epigenetic marker for LINE-1 activation) in peripheral (circulating) DNA has been correlated with breast cancer risk in a cohort of breast cancer cases relative to subjects who do not have cancer (DeRoo et al., supra). Hypomethylation of LINE-1 has also been observed in breast cancer subjects exposed to polycyclic aromatic hydrocarbons (burning synthetic logs in the home) (DeRoo et al., supra). LINE-1 hypomethylation in DNA from the blood of women was a risk factor for bladder cancer (Wilhelm C S, et al., Clinical cancer research: an official journal of the American Association for Cancer Research. 2010; 16 (5): 1682-1689).

Collectively, these reports indicate LINE-1 activation as a linkage between chemical exposures known to be linked to malignant transformation of epithelial tissues and the well-characterized canonical TGFβ1 pathway. ORF1p is expressed in tumor tissue relative to adjacent normal tissue in bladder tumor tissues, and higher levels of ORF1p were observed in invasive tumors relative to less advanced cancer (Whongsiri et al., supra). Detection of hypomethylated LINE-1 in exfoliated urine cells of subjects with superficial transitional cell carcinoma, improves the specificity (retrospective analysis) of bladder cancer detection when combined with total antioxidant status in urine (Patchsung M, et al., PLoS ONE 7 (5): e37009). Finally, a metanalysis of published studies of LINE-1 hypomethylation in tumor tissue and blood confirmed significant differences in tumor LINE-1 methylation relative to subjects that do not have cancer, in breast, gastrointestinal, lung, and bladder cancers (Moon H G, et al., Am J Physiol Lung Cell Mol Physiol 2014; 307: L326-L337). However, the methylation status of LINE-1 in leukocyte and circulating DNA sources was less discriminating of disease status than LINE-1 status in diseased tissue (Moon et al., supra).

Hypomethylation has long been recognized as a hallmark of malignant transformation, and with LINE-1 representing 17% of the human genome (International Human Genome Sequencing Consortium. Nature. 2001; 409:860-921), hypomethylation of LINE-1 sequences represents largescale genome plasticity and probably contributes to localized chromosomal instability. HCC tumors are quite heterogenous, indicative of genome instability (Xue, Ruidong; et al., 2016 April; 150 (4): 998-1008). The most common mutations in HCC are the tumor suppressor gene TP53 (present in up to 40% of cancers, depending on stage); the gene for β catenin; CTNNB1 (about 25%, predominantly in HCV-related hepatocellular carcinoma). Other mutations are less frequent. HBx can bind and inactivate the tumor suppressor p53 in vitro, therefore increasing cellular proliferation and survival and compromising DNA-damage checkpoints (Feitelson M A, et al., Oncogene. 2002 Apr. 11; 21 (16): 2593-604). Farazi and DiPinho (Farazi P A, DePinho R A. et al., Nat Rev Cancer. 2006 September; 6 (9): 674-87) propose a model for genome instability as a mechanistic basis for HCV/HBV mediated oncogenesis which includes genome instability due to continuous replication (Kondo Y, et al., Hepatology 2000 November; 32 (5): 970-9), telomere erosion (Hao, X D, et al., Oncology Reports 2013; 29:226-236), p53 mutation, p53 inactivation, oxidative stress, and inflammation (L. Hussain et al., Oncogene. 2007; 2; 26 (15): 2166-76). p53 inactivation or mutation seems to be a consistent event in HBV-, HCV- and aflatoxin-B1-induced HCC (Farazi et al., supra).

Most efforts in personalized medicine have focused on the study of genes already known to be involved in the induction and progression of cancer. Hypomethylation of DNA from tumor tissue and blood has been examined in multiple cancers (Barchitta M, et al., 2014 PLoS ONE 9(10): e109478). While hypomethylation of LINE-1 DNA sequences might be an indicator of LINE-1 activation, the absence of sequence specific methylation might render hypomethylation an unreliable measure of LINE-1 activation. For example, genomic hypomethylation in colon cancer was not detectable in blood but was elevated in tumor tissue relative to coding region is not thought to be biologically important. Measuring aggregate methylated LINE-1 without sequence specific methylation data is an unreliable indicator of LINE-1 activation. Hypomethylated DNA while a very stable analyte, is not as direct a measure of LINE-1 activation as is LINE-1 mRNA or LINE-1 encoded proteins ORF1p and ORF2p.

Experiments described herein demonstrate that LINE-1 levels inside immune-isolated lung exosomes fits these criteria. In vitro experimentation was performed to demonstrate that cellular increases in LINE-1 activation products are mirrored within exosome cargo. Second, it was found that individuals with lung cancer exhibit elevated LINE-1 levels within their lung epithelial cell exosomes. These results provide evidence that exosome LINE-1 serves as a lung cancer biomarker and biomarker for other lung disease and other cancers.

Previous work established that tobacco carcinogens like BaP reactivate LINE-1 in bronchial epithelial cells through displacement of NuRD corepressor complexes and interference with retinoblastoma-regulated epigenetic signaling. Experiments conducted during the course of developing embodiments for the present invention investigated whether LINE-1 in coordination with other genes within its regulatory network contribute to the in vivo genotoxic response to BaP remains. The results indicate that intratracheal instillation of ORFEUS[LSL] mice with BaP alone or in combination with adenovirus (adeno) CRE recombinase is genotoxic to the lung and associated with activation of the human LINE-1 transgene present in these mice. It was shown that LINE-1 reactivation modulated the expression of genes involved in oncogenic signaling and these responses were most pronounced in female mice compared to males and synergized by adenoCRE recombinase. As such, these results implicate LINE-1 and genes within its oncogenic regulatory network with early sexually dimorphic responses of the lung in vivo.

Additional experiments demonstrated that EV LINE-1 content and RT activity can be quantified in cultured cells and clinical samples and supports the use of EV LINE-1 cargo as a biomarker of lung epithelial cell status.

Additional experiments demonstrated that higher circulating levels of L1-ORF1p are associated with lower lung function levels and increased risk for airflow limitation among former smokers.

Additional experiments determined that nucleolin (NCL) regulates expression of LINE1-ORF1p (L1-ORF1p) in non-small cell lung cancer (NSCLC) cells. Genetic knockdown of NCL significantly inhibited expression of L1-ORF1p in various NSCLC cell lines. Treatment with the investigational NCL antagonist N6L ablated L1-ORF1p expression in all cell lines constitutively expressing L1-ORFp. N6L displayed a stronger antiproliferative activity in NSCLC tumor cell lines expressing the highest L1-ORF1p protein levels. Moreover, N6L treatment of nude mice bearing NSCLC tumor xenografts blocked L1-ORF1p expression and effectively inhibited tumor growth. These data indicate that L1-ORF1p expression is regulated by NCL and identify NCL as a novel target for pharmacological inhibition of LINE1.

Accordingly, provided herein are compositions and methods for characterizing and treating disease (e.g., cancer) associated with activation of LINE-1 retroelements.

I. Isolation and Characterization of Exosomes

In some embodiments, the level of expression of LINE-1 nucleic acids or proteins are determined in an exosome. Exosomes are secreted membrane-bound vesicles approximately 30-150 nM in diameter that are formed by the endocytic pathway and contain DNA, RNA, and protein from their cell of origin. Exosome cargo can serve as biomarkers and regulate gene expression in recipient cells via paracrine mechanisms.

In some embodiments, exosomes that are associated with a specific disease, cell or tissue are selectively isolated. Exemplary sources of exosomes include, but are not limited to, lung tissue, liver tissue, bladder tissue, prostate tissue, breast tissue, ovarian tissue, colorectal tissue, esophageal tissue, stomach tissue, cancer cells, or cells infected with a virus.

The present disclosure is not limited to a particular method of isolated exosomes. In some embodiments, exosomes are isolated by the following steps (See e.g., Example 1): 1) centrifuging a blood sample from the subject to obtain a pellet; 2) subjecting the pellet to size exclusion chromatography to obtain an exosome fraction; and 3) performing immunocapture of exosomes on the exosome fraction. In some embodiments, the immunocaptures is specific for exosomes from a specific tissue (e.g., cancerous tissue) or cell. For example, in some embodiments, the immunocapture is specific for exosomes from lung cancer. In some embodiments, the immunocapture for lung exosomes comprises antibodies specific for one or more proteins selected, for example, SFTPA1, SFTPD, SCGB3A2, and DNAH5. In some embodiments, immunocapture for liver exosomes comprise antibodies specific for RDH16.

In some embodiments, following isolation of an exosome of interest, the level of LINE-1 nucleic acid (e.g., mRNA) or protein (e.g., ORF1p and/or ORF2p)

Exemplary nucleic acid detection techniques include but are not limited to: nucleic acid sequencing; nucleic acid hybridization; and, nucleic acid amplification.

A variety of nucleic acid sequencing methods are contemplated for use in the methods of the present disclosure including, for example, chain terminator (Sanger) sequencing, dye terminator sequencing, sequencing by synthesis, mass spectrometry, and high-throughput sequencing methods. Many of these sequencing methods are well known in the art. See, e.g., Sanger et al., Proc. Natl. Acad. Sci. USA 74:5463-5467 (1997); Maxam et al., Proc. Natl. Acad. Sci. USA 74:560-564 (1977); Drmanac, et al., Nat. Biotechnol. 16:54-58 (1998); Kato, Int. J. Clin. Exp. Med. 2:193-202 (2009); Ronaghi et al., Anal. Biochem. 242:84-89 (1996); Margulies et al., Nature 437:376-380 (2005); Ruparel et al., Proc. Natl. Acad. Sci. USA 102:5932-5937 (2005), and Harris et al., Science 320:106-109 (2008); Levene et al., Science 299:682-686 (2003); Korlach et al., Proc. Natl. Acad. Sci. USA 105:1176-1181 (2008); Branton et al., Nat. Biotechnol. 26 (10): 1146-53 (2008); Eid et al., Science 323:133-138 (2009); each of which is herein incorporated by reference in its entirety.

Next-generation sequencing (NGS) methods share the common feature of massively parallel, high-throughput strategies, with the goal of lower costs in comparison to older sequencing methods (see, e.g., Voelkerding et al., *Clinical Chem.*, 55:641-658, 2009; MacLean et al., *Nature Rev. Microbiol.*, 7:287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., Life Technologies/Ion Torrent, and Pacific Biosciences, respectively.

Illustrative non-limiting examples of nucleic acid hybridization techniques include, but are not limited to, in situ hybridization (ISH), microarray, and Southern or Northern blot. In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with either radio-, fluorescent- or antigen-labeled bases is localized and quantitated in the tissue using either autoradiography, fluorescence microscopy or immunohistochemistry, respectively. ISH can also use two or more probes, labeled with radioactivity or the other non-radioactive labels, to simultaneously detect two or more transcripts.

In some embodiments, LINE-1 nucleic acid levels are detected using fluorescence in situ hybridization (FISH). In some embodiments, FISH assays utilize bacterial artificial chromosomes (BACs). These have been used extensively in the human genome sequencing project (see *Nature* 409:953-958 (2001)) and clones containing specific BACs are available through distributors that can be located through many sources, e.g., NCBI. Each BAC clone from the human genome has been given a reference name that unambiguously identifies it. These names can be used to find a corresponding GenBank sequence and to order copies of the clone from a distributor.

The present invention further provides a method of performing a FISH assay on human cells (e.g., breast or endometrial cells). Specific protocols are well known in the art and can be readily adapted for the present invention. Guidance regarding methodology may be obtained from many references including: In situ Hybridization: Medical Applications (eds. G. R. Coulton and J. de Belleroche), Kluwer Academic Publishers, Boston (1992); In situ Hybridization: In Neurobiology; Advances in Methodology (eds. J. H. Eberwine, K. L. Valentino, and J. D. Barchas), Oxford University Press Inc., England (1994); In situ Hybridization: A Practical Approach (ed. D. G. Wilkinson), Oxford University Press Inc., England (1992)); Kuo, et al., *Am. J. Hum. Genet.* 49:112-119 (1991); Klinger, et al., *Am. J. Hum. Genet.* 51:55-65 (1992); and Ward, et al., *Am. J. Hum. Genet.* 52:854-865 (1993)). There are also kits that are commercially available and that provide protocols for performing FISH assays (available from e.g., Oncor, Inc., Gaithersburg, MD). Patents providing guidance on methodology include U.S. Pat. Nos. 5,225,326; 5,545,524; 6,121, 489 and 6,573,043. All of these references are hereby incorporated by reference in their entirety and may be used along with similar references in the art and with the information provided in the Examples section herein to establish procedural steps convenient for a particular laboratory.

Different kinds of biological assays are called microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes or transcripts (e.g., LINE-1 mRNA) by comparing gene expression in disease and normal cells or other populations. Microarrays can be fabricated using a variety of technologies, including but not limiting: printing with fine-pointed pins onto glass slides; photolithography using pre-made masks; photolithography using dynamic micromirror devices; ink-jet printing; or, electrochemistry on microelectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

Nucleic acids may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence-based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

In some embodiments, levels of LINE-1 polypeptides are detected (e.g., using immunoassays or mass spectrometry).

Illustrative non-limiting examples of immunoassays include, but are not limited to: immunoprecipitation; Western blot; ELISA; immunohistochemistry; immunocytochemistry; flow cytometry; and, immuno-PCR. Polyclonal or monoclonal antibodies detectably labeled using various techniques known to those of ordinary skill in the art (e.g., colorimetric, fluorescent, chemiluminescent or radioactive) are suitable for use in the immunoassays. Immunoprecipitation is the technique of precipitating an antigen out of solution using an antibody specific to that antigen. The process can be used to identify protein complexes present in cell extracts by targeting a protein believed to be in the complex. The complexes are brought out of solution by insoluble antibody-binding proteins isolated initially from bacteria, such as Protein A and Protein G. The antibodies can also be coupled to sepharose beads that can easily be isolated out of solution. After washing, the precipitate can be analyzed using mass spectrometry, Western blotting, or any number of other methods for identifying constituents in the complex.

A Western blot, or immunoblot, is a method to detect protein in a given sample of tissue homogenate or extract. It uses gel electrophoresis to separate denatured proteins by mass. The proteins are then transferred out of the gel and onto a membrane, typically polyvinyldifluoride or nitrocellulose, where they are probed using antibodies specific to the protein of interest. As a result, researchers can examine the amount of protein in a given sample and compare levels between several groups.

An ELISA, short for Enzyme-Linked ImmunoSorbent Assay, is a biochemical technique to detect the presence of an antibody or an antigen in a sample. It utilizes a minimum of two antibodies, one of which is specific to the antigen and the other of which is coupled to an enzyme. The second antibody will cause a chromogenic or fluorogenic substrate to produce a signal. Variations of ELISA include sandwich ELISA, competitive ELISA, and ELISPOT. Because the ELISA can be performed to evaluate either the presence of antigen or the presence of antibody in a sample, it is a useful tool both for determining serum antibody concentrations and also for detecting the presence of antigen.

Immuno-polymerase chain reaction (IPCR) utilizes nucleic acid amplification techniques to increase signal generation in antibody-based immunoassays. Because no protein equivalence of PCR exists, that is, proteins cannot be replicated in the same manner that nucleic acid is replicated during PCR, the only way to increase detection sensitivity is by signal amplification. The target proteins are bound to antibodies which are directly or indirectly conjugated to oligonucleotides. Unbound antibodies are washed away and the remaining bound antibodies have their oligonucleotides amplified. Protein detection occurs via detection of amplified oligonucleotides using standard nucleic acid detection methods, including real-time methods.

Mass spectrometry has proven to be a valuable tool for the determination of molecular structures of molecules of many kinds, including biomolecules, and is widely practiced today. Purified proteins are digested with specific proteases (e.g. trypsin) and evaluated using mass spectrometry. Many alternative methods can also be used. For instance, either matrix-assisted laser desorption/ionization (MALDI) or electrospray ionization (ESI) mass spectrometric methods can be used. Furthermore, mass spectroscopy can be coupled with the use of two-dimensional gel electrophoretic separation of cellular proteins as an alternative to comprehensive pre-purification. Mass spectrometry can also be coupled with the use of peptide fingerprint database and various searching algorithms. Differences in post-translational modification, such as phosphorylation or glycosylation, can also be probed by coupling mass spectrometry with the use of various pretreatments such as with glycosylases and phosphatases. All of these methods are to be considered as part of this application.

In some embodiments, electrospray ionisation quadrupole mass spectrometry is utilized to detect LINE-1 polypeptide levels (See e.g., U.S. Pat. No. 8,658,396; herein incorporated by reference in its entirety).

In some embodiments, a computer-based analysis program is used to translate the raw data generated by the detection assay (e.g., the presence, absence, or amount of a given marker or markers) into data of predictive value for a clinician (e.g., present of a disease or condition or status of a treatment). The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., LINE-1 nucleic acid or protein levels), specific for the diagnostic, therapeutic, or prognostic information desired for the subject.

The profile data is then prepared in a format suitable for interpretation by a treating clinician. For example, rather than providing raw expression data, the prepared format may represent a diagnosis or risk assessment (e.g., LINE-1 nucleic acid or protein levels) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may choose further intervention or counseling based on the results. In some embodiments, the data is used for research use. For example, the data may be used to further optimize the inclusion or elimination of markers as useful indicators of a particular condition or stage of disease or as a companion diagnostic to determine a treatment course of action.

Compositions for use in the screening, diagnostic, prognostic, and therapeutic methods described herein include, but are not limited to, probes, amplification oligonucleotides, and the like. In some embodiments, kits include all components necessary, sufficient or useful for detecting the markers described herein (e.g., reagents, controls, instructions, etc.). The kits described herein find use in research, therapeutic, screening, and clinical applications.

The probe and antibody compositions of the present invention may also be provided in the form of an array.

II. Method of Diagnosing, Characterizing, Monitoring, and Treating Disease

In some embodiments, the present disclosure provides compositions and methods for characterizing, diagnosing, monitoring, and treating disease based on levels of LINE-1 nucleic acids and polypeptides. For example, in some embodiments, an increased level of LINE-1 mRNA and/or polypeptides is associated with a diagnosis of a disease or condition. Examples include, but are not limited to, liver cancer, lung cancer, bladder cancer, prostate cancer, breast cancer, ovarian cancer, colorectal cancer, esophageal cancer, stomach cancer, COPD, or viral infection. In some specific examples, the disease is lung cancer, liver cancer, or chronic obstructive pulmonary disease (COPD).

In some embodiments, the levels of LINE-1 nucleic acids or proteins are used to screen for individuals at risk of disease or to identify individuals that may have a disease. In some embodiments, such individuals are high risk individuals (e.g., smokers). In some embodiments, smokers are asked to refrain from smoking for a period of time (e.g., 1 day, 1 week, 1 month, or another time period) before providing a sample.

In some embodiments, individuals identified as have elevated levels of LINE-1 nucleic acids or proteins are identified as needing further diagnostic tests (e.g., imaging, biopsy, etc.). In some embodiments, the LINE-1 assay serves as a screening assay for the general or at-risk population and is repeated at regular intervals (e.g., monthly, yearly, or more or less often).

In some embodiments, levels of LINE-1 nucleic acids or polypeptides are used to monitor treatment (e.g., determine response to a drug or other treatment) for a disease or condition described herein (e.g., to determine or alter a treatment course of action). For example, in some embodiments, LINE-1 nucleic acid or polypeptide levels are measured at regular intervals before, during, or after treatment (e.g., daily, weekly, monthly, or less often). In some embodiments, LINE-1 levels are used to recommend an increase, decrease, or chance in treatment.

For example, in some embodiments, levels of exosomal LINE-1 nucleic acids are polypeptides are used to select subjects with indeterminant nodules for liver lung biopsy, to select patients with liver tumors for biopsy or ablation therapy, to select patients with liver disease including HCV, HBV, and cirrhosis for treatment with interferon therapy, to select patients with liver disease or COPD for chemopreventive therapy with TGFb1 inhibitors, or as a prognostic indicator to guide the use of cytotoxic therapies to treat epithelial cancers (e.g., in some embodiments, LINE-1 drives "stem-ness" phenotype via genome plasticity. Cytotoxics or radiation therapy may result in adverse selection of stem-like cancer cells and thus resistant tumor recurrence. Thus, in some embodiments, these therapies are avoided in favor of targeted therapies). In some embodiments, the levels of exosomal LINE-1 nucleic acid or polypeptide levels are used in conjunction $\alpha$-fetoprotein testing to improve ROC for liver cancer screening or in conjunction with low-dose CT to improve ROC for lung cancer screening.

In certain embodiments, provided herein is a method of preventing cancer, comprising detecting LINE-1 activation in a specific organ or cell suspected of being diseased to indicate high risk individuals (e.g., those with increased levels of exosomal LINE-1 nucleic acids or polypeptides) and then treating with TGF $\beta$ 1 inhibitors or drugs that modulate TGF $\beta$ 1 effectors.

In some embodiments, individuals with elevated LINE-1 nucleic acid levels are administered a TGF-$\beta$1 inhibitor. Some of the genetic targets of L1 are also regulated by TGF-$\beta$1 signaling pathway (e.g., CCL2, ICAM CXCL1) or effectors of the TGF $\beta$ 1 pathway (SMAD2, SMAD3, TGF $\beta$ R1, TGF $\beta$ R2). Thus, the TGF-$\beta$1 signaling pathway is involved in some of the carcinogenesis functions of LINE-1 (See e.g., WO 2017/172839; herein incorporated by reference in its entirety). The present disclosure is not limited to a particular TGF-$\beta$1 inhibitor. Examples include, but are not limited to, pirfenidone, galunisertib, fresolumimab, trabedersen, juglone and disitertide. Additional examples include, but are not limited to, curcumin, omega-3 fatty acid and analogs, PPAR gamma agonists, resolvins, maresins, protectins, and oxolipids.

In some embodiments, individuals with elevated LINE-1 nucleic acid levels are administered a nucleolin antagonist (e.g., N6L).

In some embodiments, individuals with elevated LINE-1 nucleic acid levels are administered an agent that inhibits the activity or expression of one or more of the following genes: Chemokine (CeC motif), ligand 2 (CCL2), Cytochrome P450, family 2, subfamily a, polypeptide, 4 (CYP2A4), Microsomal glutathione S-transferase 1, (MGST1), Phenyl-alanine hydroxylase (PAH), Periostin, Osteoblast specific factor (POSTN), Protein tyrosine phosphatase, receptor type, B (PTPRB), and Vascular cell adhesion molecule 1 (VCAM1), Chemokine (CeXeC motif) ligand 1 (CXCL1), Ectopic viral integration site 2a (EVI2A), Gap junction membrane channel protein, alpha 1 (GJA1), RNA binding motif protein 39 (RBM39), Chloride intracellular channel 3 (CLIC3), Protein kinase inhibitor alpha (PKIA), Regulator of G-protein Signaling (RGS), Cysteine dioxygenase 1 (CDO1), D site albumin promoter binding protein (DBP), DnaJ (Hsp40) homolog, subfamily B member 9 (DNAJB9), Myosin light polypeptide 7 (MYL7), Nemo-like kinase (NLK), or Preimplantation protein 4 (PREI4) [Bojang Molecular Oncology 7:2013; 812-825.

In some embodiments, in addition to or instead of treatment with a TGF-β1 inhibitor and/or a nucleolin antagonist (e.g., N6L), individuals are administered a further treatment for their LINE-1 associated disease or condition (e.g., cancer or COPD).

In some embodiments, subjects are administered additional chemotherapy agents. The particular chemotherapy agent is based on a recommended treatment that considers the subject's age, stage of cancer, and presence of markers on the cancer cell. Examples include, but are not limited to, anthracyclines, such as doxorubicin, pegylated liposomal doxorubicin, and epirubicin, taxanes, such as paclitaxel, albumin-bound paclitaxel, and docetaxel, 5-fluorouracil (5-FU), cyclophosphamide, carboplatin, platinum agents (e.g., cisplatin, carboplatin), vinorelbine, capecitabine, gemcitabine, methotrexate, ixabepilone, eribulin, trastuzumab, pertuzumab, ado-trastuzumab emtansine, sorafenib, lapatinib, neratinib, palbociclib, ribociclib, abemaciclib, everolimus, bevacizumab, ramucirumab, necitumumab, and olaparib. Additional treatments for cancer include surgery, radiation, immunotherapy (e.g., atezolizumab, durvalumab, nivolumab, and pembrolizumab), and the like.

Treatments for COPD include, but are not limited to, bronchodilators (e.g., albuterol, levalbuterol, ipratropium, ipratropium bromide and albuterol, aclidinium, arformoterol, formoterol, indacaterol, salmeterol, tiotropium) and inhaled corticosteroids (e.g., budesonide and fluticasone).

EXPERIMENTAL

The following examples are provided in order to demonstrate and further illustrate certain preferred embodiments and aspects of the present invention and are not to be construed as limiting the scope thereof.

Example 1

Materials and Methods

Tissue Culture and In Vitro Exposure

Human 460 large cell lung carcinoma cells were authenticated by the UA tissue culture core facility and then cultured in RPMI media (Gibco) supplemented with 10% exosome-free FBS. One day before exposure, cells were counted, seeded, and allowed to attach overnight. Prior to each exposure, medium was removed and cells were washed with PBS to remove cellular debris and extracellular vesicles. After exposure, culture medium was harvested for exosome collection, cells were detached with trypsin-EDTA (Gibco), counted via hemocytometer, and cell viability was assessed using trypan blue exclusion.

Exosome Isolation and Characterization

Cell media was centrifuged at 500×g for 5 minutes to remove cells and large debris and then stored at −80° C. To isolate exosomes, cell medium was centrifuged at 25,000×g for 1.5 hours to remove apoptotic bodies and other large extracellular vesicles. To precipitate exosomes, polyethylene glycol (PEG) MW 6,000 was added to the supernatant to a final concentration of 10% (w/v), and centrifuged again at 15,000×g for 30 minutes. Each exosome pellet was resuspended in 2 mL PBS, which was then subdivided into fractions for Nanosight Nanoparticle Tracking Analysis (NTA), nucleic acid extraction, and protein extraction. Nucleic acids and proteins present outside of exosomes were enzymatically digested to prevent confounding of exosome cargo analysis. Exosome fractions designated for nucleic acid analysis were treated with DNAseI for 30 minutes at 37° C. and RNAseA for 5 minutes at RT and then supplemented with RNA Secure (Invitrogen) prior to lysis. Exosome fractions designated for protein analysis were treated with proteinaseK for 30 minutes at 37° C. Following enzymatic digestion, exosomes were pelleted a final time by addition of PEG 6,000 to 10%, and centrifugation at 15,000×g for 15 minutes. To assess exosome size and quantity, Nanosight NTA was performed. Each sample was read five times and the sample grand mean and standard error for each nanoparticle size bin were reported. Nanosight experiments were performed in technical duplicate. Exosome morphology was examined using transmission electron microscopy.

Nucleic Acid Extraction and qPCR

Nucleic acids were extracted from cell and exosome pellets using the Quick DNA-RNA Miniprep Plus. RNA was subjected to an additional DNAseI digestion on-column (RNA from cells) or prior to reverse transcription (RNA from exosomes; Turbo DNA-free; Invitrogen). Following isolation DNA and RNA quantity and integrity were assessed using the Cytation X system. LINE-1 mRNA was detected in equal volumes of exosome RNA using OneStep RT-qPCR (NEB). To assess cellular LINE-1 mRNA levels, LINE-1 mRNA was normalized to B-Actin mRNA and expressed as a fold change from control using the Pfaffl technique. To assess exosome mRNA levels, the fluorescence at cycle 38 (within the linear phase) for FAM (LINE-1 mRNA probe) and JOE (BActin mRNA probe) were used as they were continuous variables that did not rely on fold change values. Briefly, the fluorescence units from the reverse transcription control (RTC; no reverse transcriptase enzyme) for each sample was subtracted from the complete sample amplification and the remaining fluorescence units were divided by cell number. The resulting values approximate the amount of LINE-1 or BActin mRNA present in exosomes that is also normalized by cell number. LINE-1 DNA copies were quantified using absolute qPCR quantification. Briefly, known copy numbers of plasmids bearing the LINE-1 sequence were used to create a standard curve, which could then be used to calculated copy number from samples. These copy numbers were then divided by cell number to yield the number of LINE-1 DNA copies per cell (cellular DNA) and the number of exosome LINE-1 DNA copies per cell (exosome DNA).

Protein Extraction and Immunoblotting

Cell and exosome pellets were lysed using RIPA (50 mM Tris, pH 8.0; 150 mM NaCl; 1% Triton X-100; 400 μM EDTA; 10% glycerol; 0.1% SDS; 0.1% deoxycholate) buffer supplemented with PMSF (Sigma), protease inhibitor cocktail (Roche), and phosphatase inhibitors. After incubation on ice for 15 minutes, debris was pelleted by centrifugation at 16,000×g for 10 minutes. Protein quantity was assessed via BCA assay (Pierce). Prior to analysis RIPA buffer was supplemented with Laemmli buffer (60 mM Tris, pH 6.8; 200 mM DTT; 10% glycerol; 2% SDS; 0.05% bromophenol blue) and heated at 95° C. for 5 minutes. Equal amounts of protein were used for SDS-PAGE. Protein was transferred on to nitrocellulose membranes and incubated with the indicated primary antibodies, followed by incubation with horseradish peroxidase (HRP)-conjugated secondary antibodies. Chemiluminesence was visualized using Pierce Enhanced Chemiluminescence (ECL) Western blotting substrate (Pierce) and film detection. Densitometric analysis of Western blots was performed using ImageJ (NIH). Proteins were normalized to GAPDH and expressed a fold change from DMSO control.

Immunoisolation of Lung Exosomes

Blood was collected from human subjects using sodium-citrate anticoagulant and centrifuged at 1,500×g for 30 minutes and frozen in aliquots at −80° C. until ready for use. After thawing, extracellular vesicles were purified from plasma using size exclusion chromatography (Izon), followed by concentration with 100 kd size exclusion columns (Millipore). Exosomes were resuspended in PBS 0.05% Tween-20 and incubated with biotinylated capture antibodies overnight at 4° C. The following morning, streptavidin-coated magnetic beads (Invitrogen) were added and incubated for an additional 2 h. The exosome-bead complexes were stained and then quantified using beads using flow cytometry, qPCR, and Western blotting.

Results

LINE-1 is Expressed in Lung Cancer

Given that LINE-1 hypomethylation is highly associated with lung cancer stage and mortality, several lung tumors and cancer cell lines were assayed for LINE-1 expression. It was found that in lung tumors that are p53 negative, which comprise the majority of lung cancer tumors, LINE-1 is activated.

Isolation Method Yields Exosome-Like Vesicles

Figure 1:
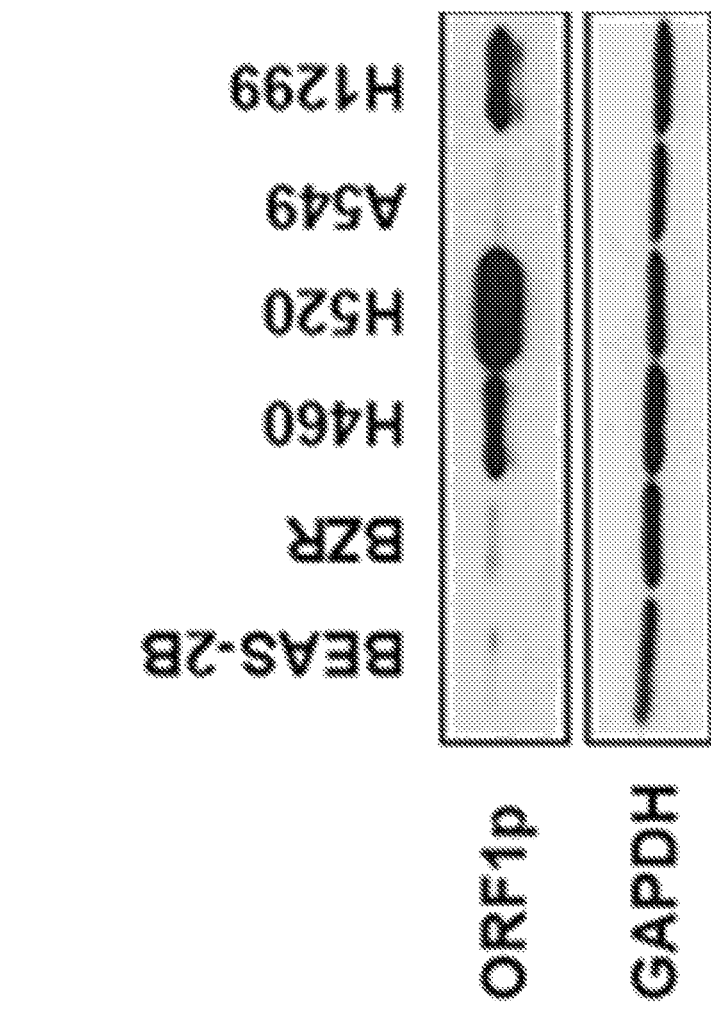
FIG. 1. LINE-1 protein expression in NSC lung cancers and lung cell lines. A, LINE-1 immunohistochemistry in lung tumors. B, ORF1 presence in commonly detected lung cancer and transformed cell lines.
Figure 2:
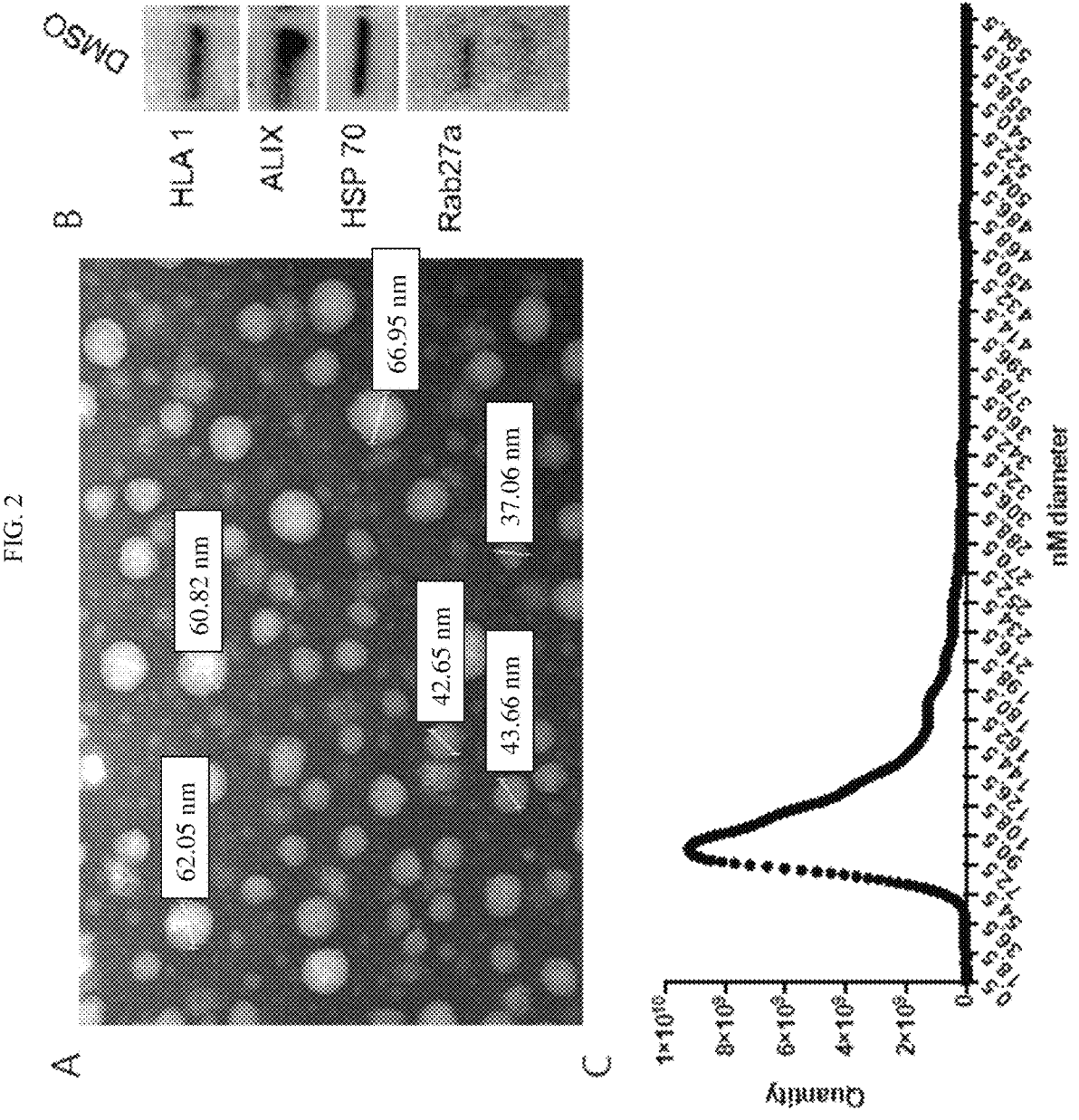
FIG. 2. Vesicles isolated from H460 cell medium exhibit protein, size, and morphology consistent with exosomes. A, Scanning electron microscopy depicts spherical vesicles with diameters characteristic of exosomes. B, Western blot of vesicles detects the presence of protein associated with exosomes (ALIX, HSP70, and Rab27a) and other extracellular vesicles (HLAI). C, Nanostring NTA analysis of exosome preparation demonstrates that vast majority of vesicles isolated are between 50 and 150 nM in diameter and absence of large debris.

A method was developed to isolate extracellular vesicles based on a combination of ultracentrifugation and PEG-based precipitation. The morphology, size, and protein composition of the purified vesicles were examined for the presence of exosome characteristics and the relative absence of contaminating debris and larger extracellular vesicles, such as microvesicles (100-1,000 nM) and apoptotic bodies (1,000-5,000 nM) (György et al., 2011). An EM micrograph (FIG. 2A) depicts spherical vesicle-like bodies with diameters within the anticipated exosome size range of 30-150 nM. This finding was confirmed by Nanosight NTA analysis, which revealed that the majority of vesicles were within this range (FIG. 2C). Western blot analysis of vesicles (FIG. 2B) revealed the presence of proteins enriched specifically in exosomes (ALIX and Rab27a). Taken together, these findings indicate that the purified vesicles are exosomes with little contaminating debris.

Effect of BaP on Bulk Exosome Production

The relationship between LINE-1 and exosome biology is largely undefined, with major questions regarding the presence and amounts of LINE-1 molecules within exosomes. As a first step toward answering these questions, the model carcinogen benzo[a]pyrene was used to induce LINE-1 expression in H460 large cell lung cancer cells and then examined LINE-1 levels in the released exosomes.

Figure 7:
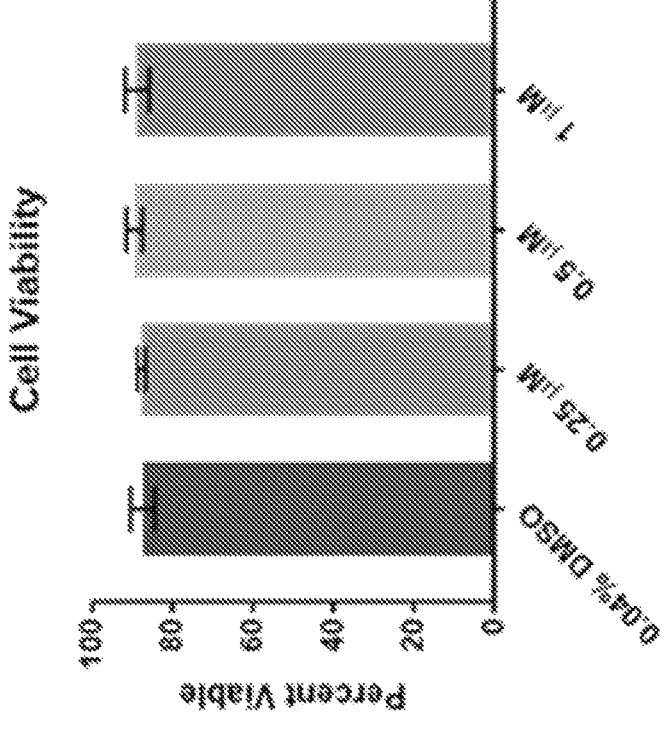
FIG. 7. 48 h BaP exposure reduces proliferation but does not affect cell viability.
Figure 7:
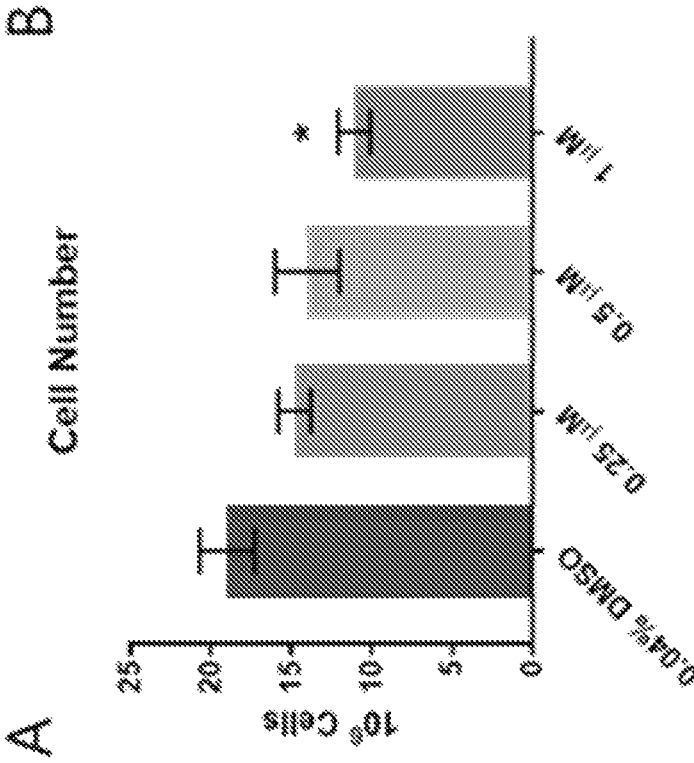

The effect of BaP exposure on general culture parameters such as cell viability, proliferation, the number of exosomes released, and the size of exosomes released was assessed. Although BaP did not elicit cytotoxicity at the concentrations used, it did reduce cell proliferation in a dose-dependent manner (FIG. 7). At the conclusion of the 48 hour exposure, DMSO-treated cells had a mean (±SEM) of 19±1.7 million cells, which declined with increasing BaP concentration to 14.8±1.7 (0.25 µM), 14.0±2.3 (0.5 µM), and a statistically signification reduction to 11.1±1.9 at 1 µM. To ensure that these reductions did not confound subsequent characterization of exosome biology, a cell number normalization step was used in data analyses.

Figure 3:
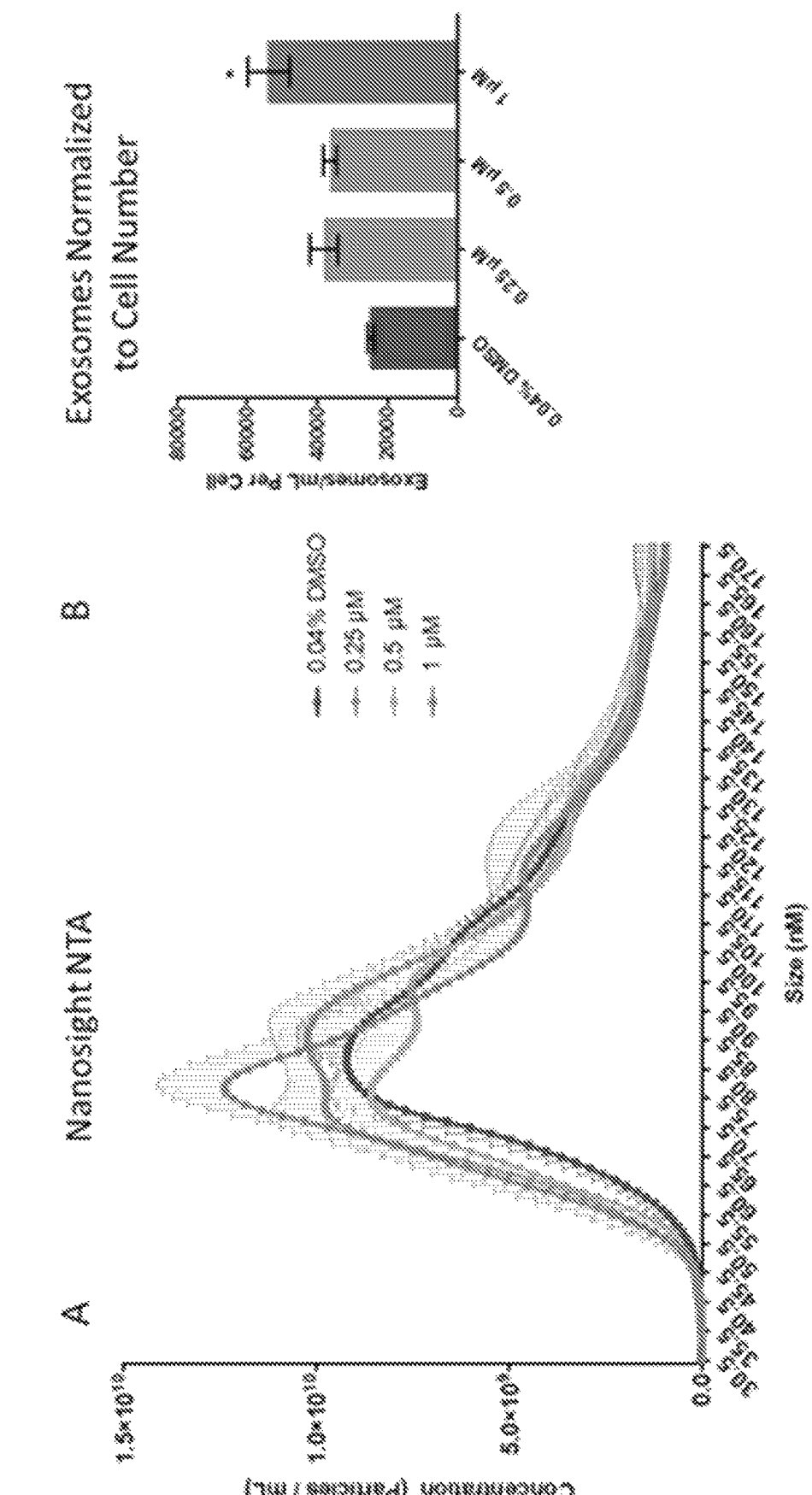
FIG. 3. Benzo[a]pyrene exposure increases exosome production. A, Nanosight NTA analysis of exosomes following 48 h BaP treatment. Mean±SE of four independent experiments. B, Exosome numbers were normalized to post exposure cell number. *Different from DMSO control $p<0.05$. N=4. One-way ANOVA with Dunnet's multiple comparisons.

Following BaP exposure, exosomes were purified from cell media and quantified using Nanosight NTA (FIG. 3A). It was observed that BaP exposure altered the quantity and size distribution of exosomes. Cells exposed to 1 µM BaP produced more exosomes in the 61.5-77.5 nM range and cells exposed to 0.25 µM BaP produced more exosomes in the 64.5-71.5 nM range (2-way ANOVA, Dunnet's multiple comparisons). To control for reductions in cell proliferation and better understand the effects of BaP on exosome production, the number of exosomes (sum of all counted particles between 30-150 nM) was normalized to the total number of cells at the end of exposure. This analysis revealed that the number of exosomes released per cell increased as a result of BaP exposure.

BaP Exposure Increases Exosome LINE-1 mRNA

Figure 4:
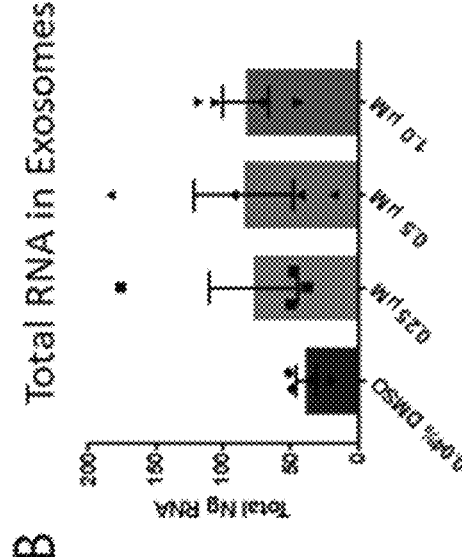
FIG. 4. Effects of benzo[a]pyrene-mediated LINE-1 induction on LINE-1 mRNA levels in cells and exosomes. A, LINE-1 mRNA induction expressed as fold change from B-Actin and DMSO control in cells. B, Total RNA (ng) purified from exosomes. C, As an alternative to B-Actin normalization, qPCR relative fluorescence units (RFU) normalized to cell number was used. D, The relationship between cell and exosome LINE-1 mRNA levels were compared using linear regression.
Figure 4:
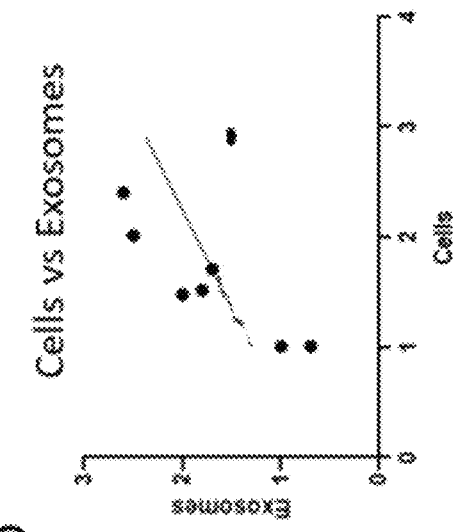
Figure 4:
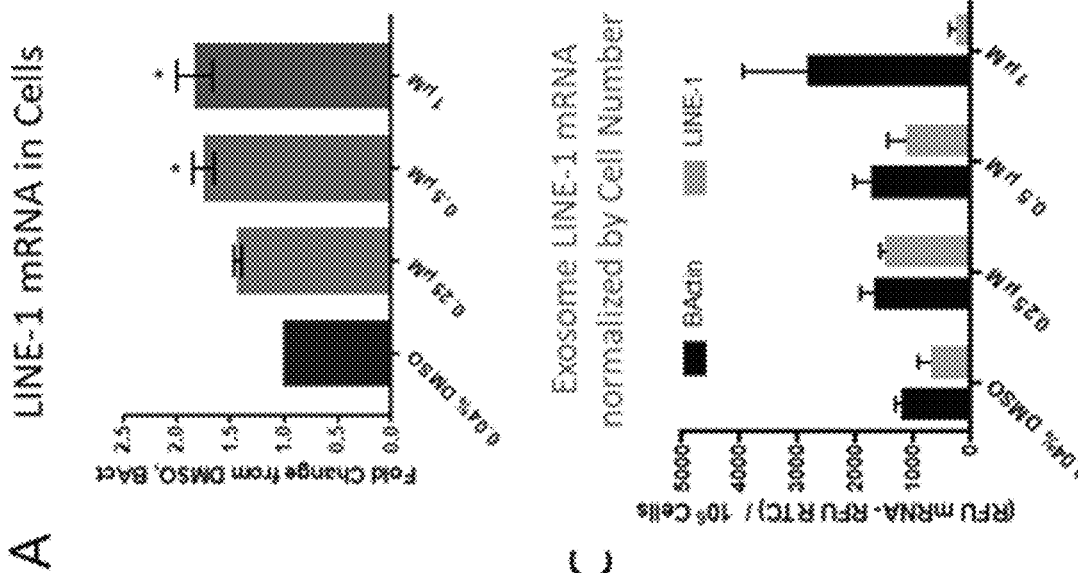
Figure 8:
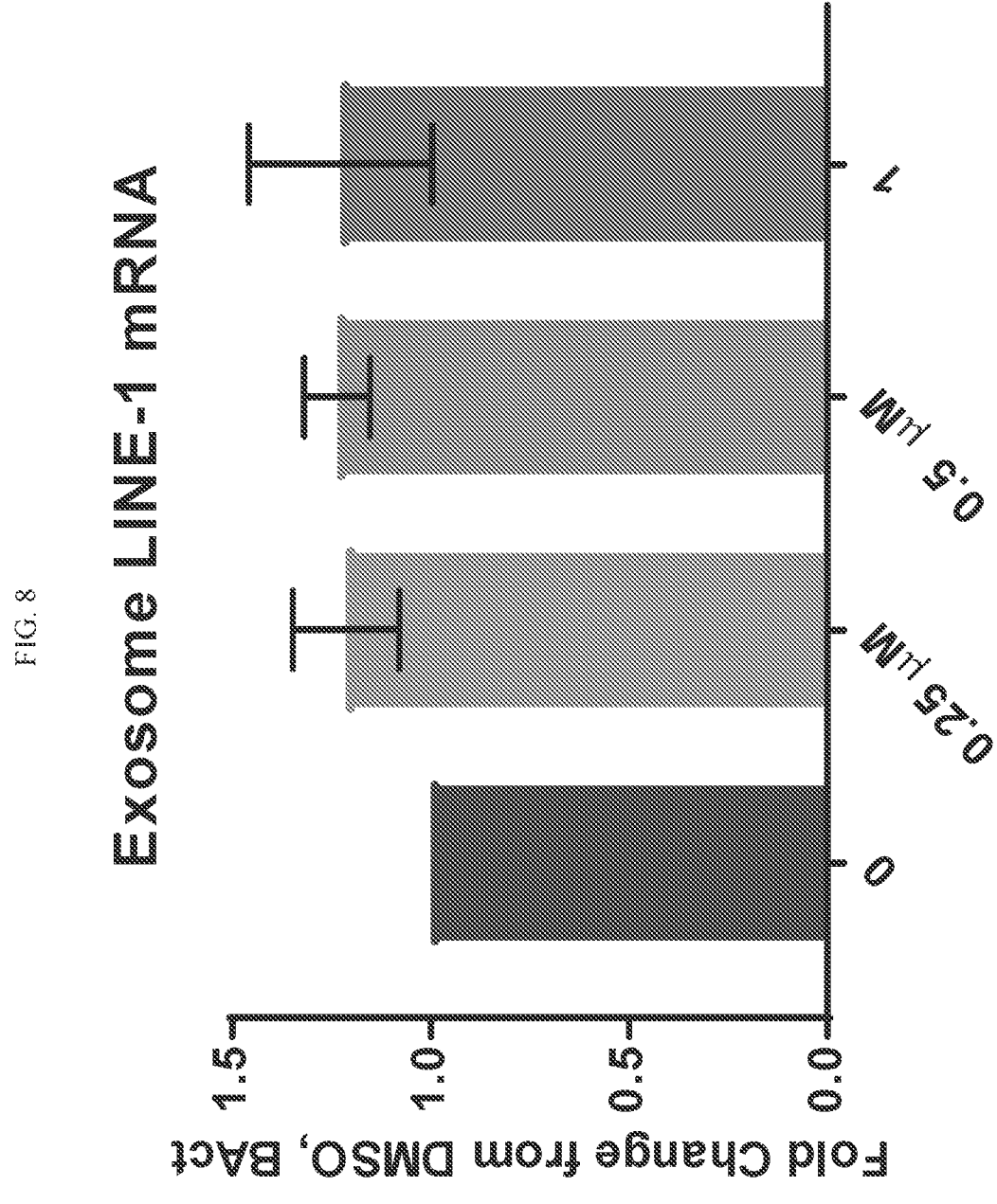
FIG. 8. Exosome LINE-1mRNA normalized to BActin mRNA and DMSO control.

BaP increased cellular levels of LINE-1 mRNA (FIG. 4A) in a dose-dependent manner. Relative to DMSO control, BaP exposure increased LINE-1 mRNA (mean±SE) 1.425±0.04 fold at 0.25 µM, 1.747±0.10 fold at 0.5 µM, and 1.833±0.17 fold at 1 µM, with the 0.5 and 1 µM exposures significantly elevated over control (p<0.05). Exosomes derived from the same BaP exposures were used to determine if the LINE-1 mRNA cargo within these exosomes mirrored cellular patterns. BaP exposure increased the quantity of total exosome RNA (FIG. 4B), from 38±7.16 ng for the DMSO control up to 83.26±16.94 ng at 1 µM BaP. LINE-1 mRNA was examined using the Pfaffl method and normalized to B-Actin mRNA. We did not observe significant increases in LINE-1 mRNA (FIG. 8); however, this approach is not ideal for analyzing exosome cargo, as the output only reflects the ratio of LINE-1 to B-Actin imported into exosomes and does not accurately quantify total LINE-1 mRNA increases in the exosome pool. Moreover it is not possible to correct for BaP-mediated decreases in cell proliferation. Instead, raw fluorescence units were adjusted by cell number as a way to estimate the relative amount of LINE-1 mRNA released per cell in exosomes (FIG. 4C). Using this approach, it was found dose-dependent increases in exosome B-Actin mRNA released per cell, which corresponds with the findings that BaP increases exosome production and total RNA export. LINE-1 mRNA, however, did not follow this trend. BaP increased LINE-1 mRNA export approximately two-fold at 0.25 µM and 0.5 µM, but decreased export at 1 µM. This downturn led to there not being a significant relationship between cell and exosome LINE-1 mRNA at higher BaP concentrations (FIG. 4D). These findings indicate that the regulation and/or loading of LINE-1 mRNA into exosomes may change at different BaP concentrations.

BaP Dose-Dependent Increases of ORFp in Cells and Exosomes

Figure 5:
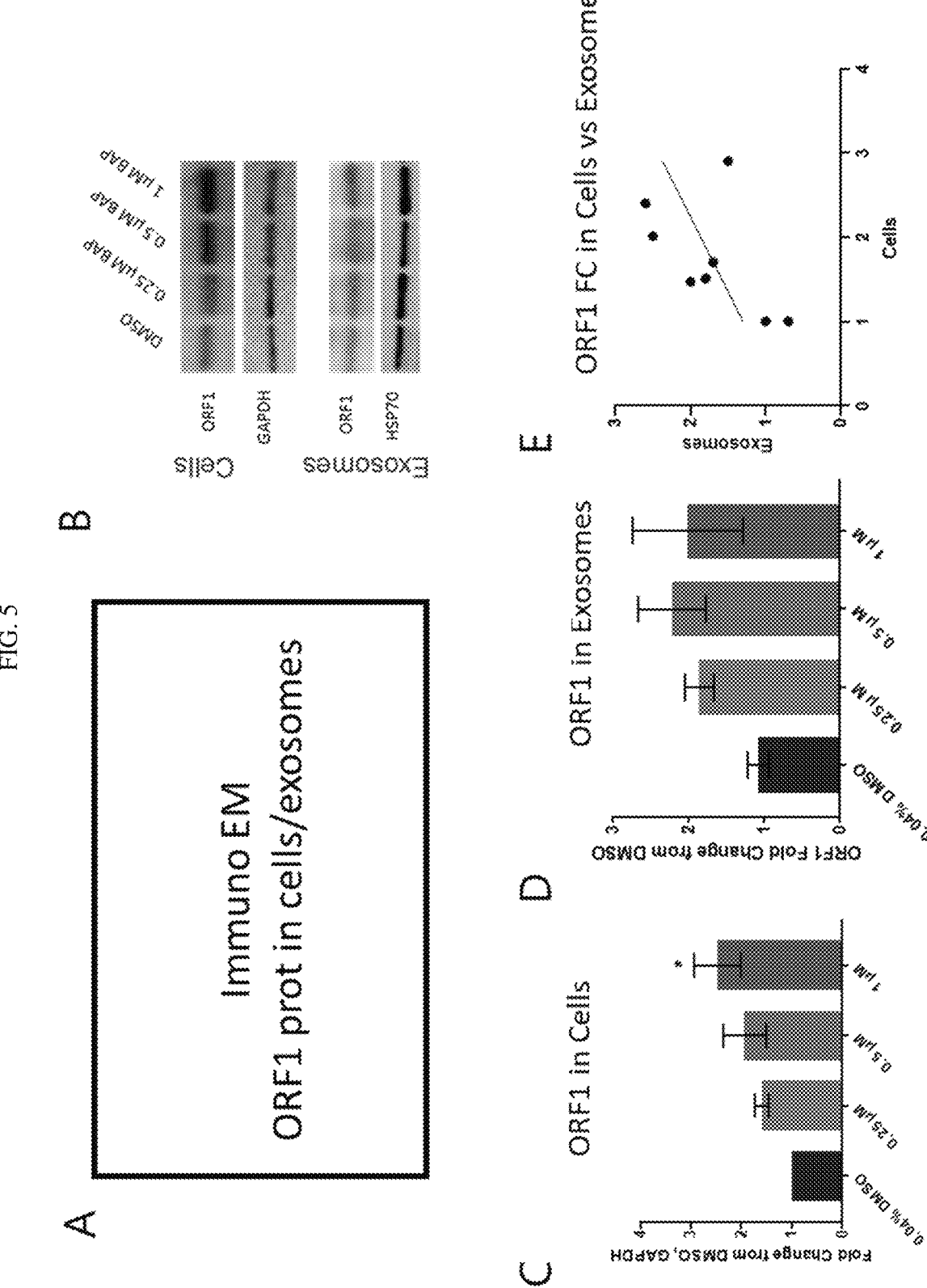
FIG. 5. Effects of benzo[a]pyrene-mediated ORF1 protein induction on ORF1 levels in cells and exosomes. A, Representative Western blot demonstrating increases in ORF1 protein in cells and exosomes. B, Immuno-electron microscopy image of ORF1-labelled protein inside exosomes. Mean ORF1 levels in cells (C) and exosomes (D) averaged over four different Western blots using ImageJ densitometry analysis. E, Linear regression comparing ORF1 fold changes in cells and exosomes. *Different from DMSO control p<0.05. N=4. Kruskal-Wallace non-parametric ANOVA.

Similar to cellular LINE-1 mRNA patterns, BaP exposure also produced dose-dependent increases in ORF1 protein. Relative to DMSO control, BaP exposure increased ORF1 levels (mean±SE) 1.605±0.135 fold at 0.25 µM, 1.935±0.425 fold at 0.5 µM, and 2.47±0.46 fold at 1 µM, with the 1 µM exposure significantly elevated over DMSO control (p<0.05). ORF1 protein was visualized within exosomes using immune electron microscopy (FIG. 5A) and Western blotting (FIG. 5B-D). Similar to cellular levels (FIG. 5C), ORF1p exosome cargo increased in a dose dependent manner (FIG. 5D). Densitometry analysis of ORF1 immunoblots showed that relative to GAPDH and the DMSO control, BaP exposure increased exosome ORF1 (mean±SE) 1.835±0.38 fold in 0.25 µM, 2.295±0.65 fold in 0.5 µM, and 1.90 fold±0.43 in 1 µM treatments. Linear regression analysis (FIG. 5E) indicates that exosome ORF1 levels mirror cellular ORF1 increases.

LINE-1 DNA is Increased in Exosomes

Figure 6:
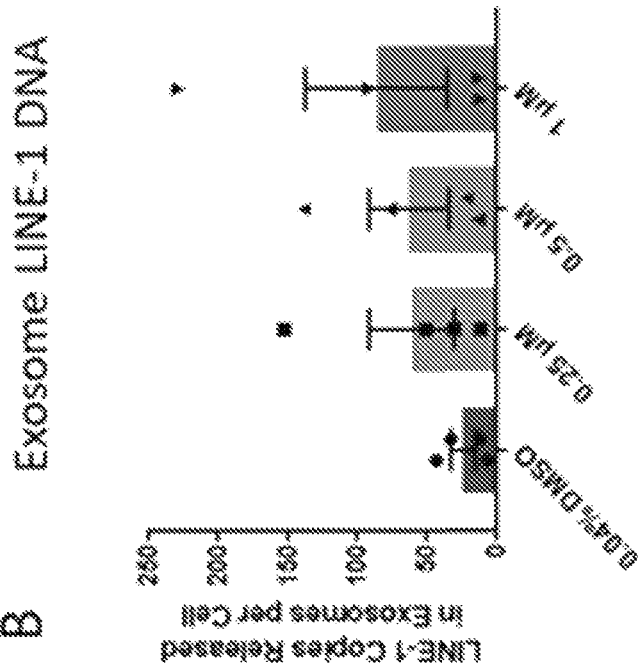
FIG. 6. LINE-1 DNA copy numbers in cells and exosomes following BaP exposure. Absolute qPCR quantification was used to determine the number of copies of LINE-1 DNA in cells (E) and the number of exosome copies per cell (F).

In addition to measures of LINE-1 activation, the amount of LINE-1 DNA present within exosomes was quantified. Using absolute qPCR quantification, the number of LINE-1 copies present were estimated and normalized by cell number. When cellular DNA was analyzed, the method detected approximately 100,000 LINE-1 copies per cell (FIG. 6A), which did not significantly change with BaP exposure. However, when exosome DNA was analyzed (FIG. 6B), it was found that the number of LINE-1 copies released per cell increased. DMSO control exosomes had a mean (±SE) of 23.43±8.6 copies, which increased to 61.04±31.3 in 0.25 µM, 62.43±28.98 in 0.5 µM, and 85.96±51.21 in 1 µM treatments.

LINE-1 Lung Exosome Cargo in Lung Cancer Patients

The aforementioned in vitro findings demonstrate that LINE-1 biomolecules are present within exosomes and that their levels can be used to reveal in situ LINE-1 activation. Studies are performed to determine if lung exosome LINE-1 levels are elevated in lung cancer patients as compared to ostensibly healthy individuals. A technique to immunoisolate lung derived exosomes from plasma based on lung specific proteins is used in combination with Nanosight NTA of exosome counts pulled down from the antibodies described herein. Using the lung specific surfactant proteins, exosomes are isolated from the plasma of 5 patients with lung cancer (previous smokers), 5 healthy previous smokers, 5 healthy current smokers, and 5 never smokers. It is contemplated that lung cancer patients will have elevated numbers of lung exosomes, and that these exosomes contain significantly increased levels of LINE-1 mRNA, protein, and DNA.

Example 2

The majority of LINEs are silenced by DNA methylation and histone covalent modifications (see, Chen L, et al., Breast Cancer Res Treat 136:129-42, 2012; Montoya-Durango D E, et al., Mut Res 665:20, 2009; Teneng I, et al., Epigenetics 6:355, 2011). Although human and mouse LINE-1s exhibit structural differences, benzo (a) pyrene (BaP) mediates transcriptional activation via comparable mechanisms involving disruption of epigenetic silencing, interference with retinoblastoma-regulated macromolecular interactions and downregulation of DNMT1 expression (see, Montoya-Durango D E, et al., Mut Res 665:20, 2009; Teneng I, et al., Epigenetics 6:355, 2011). Several lines of evidence in vitro established the ability of LINE-1 to retrotranspose to new genomic locations where it compromises genome stability through altered gene splicing, disruption of gene function, and increased recombination (see, Beck C R, et al., Cell 141:1159-70, 2010; Faulkner G J, et al., Nat. Genet 41:563-571, 2009; Symer D E, et al., Cell 110:327-338, 2002). LINEs may also control gene expression by providing regulatory sequences that direct expression of other genes (see, Jordan I K, et al., Trends Genet 19:68-72, 2003; Thornburg B G, et al., Gene 365:104-110, 2006). The activity of LINE-1 in vivo has not been widely studied and to date only two active human LINEs, L1RP (see, Carlson C M, et al., Nat Rev Genet 6:568-580, 2005) and L1LRE3 (see, Dupuy A J, et al., Genesis 30:82-88, 2001), have been described. These LINEs exhibit extremely low retrotransposition frequencies when introduced into mice in their native form and genetic manipulation is required to optimize expression (see, An W, et al., Proc Natl Acad Sci USA 103:18662-18667, 2006)

BaP is a byproduct of the incomplete combustion of organic matter (see, Rengarajan T, et al., Asian Pac J Trop Biomed 5:182-189, 2015), and the principal constituent of tobacco smoke implicated in lung carcinogenesis (see, Kasala E R, et al., Pharmacol Rep 67:996-1009, 2015). The parent hydrocarbon and its oxidative metabolites bind to the aryl hydrocarbon receptor (AhR) to induce nuclear translocation and dimerization with the AhR nuclear translocator to form a liganded complex that regulates several genes, including members of the cytochrome (CYP) P450 superfamily (see, Meyer B K, et al., Biochemistry 38:8907-8917, 1999). The relative abundance of CYP and AhR proteins in the lung is high, with CYPs readily catalyzing the conversion of BaP to [(±)-anti-benzo[a]pyrene-7,8-diol-9,10-epoxide] (BPDE) and other metabolites which form the DNA adducts detected in the lung tissue of smokers (see, Moorthy B, et al., Toxicol Sci 145:5-15, 2015). BaP activates LINE-1 expression in various cell types and multiple mammalian species (see, Lu K P, et al., Biochem Biophys Res Commun 253:828-33, 1998; Lu K P, et al., J Biol Chem 278:28201-9, 2003; Teneng I, et al., Epigenetics 6:355, 2011), and AhR signaling participates in the LINE-1 reactivation cascade (see, Teneng I, et al., Genes Cells 12:1101-1110, 2007).

The following experiments were conducted to evaluate profiles of LINE-1 reactivation and genetic reprogramming following genotoxic lung injury by BaP. The ORFeus$^{LSL}$ murine transgenic model containing a single copy of an optimized human LINE-1 transgene was employed to define exogenous activation. It was determined that the genotoxicity of BaP alone or in combination with adenoCRE recombinase was associated with activation of the LINE-1 transgene and a sexually dimorphic profile of genetic reprogramming linked to early oncogenic signaling.

Materials and Methods

Animals

Founder ORFeus$^{LSL}$ mice, a genetically-modified conditional model of LINE-1 retrotransposition under control of CRE recombinase.

Reactivation of ORFeus$^{LSL}$ Transgene by BaP Alone or with adenoCRE Recombinase BaP dissolved in dimethyl sulfoxide (DMSO) was administered via instillation with or without adenoCRE recombinase for conditional activation of a single-copy of a human LINE-1 transgene (see, An W, et. al. Proc Natl Acad Sci USA 103:18662-18667, 2006). A BioLite Intubation System (Braintree Scientific Inc, USA) was used for intratracheal instillation of ORFeus$^{LSL}$ mice (29-38 g) anesthetized with ketamine and xylazine (100 mg/kg and 10 mg/kg, respectively). All mice were genotyped to confirm genetic identity. Control mice were given one dose of $5×10^{10}$ PFU adenoCRE recombinase dissolved in $H_2O$ or DMSO. The optimal adenovirus dose was defined empirically as a dose that only modestly activated the transgene. Treated mice were intubated with BaP (50 mg/kg) alone or in combination with $5 \times 10^{10}$ PFU adenoCRE virus. Mice were sacrificed by cervical dislocation after euthanasia with $CO_2$ one-week after treatment. Tissues were collected and stored at 4° C. in RNA later (Thermo Fisher Scientific, CA).

Histological Analysis

Lung sections were snap-frozen in OCT. Tissues were fixed with cold acetone and stained with hematoxylin and eosin. Samples were evaluated blindly by two pathologists.

32P-Postlabeling

The 32P-postlabeling assay for DNA adducts was performed as reported previously (see, Moorthy B, et al., Arch Toxicol 70:696-703, 1997.

Quantitative Real Time-PCR (RT-qPCR)

RNA was extracted using the RNeasy Plus Mini Kit (Qiagen, MD). An aliquot of 250 ng RNA was reverse transcribed into first-strand cDNA using SuperScript® III adenoCRE seen only in male mice. The occurrence of BPDE-dG DNA adducts one week following carcinogen treatment established persistence of covalent binding following widespread DNA damage. This is significant given that the BaP dose given is well below the total cumulative dose range of 25 to 100 mg/kg administered daily over several months for human toxicological risk assessments (see, Singer M F, et al., Nucleic Acids Res 11:5739-5745, 1983). No dramatic toxic effects were observed at any time in mice treated with BaP alone or in combination with adenoCRE recombinase.

Relative Adduct Labelling (RAL) is equal to the number of adducts per 108 nucleotides. Letters a-f, denote significant differences between and among the different groups by sex*treatment. N=3.

TABLE 1

DNA Adduct Signal Intensity in the Lung of ORFeus$^{L\text{-}SL}$ Mice Following Treatment with Benzo(a)pyrene Alone or in Combination with CRE Recombinase.

| Treatment | DNA Adduct Levels (Mean RAL ± SD) | | | | | |
|---|---|---|---|---|---|---|
| | Adduct 1 | Adduct 2 | Adduct 3 | Adduct 4 | Adduct 5 | Total |
| Untreated Control | $3.50^f \pm 1.91$ | $1.69^{no} \pm 0.88$ | $2.71^j \pm 1.65$ | $1.39^q \pm 0.62$ | $1.68^{no} \pm 0.34$ | $2.19^E \pm 0.82$ |
| CRE/DMSO | $2.82^i \pm 1.95$ | $1.71^n \pm 1.23$ | $1.92^m \pm 0.80$ | $0.84^{uv} \pm 0.35$ | $1.18^s \pm 0.29$ | $1.69^F \pm 0.70$ |
| BaP/F | $28.01^a \pm 17.49$ | $2.95^h \pm 0.99$ | $4.04^e \pm 1.74$ | $1.44^{pq} \pm 0.65$ | $1.40^q \pm 0.83$ | $7.57^A \pm 10.92$ |
| BaP/M | $10.35^d \pm 6.21$ | $1.65^o \pm 0.30$ | $1.48^p \pm 0.78$ | $0.66^w \pm 0.23$ | $1.25^r \pm 0.43$ | $3.08^D \pm 3.78$ |
| Cre/BaP/F | $23.86^b \pm 3.99$ | $2.39^k \pm 0.87$ | $3.10^g \pm 0.66$ | $0.89^k \pm 0.16$ | $1.30^r \pm 0.55$ | $6.31^B \pm 9.12$ |
| Cre/BaP/M | $17.61^c \pm 9.34$ | $1.94^m \pm 0.35$ | $2.29^l \pm 0.51$ | $0.80^v \pm 0.28$ | $1.05^t \pm 0.72$ | $4.73^C \pm 6.68$ |
| Total | $14.36^A \pm 9.89$ | $2.06^B \pm 0.48$ | $2.59^B \pm 0.86$ | $1.0^C \pm 0.30$ | $1.31^C \pm 0.22$ | |

(Invitrogen, CA). RT-qPCR was carried out for LINE-1 and nine genes within its oncogenic regulatory network. These genes included: AhR, Chemokine (C-C motif) ligand 2 (CCL2), Cytochrome P450, family 2, subfamily a, polypeptide 4 (CYP2A4), Microsomal glutathione S-transferase 1 (MGST1), Phenylalanine hydroxylase (PAH), Periostin, osteoblast specific factor (POSTN), Protein tyrosine phosphatase, receptor type, B (PTPRB), Vascular cell adhesion molecule 1 (VCAM1), and Transforming growth factor beta 1 or (TGF-β1) (see, Bojang P, et. al. Mol Oncol 7:812-25, 2013; Ramos K S, et. al. Genomics 90:176-85, 2007). GAPDH was used as a control. Each reaction included 4.0 μL of cDNA, 0.5 μL of gene-specific primer pairs, and 5.0 μL SyberGreen dye and ddH2O to a final volume of 20 μL. Amplifications were completed using StepOnePlus™ RT-qPCR System and fold changes calculated using $2^{-\Delta\Delta ct}$.

Statistical Analyses

All normally distributed data were analyzed by ANOVA and Duncan's Multiple Range Test. Non-normally distributed data were evaluated using the Mann-Whitney U test. Significance was defined at the P≤0.05 level.

Results

Figure 9:
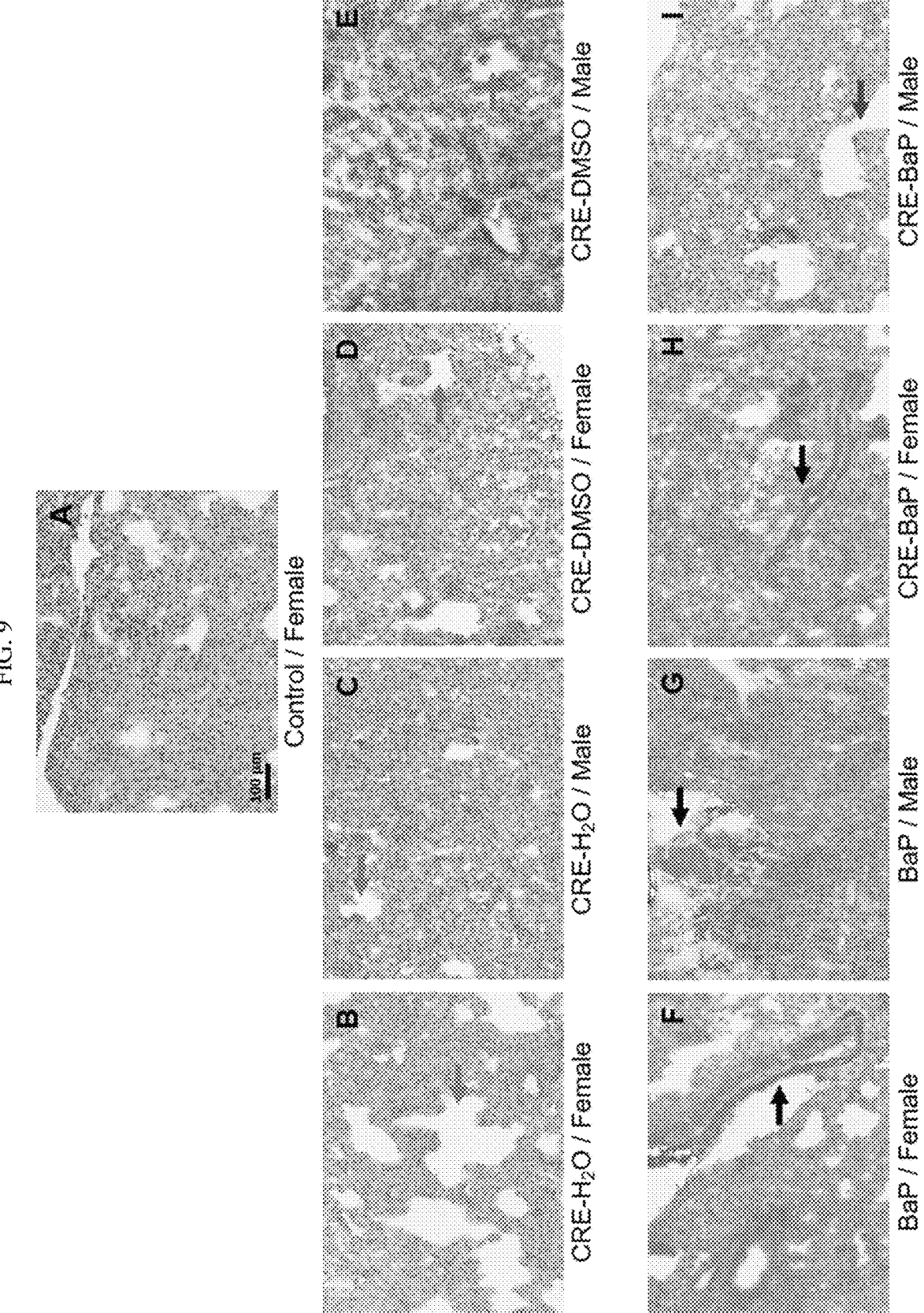
FIG. 9: Histology of Lung Tissues in ORFeus$^{LSL}$ Mice Treated with Benzo (a) pyrene Alone or in Combination with CRE Recombinase. A-I show representative results for all treatment groups at 40×. Blue arrows indicate the pulmonary edema evidenced by vascular dilation, black arrows denote pulmonary vessel congestion and red arrow denote emphysematous changes evidenced by large empty spaces with variable preservation of alveolar structures. N=3.
Figure 9:
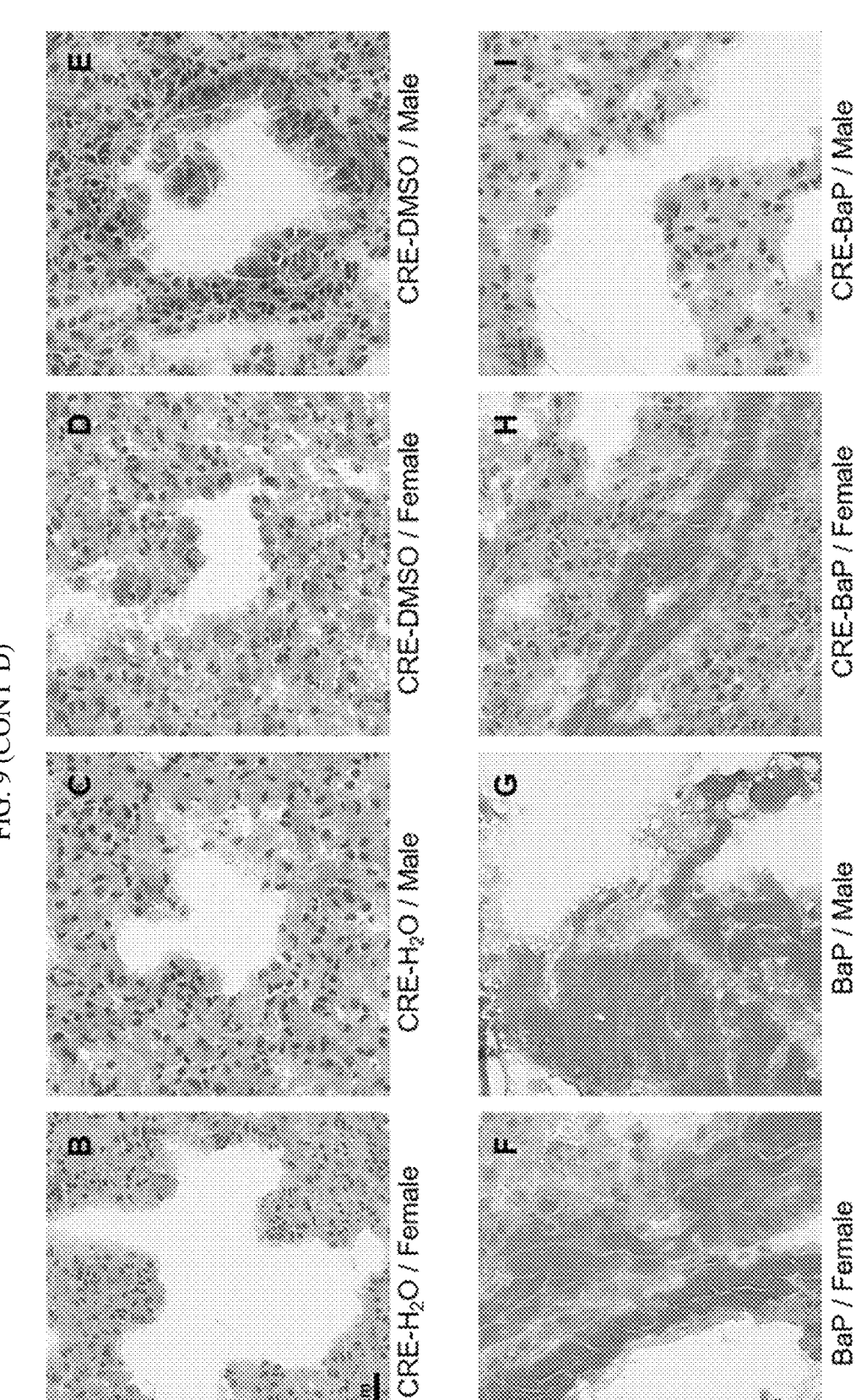

BPDE-deoxy guanine (dG) DNA adducts were detected in the lungs of both female and male ORFeus$^{L\text{-}SL}$ mice given a single dose of 25 mg/kg BaP alone or in combination with adenoCRE (Table 1). Only background signal was detected in control untreated, CRE/H2O or CRE/DMSO mice. All major adducts were derived from BPDE, as evidenced by autoradiographic signals (see, Arif J M, et al, Chem Biol Interact 118:87-97, 1999; Banasiwicz M, et al., Anal Biochem 334:390-400, 2004). Adduct intensities were considerably higher in female mice compared to males, with significant differences between BaP alone and BaP plus Control lung tissues from mice given water or DMSO alone, or in combination with adenoCRE recombinase, showed normal histology, except for a modest degree of iatrogenic pulmonary edema evidenced by vascular dilation (FIG. 9, A-E). In contrast, significant leukocytic infiltration into the lungs was prominent in mice given BaP alone or combined with adenoCRE. Female and male mice in both treatment groups showed pulmonary vessel congestion with focal-to-diffuse mononuclear cell infiltration into parenchyma. Lung tissues also showed emphysematous changes evidenced by large empty spaces with variable preservation of alveolar structures (FIG. 9, F-I).

Figure 10A:
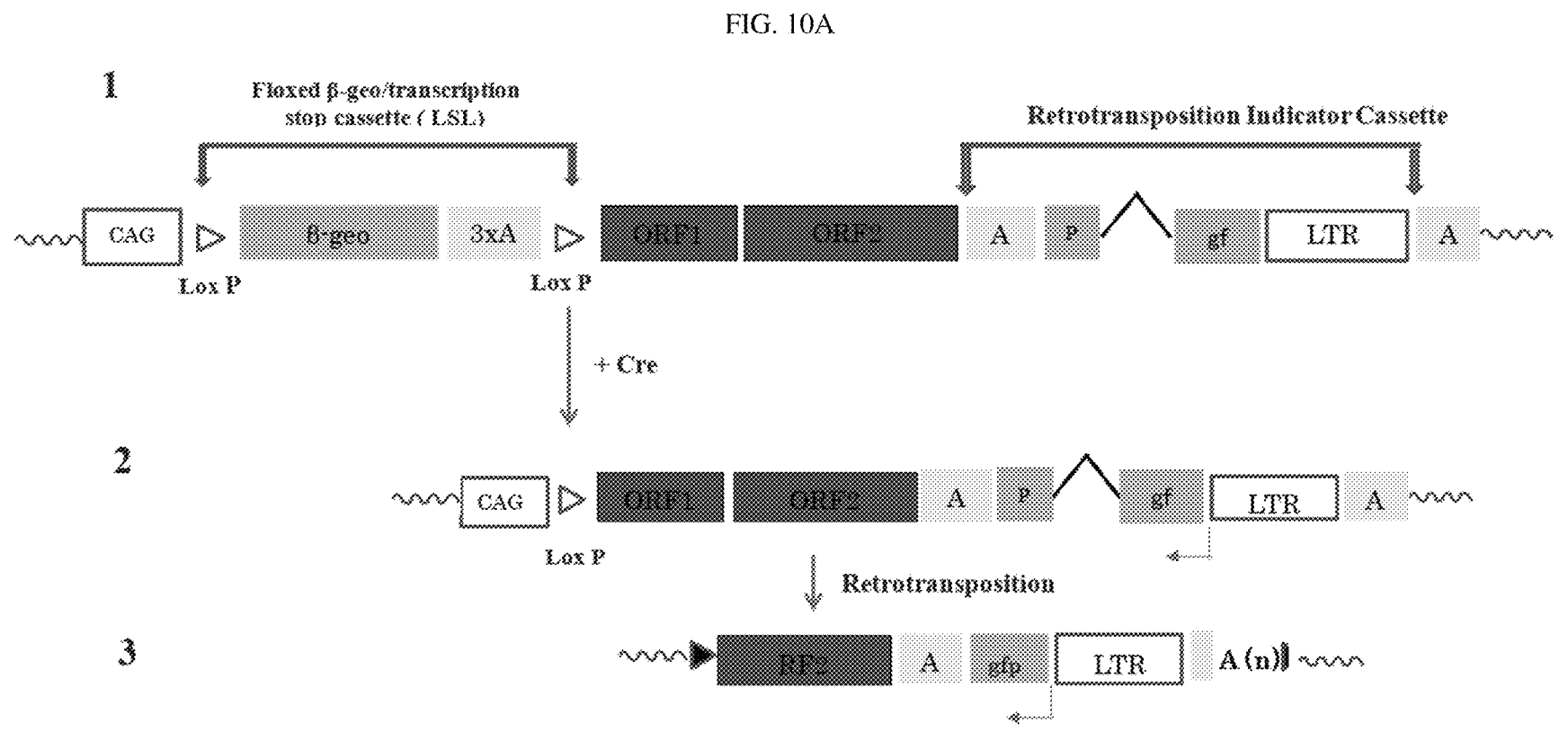
Figure 10B:
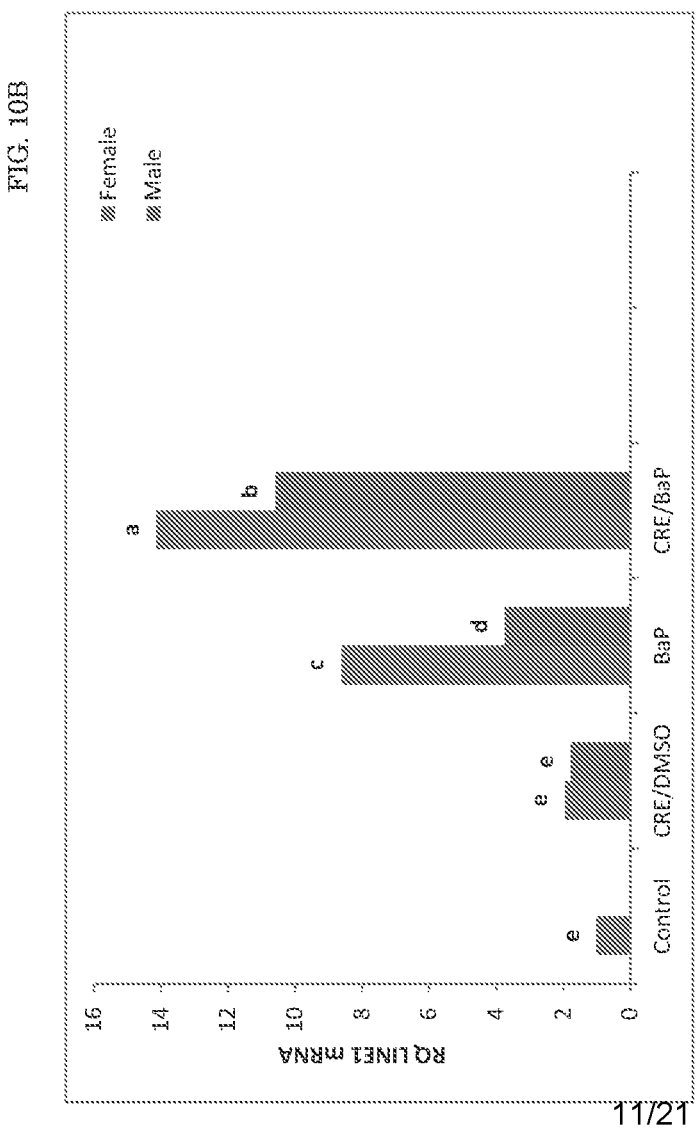
FIG. 10: A. Schematic of the ORFeus$^{LSL}$ Transgene. 1) The floxed allele of the ORFeus$^{LSL}$ transgene. 2) The excised allele of the ORFeus$^{LSL}$ transgene following Cre-mediated excision of the floxed β-geo/stop cassette. 3) Putative insertion upon retrotransposition. Arrows 1 and 2 denote the positions of forward and reverse primers in RT-qPCR. B: LINE-1 mRNA in Lungs of ORFeus$^{LSL}$ Mice Treated with Benzo (a) pyrene Alone or in Combination with CRE Recombinase. LINE-1 mRNA was measured by RT-qPCR using primers specific for ORFeus$^{LSL}$. Different letters denote differences between control, BaP and CRE-BaP treated groups at P≤0.05. N=3.

Measurements of ORFeus LINE-1 mRNA were completed to evaluate the ability of the carcinogen to activate the human transgene. A schematic of the ORFeus$^{L\text{-}SL}$ transgene under control by LoxP is presented in FIG. 10A. BaP alone significantly increased expression of the transgene, while adenoCRE recombinase alone was only modestly active. Increased expression of ORFeus LINE-1 mRNA was observed in both male and female lungs given the combined BaP/adenoCRE treatment compared to BaP alone or vehicles. In keeping with patterns of DNA adduct formation and tissue damage, ORFeus LINE-1 mRNA levels were higher in female lungs compared to male lungs (FIG. 10B). The specificity of the lung induction response was confirmed in studies showing that only stomach, but not heart, kidney, liver or intestine, showed activation of the LINE-1 transgene and that BaP treatment induced CYP gene expression in the lungs of ORFeus mice.

Figure 11:
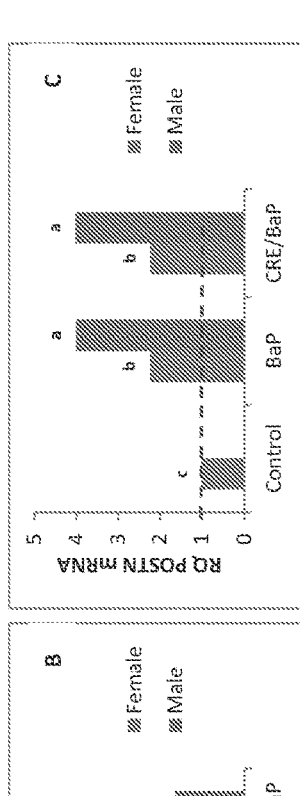
FIG. 11: mRNA Abundance of Genes Within the LINE-1 Oncogenic Regulatory Network in Lungs of ORFeus$^{LSL}$ Mice. Panels A-I show the results for different genes within the network. Different letters denote differences between control, BaP and CRE-BaP treated groups at P≤0.05. N=3.
Figure 11:
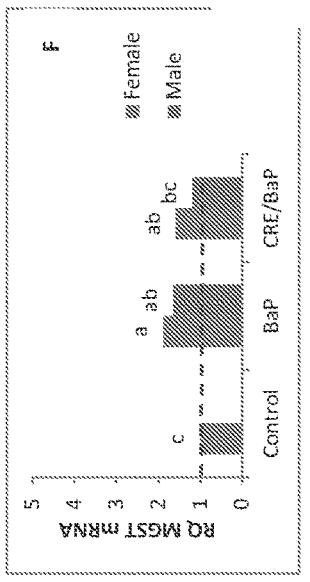
Figure 11:
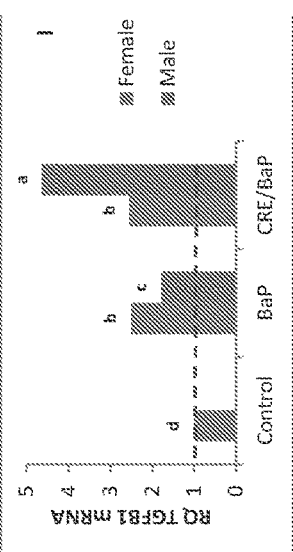
Figure 11:
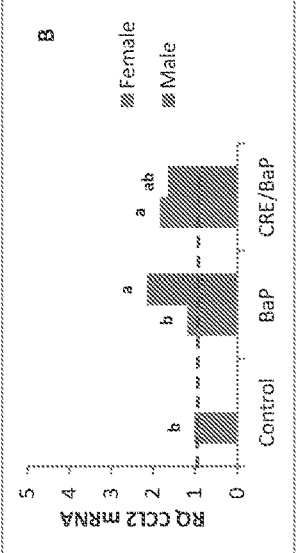
Figure 11:
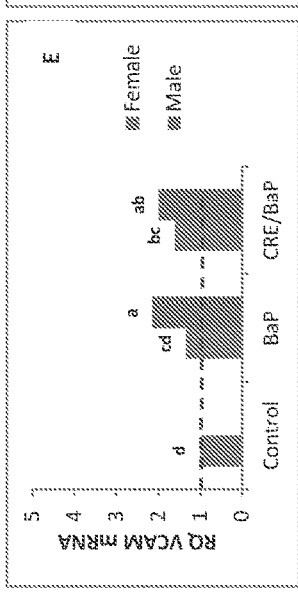
Figure 11:
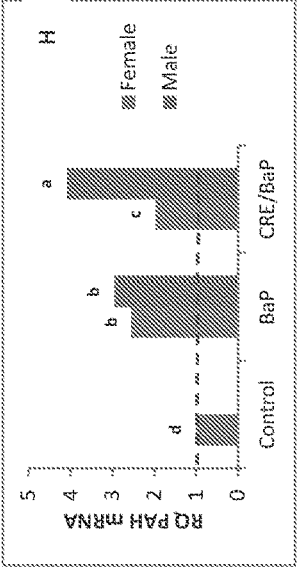
Figure 11:
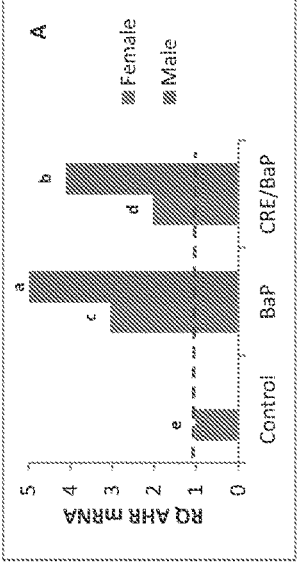
Figure 11:
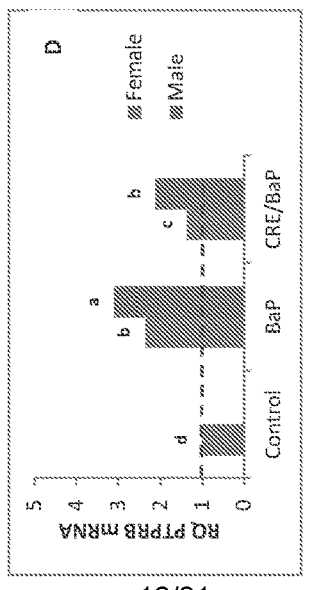
Figure 11:
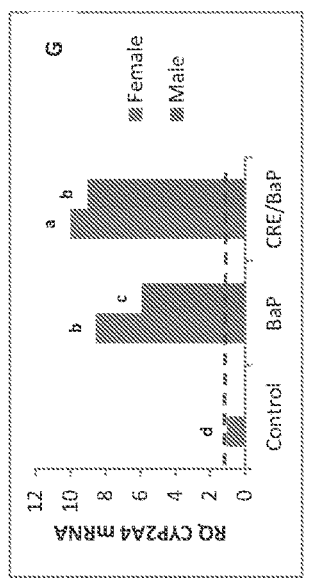

To investigate the biological consequences of LINE-1 activation in the lungs of ORFeus mice, experiments were next conducted that examined genes within a LINE-1 regulatory network that is activated during oncogenic reprogramming of epithelial genomes (see, Ramos K S, et al., Genomics 90:176-85, 2007; Bojang P, et al., Mol Oncol 7:812-25, 2013). The targets chosen constitute a regulatory network involved in early oncogenic signaling and included Aryl hydrocarbon receptor (AhR), Chemokine (C-C motif) ligand 2 (CCL2), Cytochrome P450, family 2, subfamily a, polypeptide 4 (CYP2A4), Microsomal glutathione S-transferase 1 (MGST1), Phenylalanine hydroxylase (PAH), periostin, osteoblast specific factor (POSTN), Protein tyrosine phosphatase, receptor type, B (PTPRB), Vascular cell adhesion molecule 1 (VCAM1), and Transforming growth factor beta 1 or (TGF-β1) were examined. These genes were differentially regulated upon activation of the LINE-1 transgene, with notable differences between BaP alone or in combination with adenoCRE seen for all, but POSTN and PTPRB (FIG. 11, A-I). All mice were of comparable age to obviate potential age-related differences. Thus, induction of ORFeus LINE-I was associated with genetic reprogramming in the murine lung in vivo, and this response was sustained for up to one week after carcinogen treatment.

Discussion

BaP is a pro-carcinogen metabolized by CYP1A1 and CYP1B1 to highly reactive electrophilic intermediates (see, Gelboin H V, Physiol Rev 60:1107-66, 1980; Kang Z C, et al., Nutr Cancer 35:175-9, 1999). This metabolic activation mediates DNA adduct formation, including those associated with BPDE, the primary lung cancer etiologic agent (see, Kapitulnik J, et al., Cancer Res 38:354-8, 1978; Shiizaki K, et al., Genes Environ 39:14, 2017). The total cumulative dose of BaP examined in our study approximates the cumulative dose experienced by a smoker consuming 40 cigarettes per day for two-years. This is significant given that one year in the life of a human is equivalent to nine days in the mouse (see, Dutta S, et al., Life Sci 52:244-248, 2016). As such, such findings reflect early changes associated with activation of the LINE-1 retrotransposon and genetic elements within its oncogenic regulatory network.

BaP is rapidly distributed throughout the body and detected in most tissues within minutes to hours after exposure. DNA adduction, a key event in the mutagenic and carcinogenic response, appears as early as four hours after dosing of mice with the parent hydrocarbon (see, Ginsberg G L, et al., Cancer Res 50:1189-1194, 1990). Such results represent evidence for the first time that the genotoxic response of the mouse lung to BaP in vivo involves sustained activation of LINE-1 retrotransposon and this response exhibits a sexually dimorphic profile. These findings impact the current understanding of tobacco-induced carcinogenesis.

Sex differences in BaP metabolism and DNA repair capacity have been documented (see, Shigematsu H, et al., J Natl Cancer Inst 97:339-46, 2005), with several studies indicating that relative lung cancer risk among females exceeds that of males by 2.5-fold (see, Zang E A, et al., J Natl Cancer Inst, 88:183-92, 1996; Risch H A, et al., Am J Epidemiol 138:281-93, 1993; Henschke C I, et al., Lung Cancer 43:1-5, 2004). In these experiments, the levels of BaP-DNA adducts were higher in the lungs of female mice compared to males, a finding consistent with the enhanced female susceptibility to tobacco carcinogens and sex-related differences in CYP gene expression between women and men (see, Haugen A. Carcinogenesis 23:227-229, 2002; Mollerup S, et al., Int. J. Cancer 119:741-744, 2006). Increased lung cancer susceptibility in females may also be strongly influenced by interactions between estrogen receptors and proteins involved in the regulation of hydrocarbon metabolism (see, Feng Q, et al., Cell 87:905-916, 1996). Estrogen receptors are expressed in normal lung tissue as well as tumors (see, Baik C S, et al., Cancers 4:969-988, 2012), and strongly implicated in lung development (see, Hsu L-H, et al., Int. J Mol. Sci 18:1713, 2017).

In most human and rodent somatic cells, LINEs are silenced epigenetically via DNA methylation, a process that functions in tandem with LINE-1 deamination by APOBEC proteins, the degradation of LINE-1 mRNA by TREX1 exonuclease and Piwi-interacting RNAs, and transcriptional repression by epigenetic modifying proteins (see, Khalid M, et al., Mut Res Rev 778:51-60, 2018). As such, activation of a LINE-1 transgene engineered to operate under the regulatory control of CRE recombinase in vivo provides compelling evidence that BaP overrides regulatory control to persistently activate LINE-1 transcription and to activate its genetic regulatory network. Given the potentially devastating consequences of LINE-1 reactivation, these findings suggest that LINE-1 and genes within its oncogenic regulatory network play a major role in the lung pathologic response to tobacco carcinogens. While the degree to which transcriptional activation of LINE-1 and/or retrotransposition couples with DNA damage in vivo to modulate carcinogenesis requires further investigation, LINE-1 is associated with insertion mutations, genetic deletions and reprogramming of epithelial differentiation (see, Khalid M, et al., Mut Res Rev 778:51-60, 2018). As such, the observed responses in vivo raise important questions about the contributions of retrotransposition-dependent and -independent mechanisms to BaP carcinogenesis in vivo. In accord, oncogenic transformation is associated with elevated LINE-1 expression in human lung tumors in the absence of changes in neighboring tissues (see, Rangasamy D, et al., Current Molecular Medicine 15:588-597, 2015).

Previous experiments discretized a LINE-1 genetic regulatory network that is linked to host regulation of LINE-1 and oncogenic signaling (see, Bojang P, et al., Mol Oncol 7:812-25, 2013; Ramos K S, et al., Genomics 90:176-85, 2007). In vivo validation of the functional integrity of this regulatory network in the lung of ORFeus mice indicates that genes within the network are involved in the acute and adaptive responses of the lung to BaP. For instance, AhR-dependent genetic regulation of lung tissue has been associated with inflammation, DNA-adduct, EMT and tumorigenesis (see, Ikuta T, et al., Exp. Cell Res 312:3585-3594, 2006; Lin P, et al., Lung Cancer 42:255-261, 2003; Tsay J J, et al., Anticancer Res 33:1247-56, 2013). The diffuse infiltration of mononuclear cells in BaP-treated lung tissue is consistent with the upregulation of CCL2, a major chemoattractant involved in leukocyte homing to sites of inflammation (see, Liu X, et al., Am J Resp Cell Mol Biol 37, 2007). The upregulated expression of MGST1 and CYP2A4 is often secondary to disruption of cellular defenses by electrophilic compounds through conjugation of reduced glutathione and compensatory feedback control (see, Nebert D W, et al., Hum Genomics 1:460-464, 2004). BaP induces genes involved in epithelial reprogramming such as POSTN (see, Yoshino I, et al., Cancer 110:369-374, 2007) and PTPRB, the latter being a protein tyrosine phosphatase involved in oncogenic transformation (see, Du Y, et al., Chin J Cancer 34:61-69, 2015). VCAM-1, a member of the immunoglobulin superfamily (see, Zhang D, et al., Neurochem Res 40:1042-52, 2015), is elevated in idiopathic pulmonary fibrosis by TGF-β1 (see, Agassandian M, et al., Cell Signal 27:2467-2473, 2015), a known inducer of epithelial dedifferentiation (see, Pickup M, et al., Nat Rev Cancer 13:788-799, 2013). Thus, these findings advance an understanding of the role of LINE-1 during the early stages of oncogenic signaling activated by tobacco lung carcinogens in vivo and provide a platform for evaluation of treatment modalities for precision management of thoracic malignancies.

Example 3

This example demonstrates the characterization of extracellular vesicle LINE-1 mRNA, protein, and reverse transcriptase activity profiles.

LINE-1 mRNA and protein are present in EVs isolated from H460 lung cancer cells and human plasma and are segregated into distinct EV populations. Because reverse transcription (RT) of LINE-1 requires formation of a ribonucleoprotein complex containing LINE-1 mRNA and proteins, it was hypothesized that this segregation has been engineered to control RT. In support of this hypothesis, it was found that RT activity is only present when these two EV populations are lysed and combined. Experiments were next conducted that isolated EVs from ostensibly healthy plasma donors and found substantial inter-individual variability with respect to LINE-1 protein, mRNA, and RT activity. The variability between individuals and the ease of measurement from clinical samples further supports the use of these LINE-1 metrics as health-related biomarkers. After characterizing EV LINE-1, experiments were next conducted that sought to determine whether EV LINE-1 levels could serve as a proxy of cellular LINE-1 content, which is critical to an overall goal of using isolated lung EVs as a liquid biopsy of the lung epithelium. Using a panel of six different lung epithelial cell lines, baseline LINE-1 expression between cells and EVs were compared. Experiments were conducted that also treated lung epithelial cells with different concentrations of benzo (a) pyrene (BaP), a cigarette smoke carcinogen known to induce LINE-1, and compared LINE-1 levels in cells and EVs. It was discovered that, in both baseline and toxicant-induced scenarios, EV LINE-1 mRNA levels mirror cellular levels. Together, these data demonstrate that EV LINE-1 content and RT activity can be quantified in cultured cells and clinical samples and supports the use of EV LINE-1 cargo as a biomarker of lung epithelial cell status.

Example 4

RNA binding proteins, reverse transcriptase and endonuclease alter the host genome via mutational insertions, chromosomal rearrangements and reprogramming of gene expression (see, Ramos K S, et al., Environmental Epigenomics in Health and Disease: Epigenetics and Disease Origins. Heidelberg, Springer, 2013; pp. 127-160). Full-length LINE-1 sequences encode two proteins: ORF-1p, a 40-kDa protein with nucleic acid binding activity; and ORF2p, a 150-kDa protein with endonuclease and reverse transcriptase activities. The activity of LINE-1 is repressed in somatic tissues via DNA methylation and covalent protein modifications and reactivated by displacement of retinoblastoma-associated proteins from the regulatory region (see. Bojang P. Jr., et al., Mol Oncol 2018; 12:1342-1357). Recent studies have implicated LINE-1 as a master regulator of human bronchial epithelial cell phenotypes in experimental in vitro and in vivo models (see, Reyes-Reyes E M. et al., Oncotarget 2017; 8:103828-103842).

Methylation profiles of LINE-I have been linked to cancer and other chronic diseases related to smoking (see, Imperatori A, et al., Lung Cancer 2017; 108:83-89), and a previous report from the Normative Aging Study (see. Lange N E, et al., BMJ Open 2012; 2: e001231) found LINE-1 hypomethylation to be associated with faster decline of both forced expiratory volume in 1 s ($FEV_1$) and forced vital capacity (FVC) among 301 adult participants, the majority of whom were former smokers. However, it is not yet known if the expression of proteins encoded by LINE-1 is upregulated in cases of impaired lung function or COPD. The aim of this study was to determine the association between circulating levels of L1-ORF1p, lung function and airflow limitation in the Tucson Epidemiological Study of Airway Obstructive Disease (TESAOD).

TESAOD is a population-based cohort study of non-Hispanic white households in Tucson, AZ, USA (see, Lebowitz M D, et al., Am J Epidemiol 1975; 102:137-152). Briefly, at enrollment in 1972-1973, participants completed standardized respiratory questionnaires and spirometric lung function tests according to methods previously described (see, Knudson R. J. et al., Am Rev Respir Dis 1976; 113:587-600). For the present study, data from the enrollment survey on $FEV_1$, FVC and $FEV_1$/FVC was used. Percent predicted values for lung function indices were computed using reference equations generated from the same population by Knudson (see, Knudson R J, et al., Am Rev Respir Dis 1983; 127:725-734). Airflow limitation was defined both as a fixed cut-off of $FEV_1$/FVC<70% and, to control for differences by sex and age, as $FEV_1$/FVC below the lower limit of normal (LLN) (see, Pellegrino R, et al., Eur Respir J 2005; 26:948-968).

Blood samples were collected at enrollment, processed into serum and cryopreserved at $-80°$ C. For this study, a subgroup of 427 participants were selected who, at enrollment, were 35-70 years old, completed questionnaires and lung function tests, and had sufficient serum volumes. Serum concentrations of L1-ORF1p were measured using an ELISA. A custom polyclonal anti-human L1-ORF1p antibody was produced by New England Peptide LLC (Gardner, MA, USA). The antigen peptide MGKKQNRKTGNSKTQ (SEQ ID NO:1) used to generate a rabbit polyclonal does not match the murine ORF1p amino acid sequence. The specificity of the antibody was validated using several criteria including a single band of the expected molecular weight by Western blotting, specific knockdown of signal intensity using small interfering RNAs and high reproducibility. Biochemical validation of the anti-L1-ORF1p has been described previously (see, Reyes-Reyes E M, et al., Oncotarget 2017; 8:103828-103842). The antibody was diluted one in 1000 for use in all experiments. Goat anti-rabbit whole-molecule immunoglobulin conjugated to horseradish peroxidase (Sigma-Aldrich, St Louis, MO. USA) was used as secondary antibody. Serum samples were analyzed on six different runs using 96-well microplates.

In statistical analyses, experiments tested the association of L1-ORF1p with lung function indices and with the presence of airflow limitation using L1-ORF1p levels both on a continuous scale (after standardisation so that estimates would represent effects by 1-SD increase) and as quartiles to evaluate nonlinear effects. Because plate effects explained up to 20% of the variability in L1-ORF1p levels, we used mixed-effects models with plate number fitted as a random effect to control for interplate variability. Random-effects models were used for analyses of $FEV_1$, FVC and $FEV_1$/FVC, and multilevel mixed-effects logistic regression models were used for analyses on airflow limitation. Models were adjusted for sex, age, body mass index (BMI), smoking status and pack-years because these factors may be related to both L1-ORF1p and lung function and, in turn, act as confounders.

The 427 participants had a mean age of 55 years and a mean BMI of 24.8 kg·m⁻². They were largely represented by females (284 out of 427, 67%) and smokers (249 out of 427, 58%), with a mean value of 30 pack-years among smokers. 35 participants (8%) reported physician-confirmed active asthma. The mean±SD L1-ORF1p serum concentration was 46±+26 ng·mL⁻¹. L1-ORF1p levels were higher in males than females (51 versus 44 ng·mL⁻¹, p=0.01). Smokers had borderline higher L1-ORF1p levels than never-smokers (48 versus 44 ng·mL⁻¹, p=0.09), with former (50 ng·mL⁻¹) rather than current (46 ng·mL⁻¹) smokers having the highest levels, Although participants with active asthma tended to have higher levels than participants without active asthma (52 versus 46 ng·mL⁻¹, p=0.16), this association was not statistically significant. L1-ORF1p levels were not associated with age or BMI.

Table 2 summarizes the results of analyses of lung function. In adjusted models of the total study population, significant associations between L1-ORF1p serum levels and any of the lung function indices were not identified, although a trend was observed for airflow limitation. When analyses were stratified by smoking status, however, we observed consistent associations among smokers, which were largely driven by the group of former smokers. In this group, each 1-SD increase in L1-ORF1p was associated with a reduction of 7.1% in $FEV_1$ (p<0.001), 5.5% in FVC (p=0.001) and 2.3% in $FEV_1$/FVC (p=0.009), and with a two-fold increased risk of airflow limitation (p=0.014 for $FEV_1$/FVC<70% and p=0.003 for $FEV_1$/FVC<LLN). In contrast, no consistent relations of L1-ORF1p to lung function and airflow limitation were observed among never-smokers. Interaction terms between L1-ORF1p and smoking status were significant for $FEV_1$ (p<0.001) and FVC (p<0.001), and borderline for $FEV_1$/FVC (p=0.09).

(p=0.002), FVC deficits of 14% (p=0.009) and a 10-fold increased risk for $FEV_1$/FVC<70% (p=0.053) as compared with participants in the lowest quartile.

The reasons why, in these experiments, serum L1-ORF1p was associated with lung function impairment only among former smokers are unclear at this time, but these effects are unlikely to be due to previous pulmonary infections or conditions that may have led participants to quit smoking because we did not observe differences in serum L1-ORF1p by history of pneumonia and/or chronic bronchitis either in the total population or among smokers (data not shown). Chemicals present in tobacco smoke, such a benzopyrene, reactivate LINE-1 (see, Reyes-Reyes E M, et al., Am J Cancer Res 2016; 6:1066-1077) and persistent upregulation of L1-ORFs after smoking cessation may be an indicator of long-term susceptibility to cigarette smoking-induced genomic injury. Indeed, smoking cessation does not resolve airway and systemic inflammation in a proportion of former smokers who remain at increased risk of inception and progression of COPD for years after quitting (see, Hogg J C, Thorax 2006; 61:96-97; Miller M, et al., Chest 2011; 139: 1380-1387). In this context, two observations are noteworthy. First, because the distribution by sex was strongly associated with smoking status in our study (the proportion of males was 35%, 57% and 16% among current, former and never-smokers, respectively), one cannot exclude that these effect modifications are related to sex instead of (or in addition to) smoking status itself. Second, in this study, L1-ORF1p effects in former smokers diverged mainly from those of never-smokers, and significant associations between L1-ORF1p and lung function were also present among ever-smokers (i.e. former and current smokers combined). Thus, larger studies will be required to determine conclusively the interrelationship between sex and smoking

TABLE 2

| | $FEV_1$ % predicted | | FVC % predicted | | $FEV_1$/FVC | | Airflow limitation | | | |
| | | | | | | | $FEV_1$/FVC <70% | | $FEV_1$/FVC <LLN | |
| | Adjusted coefficient (95% CI) | p-value | Adjusted coefficient (95% CI) | p-value | Adjusted coefficient (95% CI) | p-value | Adjusted OR (95% CI) | p-value | Adjusted OR (95% CI) | p-value |
|---|---|---|---|---|---|---|---|---|---|---|
| All subjects[#] (n = 418) | −1.50 (−3.28, 0.29) | 0.100 | −0.58 (−2.25, 1.09) | 0.499 | −0.83 (−1.75, 0.08) | 0.074 | 1.26 (0.93, 1.73) | 0.140 | 1.36 (1.00, 1.85) | 0.053 |
| Never-smokers[¶] (n = 176) | 2.19 (−0.63, 5.00) | 0.127 | 2.66 (−0.18, 5.50) | 0.067 | −0.24 (−1.62, 1.13) | 0.727 | 1.02 (0.49, 2.11) | 0.958 | 1.20 (0.58, 2.47) | 0.618 |
| Ever-smokers[#] (n = 242) | −3.36 (−5.65, −1.07) | 0.004 | −2.40 (−4.47, −0.33) | 0.023 | −1.33 (−2.49, −0.18) | 0.024 | 1.31 (0.93, 1.84) | 0.124 | 1.40 (1.01, 1.96) | 0.046 |
| Former smokers[+] (n = 123) | −7.09 (−10.66, −3.51) | <0.001 | −5.50 (−8.87, −2.13) | 0.001 | −2.31 (−4.04, −0.58) | 0.009 | 1.91 (1.14, 3.19) | 0.014 | 2.12 (1.29, 3.47) | 0.003 |
| Current smokers[+] (n = 119) | 0.21 (−2.51, 2.93) | 0.880 | 0.92 (−1.45, 3.30) | 0.446 | −0.08 (−1.67, 1.51) | 0.919 | 1.00 (0.59, 1.70) | 0.991 | 1.15 (0.71, 1.85) | 0.571 |

Body mass index (BMI) information was missing for nine participants (two never-, three former and four current smokers). Airflow limitation was present among 67 and 56 participants when defined by forced expiratory volume in 1 s ($FEV_1$)/forced vital capacity (FVC) <70% and below the lower limit of normal (LLN), respectively.
[#]models adjusted for sex, age, BMI, smoking status and pack-years;
[¶]models adjusted for sex, age and BMI;
[+]models adjusted for sex, age, BMI, and pack-years.

Among former smokers, experiments confirmed the associations of L1-ORF1p with $FEV_1$, FVC and airflow limitation after further adjustment for active asthma and after restricting analyses to participants with no active asthma. In addition, among former smokers, participants in the highest quartile of L1-ORF1p had mean $FEV_1$ deficits of 18% status in modifying L1-ORF1p effects on lung function and COPD. Because of the modest effect magnitude of some of the associations and the relatively small sample size of some subgroup analyses, replication studies are also warranted to test the generalisability of results. tronger L1-ORF1p associations were identified with $FEV_1$ than FVC, resulting in consistent effects on $FEV_1/FVC$ and risk for airflow limitation, an observation that is in line with the stronger effects of cigarette smoking on airway obstruction than spirometric restriction (see, Guerra S, et al., Thorax 2010; 65:499-504).

In conclusion, the results of these experiments observed higher circulating levels of L1-ORF1p to be associated with lower lung function levels and increased risk for airflow limitation among former smokers.

Example 5

Non-small cell lung cancer (NSCLC) is the most common type of lung cancer and the leading cause of cancer-related mortality and economic burden in the United States (see, Spira, A., B. Halmos, and C. A. Powell, Am J Respir Crit Care Med, 2015. 192 (3): p. 283-94). More than 65% of NSCLC patients show cancer progression presenting with locally advanced or metastatic disease (see, Reck, M., et al., Lancet, 2013. 382 (9893): p. 709-19). Current treatments have relatively low response rates and significant toxicity. Therefore, identification of new targets and drugs is needed to aid in the development of alternative therapeutic options for patients with NSCLC (see, Jonna, S. and D. S. Subramaniam, Discov Med, 2019. 27 (148): p. 167-170).

LINE1s are autonomous and highly mutagenic genetic elements that mobilize throughout the genome via retrotransposition (see, Cordaux, R. and M. A. Batzer, Nat Rev Genet, 2009. 10(10): p. 691-703; de Koning, A. P., et al., PLoS Genet, 2011. 7 (12): p. e1002384). In humans, LINE1 copies constitute 17 to 20% of the genome, though only ~100 LINE1s per individual remain retrotransposition competent due to truncations during the course of reverse transcription and polymorphic variations in LINE1 sequence. LINE1 encodes two proteins: L1-ORF1p, a 40 kDa protein with nucleic acid binding activity, and ORF2p, a 150 kDa protein with endonuclease and reverse transcriptase activities (see, Beck, C. R., et al., Annu Rev Genomics Hum Genet, 2011. 12: p. 187-215). A complete cycle of L1 retrotransposition consists of transcription of L1 RNA, export into the cytoplasm, translation of ORF1 and ORF2, association of L1 RNA with ORF1 and ORF2 proteins to form ribonucleoprotein (RNP) particles, import of RNPs into the nucleus, reverse transcription, and integration into new genomic locations (see, Ostertag, E. M. and H. H. Kazazian, Jr., Annu Rev Genet, 2001. 35: p. 501-38). Active LINE1s are a source of endogenous mutagenesis, with reactivation in somatic cells associated with a variety of genetic alternations including, aberrant splicing, exon skipping, gene fusions, and genome rearrangements that change gene expression and promote genomic instability (see, Beck, C. R., et al., Annu Rev Genomics Hum Genet, 2011. 12: p. 187-215).

The genome of NSCLCs is strongly affected by L1 insertions (see, Iskow, R. C., et al., Cell, 2010. 141 (7): p. 1253-61; Rodic, N., et al., Am J Pathol, 2014. 184 (5): p. 1280-6). As such, systematic investigation of mechanisms responsible for the regulation of LINE1 protein expression and the specific roles of LINE1s in NSCLC progression are crucial to the identification of novel molecular targets for NSCLC therapy.

Nucleolin (NCL) is an RNA-binding protein, and more than 90% of NCL is localized in the nucleolus. However, NCL is also present in other cellular compartments, including the nucleoplasm, cytoplasm, and cell surface. NCL has multiple roles in ribosome biogenesis, transcription, DNA and RNA metabolism, DNA repair, and apoptosis (see, Brockstedt, E., et al., J Biol Chem, 1998. 273 (43): p.

28057-64; Yang, C., D. A. Maiguel, and F. Carrier, Nucleic Acids Res, 2002. 30 (10): p. 2251-60; Abdelmohsen, K. and M. Gorospe, RNA Biol, 2012. 9 (6): p. 799-808; Berger, C. M., X. Gaume, and P. Bouvet, Biochimie, 2015. 113: p. 78-85). In contrast to normal tissue, NCL excessively accumulates in the cytoplasm and the cell surface (extranuclear) of several cancer cell types, including lung cancer cells (see, Chalfin, H. J., et al., Clin Genitourin Cancer, 2017. 15 (3): p. e477-e481; Hammoudi, A., et al., Biochem Biophys Res Commun, 2013. 440 (3): p. 364-70; Pichiorri, F., et al., J Exp Med, 2013. 210 (5): p. 951-68; Xu, J. Y., et al., Tumour Biol, 2016. 37 (8): p. 10349-56). One key function of NCL is the modulation of cellular protein levels by binding mRNA targets to regulate RNA turnover and translation. NCL was recently reported to bind LINE1 RNA (see, Percharde, M., et al., Cell, 2018. 174 (2): p. 391-405 e19), but the functional implications of this interaction are not yet fully understood. Here, we present evidence that NCL modulates LINE1 activity by regulating the expression of L1-ORF1 protein. This interaction can be targeted pharmacologically by NCL antagonists, thus opening the door to novel therapies for lung cancer treatment.

Materials

NucAnt 6L (N6L) was synthesized as previously described and dissolved in 5% D-mannitol (see, Destouches, D., et al., Cancer Res, 2011. 71 (9): p. 3296-305). AS1411 (5'-GGTGGTGGTGGTTGTGGTGGTGGTGG-3' (SEQ ID NO:2)) oligodeoxynucleotide in the desalted form was purchased from Life Technologies (Grand Island, NY). Anti-rabbit IgG and anti-mouse IgG antibodies linked to horseradish peroxidase (HRP), anti-nucleolin monoclonal (MS-3), and anti-GAPDH monoclonal antibody were from Santa Cruz Biotech. A custom made polyclonal anti-human L1-ORF1p antibody was produced by New England Peptide LLC. The antigen peptide "MGKKQNRKTGNSKTQ (SEQ ID NO:1)" sequence used to generate the rabbit polyclonal anti-human L1-ORF1p does not match the murine ORF1p amino acid sequence. Further, the specificity of the antibody against human L1-ORF1p was validated using several criteria including a single band of the expected molecular weight by Western blot, use of positive and negative control cell lines and tissue sources, specific knockdown of signal intensity using siRNAs, and high reproducibility between experimental runs and antibody lots. Biochemical validation of the anti-L1-ORF1p has been described previously (see, Reyes-Reyes, E. M., et al., Oncotarget, 2017. 8 (61): p. 103828-103842).

Cell Cultures and Treatments

Cell lines were purchased from the American Type Culture Collection (ATCC). Cells were grown in a humidified environment at 37° C. with 5% $CO_2$. Cell lines were confirmed to be free of *mycoplasma* contamination (Myco-Alert; Lonza). NSCLC cell lines (NCI-H460, NCI-H520, NCI-H1299, and A549) were grown in RPMI medium supplemented with fetal bovine serum at a concentration of 10%, 62.5 mg/mL penicillin and 100 mg/mL streptomycin (Life Technologies). The human bronchial epithelial cell lines BEAS-2B and BZR were grown in LHC-9 medium (Thermo Fisher Scientific). Verification of all cell line identities was performed by short tandem repeat (STR) sequencing using reference databases from ATCC (Genetics Core, University of Arizona, AZ). Cells were plated 1-day before treatments and challenged with the desired concentrations of N6L or AS1411 as indicated in figure legends. For biochemical analyses, cells were lysed with buffer containing 150 mmol/L NaCl, 2 mmol/L EDTA, 50 mmol/L Tris-HCl, 0.25% deoxycholic acid, 1% IGEPAL CA-630 (pH 7.5), supplemented with protease and phosphatase inhibitor cocktails (EMD Millipore) for 5 min at 4° C., and then cleared by centrifugation at 16,000×g for 10 minutes at 4° C. All protein concentrations were determined using the bicinchoninic acid assay (Thermo Fisher Scientific).

Western Blot Analyses

Total cell lysates were resolved by SDS-polyacrylamide gel electrophoresis and electrotransferred onto polyvinylidene fluoride membranes (Millipore) in Tris-glycine buffer containing 20% methanol. Proteins were detected by immunoblotting. Membranes were stripped of bound antibodies using Restore™ PLUS Western Blot Stripping Buffer (Thermo Fisher Scientific) and reprobed as described in figure legends.

Nucleolin Knockdown Expression

NCL small interfering RNA (siRNA) duplex sequences [5'-GGUCGUCAUACCUCAGAAGtt (SEQ ID NO:3) (NCL #1, ID #144014), 5'-CGGUGAAAUUGAUG-GAAAUtt (SEQ ID NO:4) (NCL #2, ID #144016)] and scrambled siRNA sequences (Silencer Negative Control #1 siRNA (AM4635)) were chemically synthesized and annealed by Life Technologies. BLAST analysis showed no homology to any sequence in the Human Genome Database, other than the intended target. siRNAs were transfected using Lipofectamine_RNAiMAX (Life Technologies), according to manufacturer's directions. Briefly, cells were plated and incubated overnight to allow adherence, then transfected with siRNAs for 8 h. Cell medium was replaced with fresh complete medium, and cells incubated for 72 h before analysis as described in figure legends.

Cell Proliferation

Measurements of cell proliferation were completed using a 3-(4,5-dimethylthiazol-2-yl)-2,5-diphenyltetrazolium bromide (MTT) assay (see, Bates, P. J., et al., Methods Mol Biol, 2009. 542: p. 379-92). This assay detects metabolic activity based on NAD (P) H-dependent cellular oxidoreductase activity and has been used as a reliable measure of cell proliferation in cultured bronchial epithelial cells (see, Reyes-Reyes, E. M., et al., Oncotarget, 2017. 8 (61): p. 103828-103842). Briefly, 3,000 cells were seeded in quadruplicate 96-well plates and allowed to adhere overnight. Cells were treated with different concentrations of N6L and incubated for 72 h without changing the culture medium. The signal corresponding to medium from plates with no cells was subtracted as background. Cell proliferation was determined by normalizing to the proliferation of untreated cells for each cell type.

Measurements of Cell Viability

BEAS-2B and H520 cells (60,000) were plated in 12-well plates one day before treatment. Cultures were either challenged with 10 µM N6L or an equivalent volume of vehicle. Adherent and floating cells were harvested after three days and pelleted by centrifugation. The pellet was resuspended in 0.4% trypan blue/PBS solution and stained cells counted to measure viability.

In Vivo Studies

Healthy male, weanling nude mice (Fox1nu) were purchased from Charles River Laboratories Inc. After acclimation for a week in the animal facility, mice were injected subcutaneously with a single cell suspension consisting of $3 \times 10^6$ NCI-H520 cells in 200 µL PBS into each flank. When subcutaneous tumors reached a volume of approximately 100 mm³, the mice were randomized into two groups of 6 mice per group. The control group was given PBS and compared to animals given 10 mg/kg/day N6L dissolved in PBS three times per week by intraperitoneal injection. Tumor volume and body weights were recorded every two or three days for 16 days. Tumors were resected following euthanasia and processed for detection of L1-ORF1p expression by immunoblotting.

Statistical Analysis

Experimental replicates were independent and performed on separate days. Comparisons between treated and control groups were carried out using multiple paired two-tailed t-tests or ANOVA followed by Tukey's multiple comparisons test as specified in figure legends. Statistical significance was denoted by p-values less than 0.05.

Results

NCL Regulates Expression of LINE1

Previous reports indicate that 50% of NSCLC have increased L1-ORF1p expression across a panel of different human lung neoplasms (see, Rodic, N., et al., Am J Pathol, 2014. 184(5): p. 1280-6). It has been reported that stable ectopic overexpression of LINE1 in non-malignant human bronchial epithelial BEAS-2B cells induces oncogenic transformation and tumorigenesis in vivo, independent of its reverse transcriptase activity and active cycles of retrotransposition (see, Reyes-Reyes, E. M., et al., Oncotarget, 2017. 8 (61): p. 103828-103842; Reyes-Reyes, E. M., et al., Am J Cancer Res, 2016. 6 (5): p. 1066-77). These findings indicate that LINE1 is involved in lung carcinogenesis and possibly serve as a novel candidate for targeted therapeutics during malignant progression of NSCLCs.

Figure 12:
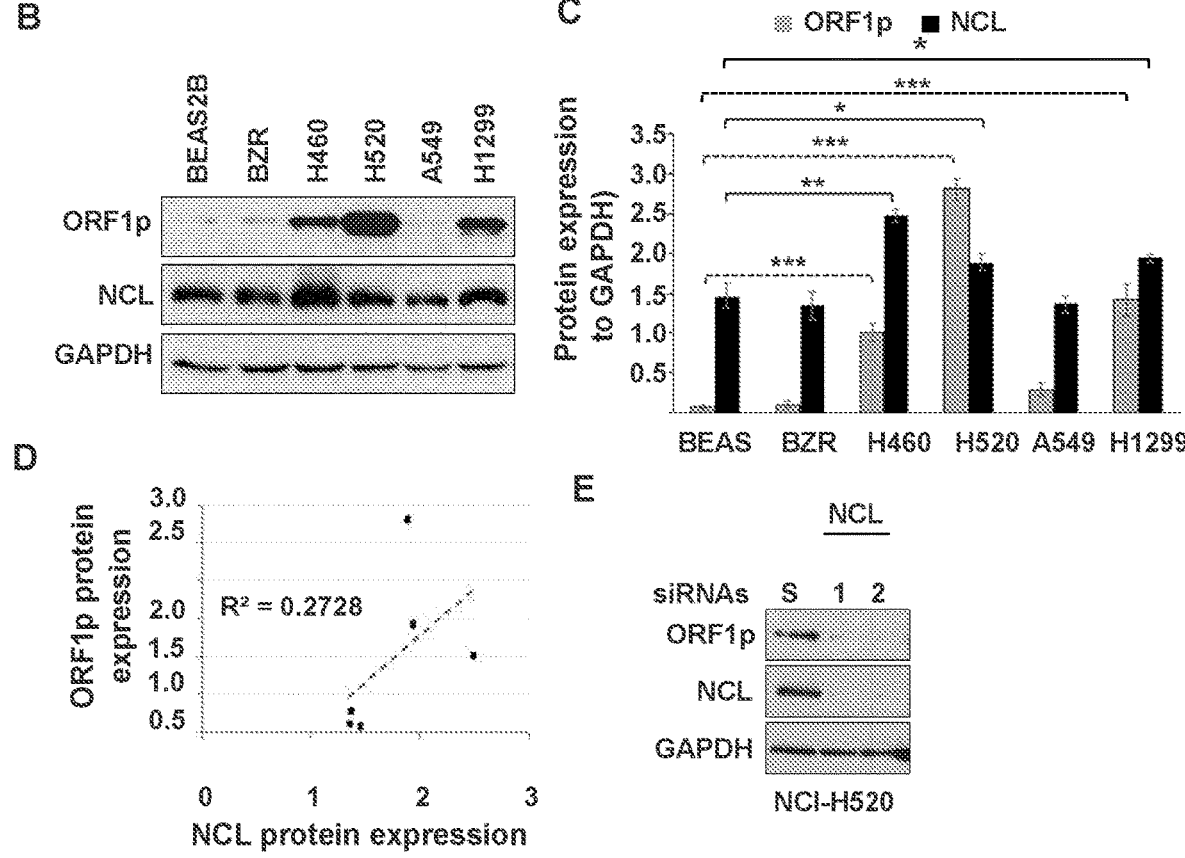
FIG. 12: A) Phenotypic profiles of lung cells employed in this study. B) Whole-cell extracts from BEAS-2B, BZR, NCI-H460, NCI-H520, A549, or NCI-H1299 were examined by immunoblotting using L1-ORF1p, NCL, and GAPDH antibodies. C) NCL, L1-ORF1p, and GAPDH were quantified by densitometry. Relative protein expression was expressed as NCL/GAPDH and L1-ORF1p/GAPDH ratios from three independent analyses. Error bars represent SEM. Statistical significance was determined using multiple paired two-tailed t-tests; n=3; *p<0.05; p<0.001, p<0.0001. D) Correlation between L1-ORF1p and NCL protein levels. E) NCI-H520 cells were transfected with two different NCL siRNAs (NCL #1 and 2). Three days post-transfection, cells were analyzed for expression of L1-ORF1p, NCL, and GAPDH.

NCL modulates cellular protein levels by binding mRNA targets to control RNA turnover and translation. This protein is of interest given its ability to regulate cancer cell phenotypes and to partner with LINE1 RNA (see, Percharde, M., et al., Cell, 2018. 174 (2): p. 391-405 e19). Therefore, studies were conducted to determine whether NCL modulates L1-ORF1p expression in NSCLC. We first examined the relative expression of L1-ORF1p and NCL in four NSCLC cell lines (NCI-H460, NCI-H520, NCI-H1299, and A549), compared to the non-malignant BEAS-2B cell line and its ras-transformed counterpart, BZR cells (FIG. 12A). Immunoblotting analysis showed that L1-ORF1p was strongly expressed constitutively in three NSCLC cell lines (NCI-H520>NCI-H1299>NCI-H460), while relative L1-ORF1p expression was detectable at low levels in BEAS-2B, BZR, and A549 cells (FIGS. 12B and C). All tested cell lines showed strong expression of NCL (FIGS. 12B and C). While the expression of L1-ORF1p did not consistently correlate with NCL expression (FIG. 12D), higher levels of NCL expression were preferentially observed in NSCLC cell lines with higher LINE1-ORFp1 expression (FIG. 12C).

Next, whether NCL played a role in the regulation of LINE1 by examining the effect of genetic knocking down of NCL on L1-ORF1p expression in NCI-H520 cells was examined. Immunoblot analyses confirmed that NCL expression could be reduced by >90% in cells transfected with two distinct NCL siRNAs compared with cells transfected with scrambled siRNA (FIG. 12D). Knockdown of NCL elicited a dramatic decrease in L1-ORF1p expression (FIG. 12E). These results indicate NCL is a positive regulator of L1-ORF1p expression.

N6L, a NCL Antagonist, Inhibits L1-ORF1p Expression

Figure 13:
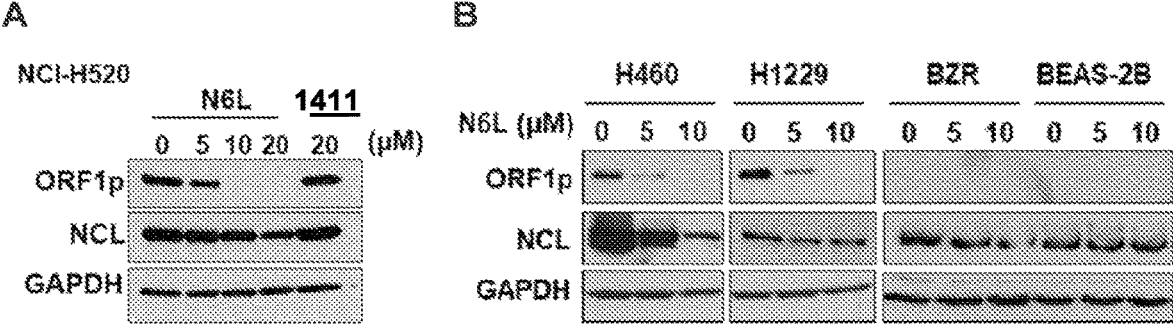
FIG. 13: A) NCI-H520 cells were treated with vehicle (5% D-mannitol solution) or different concentration of N6L or 20 μM AS1411 (AS) for 48 h. B) NCI-H460, NCI-H1299, BZR, and BEAS-2B cells were treated with different concentration of N6L for 48 h. Whole-cell lysates were analyzed by immunoblotting using L1-ORF1p, NCL, and GAPDH antibodies.

To further evaluate the influence of NCL on L1-ORF1p expression, the next set of experiments was designed to determine if pharmacological agents that block NCL functions modulate expression of L1-ORF1p in NSCLC cells. Currently, N6L, a pseudopeptide, and AS141, a DNA aptamer, are the best options to study the biological functions of NCL. We analyzed L1-ORF1p expression profiles in NSCLC cells challenged with various concentrations of N6L and AS1411. N6L completely inhibited L1-ORF1p protein expression in NCI-H520, NCI-H460, and NCI-H1229 cells treated with 10 μM for 24 h (FIGS. 13A and B). In contrast, AS1411 was without effect in any of the cell lines (data not shown) or in NCI-H520 cells at high concentrations (20 μM) (FIG. 13A). Because LINE1 can be reactivated under stress conditions, the effects of N6L in low expressing BEAS-2b and BZR cells. N6L was without effect in these lines were tested. These data indicate that L1-ORF1p expression is blocked by the NCL antagonist N6L and suggest that NCL may be a reasonable pharmacological target to inhibit LINE1-mediated progression of NSCLCs.

N6L Activity Correlates with L1-ORF1p Expression

Figure 14:
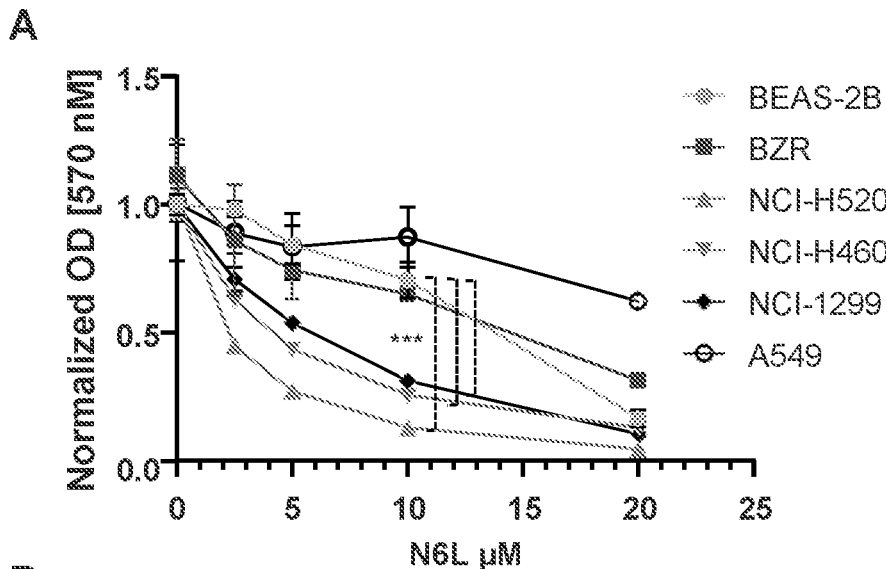
FIG. 14: A) Lung cells were treated with vehicle (5% D-mannitol solution) or various concentrations of N6L for 3 days. The MTT assay was used to measure cell proliferation.
Figure 14:
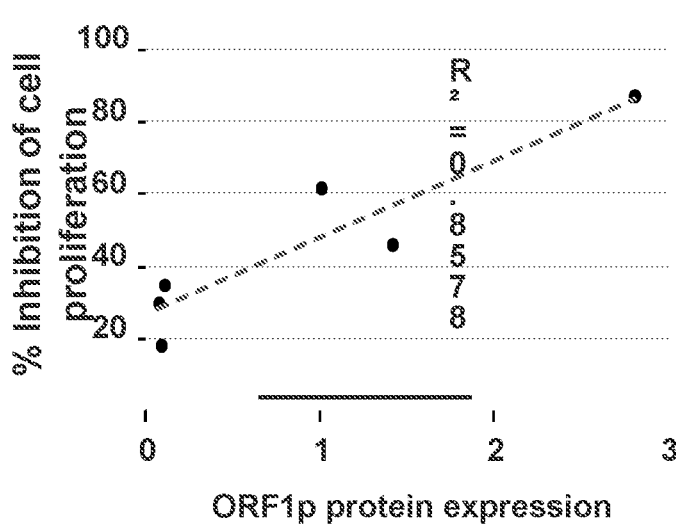

N6L has potent growth inhibitory effects in several cell lines or primary cells derived from brain, breast, prostate, T lymphocytes, colon, pancreas, skin, and kidney carcinomas (see, De Cola, A., et al., Cancer Lett, 2018. 412: p. 272-282; Destouches, D., et al., J Biol Chem, 2012. 287 (52): p. 43685-93; Gilles, M. E., et al., Cancer Res, 2016. 76 (24): p. 7181-7193). However, the effect of N6L on NSCLC cell growth has not being examined. Using the MTT assay as an indirect measure of cell proliferation we found that N6L preferentially inhibited NSCLC lines with the highest constitutive expression of L1-ORF1p (NCI-H520>NCI-H460>NCI-H1299) compared to lines with lower expression (BEAS-2B, BZR and A549 cell lines) (FIGS. 14A and B). N6L (10 μM) did not increase Trypan blue uptake in BEAS-2B or NCI-H520 cells after treatment for three days, indicating that NCL inhibition is associated with cytostatic effects, in the absence of cytotoxicity. Moreover, the anti-proliferative activity of N6L correlated with the relative abundance of L1-ORF1p protein (FIG. 14C). These results suggest that the pharmacological effectiveness of N6L involves interference with L1-ORF1p expression.

N6L Inhibits L1-ORF1p Expression In Vivo

Given the inherent limitations of in vitro models, experiments next set out to determine whether the pharmacological efficacy of N6L was observed in vivo. To this end, nude mice with subcutaneous NCI-H520 xenografts received intraperitoneal injections of 250 μg of N6L in 200 μL PBS per day three times a week for two consecutive weeks to approximate a cumulative dose of 10 mg/kg/day. Additional control groups received an equivalent amount of vehicle alone. Tumor volumes and body weights were recorded at regular intervals. FIG. 15A shows that N6L significantly inhibited tumor growth in the nude mouse xenograft model. No evidence of toxicity was observed for any of the treatments, as evidenced by the absence of changes in body weight (FIG. 15B), animal behavior, or organ examination at necropsy. Further, immunoblotting analysis showed that tumors from mice treated with N6L exhibited lower expression of L1-ORF1p compared to tumors from vehicle treated mice (FIG. 16C). These data indicate that the NCL antagonist N6L blocks LINE1 activity and tumor growth in vivo.

Discussion

These experiments indicate that NCL positively regulates the expression of L1-ORF1p in NSCLC cell lines and that NCL may be targeted pharmacologically by N6L to regulate the oncogenic activity of LINE1 in NSCLC cell lines. L1-ORF1p is expressed constitutively in NSCLC tumors but not in healthy tissues (see, Iskow, R. C., et al., Cell, 2010. 141 (7): p. 1253-61; Rodic, N., et al., Am J Pathol, 2014. 184 (5): p. 1280-6). In keeping with previous reports, it was observed that L1-ORF1p was barely detected in non-malignant human bronchial epithelium cells BEAS-2B, but significantly increased under constituve conditions in the human NSCLS tumor cell lines, H460, H520, and H1299. Interestingly, the H460, H520, and H1299 cell lines also expressed higher levels of NCL than the non-malignant human bronchial epithelium cells BEAS-2B. NCL also increases murine L1-ORF2 expression by binding to its RNA in the internal ribosome entry site (IRES) to facilitate translation (see, Peddigari, S., et al., Nucleic Acids Res, 2013. 41 (1): p. 575-85). Consequently, NCL depletion decreases mouse L1 retrotransposition activity in vitro [26]. These findings support the conclusion that NCL can regulate oncogenic activity by influencing the expression and relative abundance of LINE1 proteins.

NCL plays significant roles in many physiological processes such as cellular proliferation, survival, and apoptosis (see, Jia, W., et al., Life Sci, 2017. 186: p. 1-10). Disruption of NCL homeostatic functions impairs cancer progression by altering signaling pathways through genetic and epigenetic mechanisms that control proliferation, survival, and metastasis of cancer cells (see, Berger, C. M., X. Gaume, and P. Bouvet, Biochimie, 2015. 113: p. 78-85). Recently, NCL was shown to form a complex with LINE1 RNA and KAPI (a transcriptional co-repressor). This complex promotes the self-renewal of embryonic stem cells by suppressing Dux expression, a master activator of the developmental transition program in two-cell embryos (see, Percharde, M., et al., Cell, 2018. 174 (2): p. 391-405 e19). Thus, NCL may induce cancer progression by promoting cancer cell stemness via LINE1 RNA. Our previous findings showed that overexpression of LINE1 in non-malignant human bronchial epithelium cells induces oncogenic transformation and tumorigenesis in vivo (see, Reyes-Reyes, E. M., et al., Am J Cancer Res, 2016. 6 (5): p. 1066-77). These present findings showing that NCL regulates L1-ORF1p expression suggests that dysregulation of NCL functions may promote lung carcinogenesis via LINE1 activation.

N6L is a pseudopeptide that functions as a NCL antagonist through selective binding to NCL to inhibit tumor growth and angiogenesis (see, Destouches, D., et al., Cancer Res, 2011. 71 (9): p. 3296-305; De Cola, A., et al., Cancer Lett, 2018. 412: p. 272-282; Gilles, M. E., et al., Cancer Res, 2016. 76 (24): p. 7181-7193; Dhez, A. C., et al., J Cell Physiol, 2018. 233 (5): p. 4091-4105; Diamantopoulou, Z., et al., Oncotarget, 2017. 8 (52): p. 90108-90122). N6L blocks survival signaling pathways, slows down cell cycle progression, induces autophagy, and inhibits tumor cell invasion (see, Destouches, D., et al., J Biol Chem, 2012. 287 (52): p. 43685-93; Gilles, M. E., et al., Cancer Res, 2016. 76 (24): p. 7181-7193; Benedetti, E., et al., Oncotarget, 2015. 6 (39): p. 42091-104; Jain, N., et al., Leukemia, 2018. 32 (3): p. 663-674). Given that LINE1 increases cancer cell proliferation and tumorigenesis (see, Reyes-Reyes, E. M., et al., Oncotarget, 2017. 8 (61): p. 103828-103842; Zhang, R., et al., Cancer Res, 2019), the ability of N6L to decrease L1-ORF1p expression in NSCLC cell lines and in vivo is consistent with observed impairments of NSCLC xenograft tumor growth. We conclude that the impact of N6L on tumor growth involves decreases in L1-ORF1p which in turn influence LINE1 oncogenic functions.

The finding that N6L, but not AS1411, blocked L1-ORF1p expression suggests that LINE1 interference by these agents is exerted via different mechanisms. N6L specifically binds to cell surface NCL to promote internalization through an endocytic mechanism. After internalization, N6L can be localized in the cytoplasm, nucleoplasm, and nucleolus (see, Destouches, D., et al., Cancer Res, 2011. 71 (9): p. 3296-305), and is known to target both the nuclear and extranuclear functions of NCL (see, De Cola, A., et al., Cancer Lett, 2018. 412: p. 272-282; Destouches, D., et al., J Biol Chem, 2012. 287 (52): p. 43685-93; Benedetti, E., et al., Oncotarget, 2015. 6 (39): p. 42091-104; Birmpas, C., et al., BMC Cell Biol, 2012. 13: p. 32). In contrast, AS1411 is a DNA aptamer that mainly internalizes into cells through the gulp of large vesicles using the micropinocytosis endocytic mechanism. Internalized AS1411 is localized only to the cytoplasm and never localizes to the nuclei of viable cells (see, Reyes-Reyes, E. M., et al., Cancer Res, 2010. 70 (21): p. 8617-29). Thus, AS1411 only targets NCL extranuclear functions such as shuttling, signal transduction, or mRNA stability, which could also affect protein expression (see, Bates, P. J., et al., Biochim Biophys Acta Gen Subj, 2017. 1861 (5 Pt B): p. 1414-1428). The observation that AS1411 did not affect L1-ORF1p expression suggests that nuclear functions of NCL are the ones involved in regulation of L1-ORF1p expression. It has been suggested that the antiproliferative activity of AS1411 is not specific for nucleolin targeting (see, Kabirian-Dehkordi, S., et al., Nanomedicine, 2019: p. 102060). Thus, it is possible that AS1411 does not target key extranuclear functions of NCL linked to L1-ORF1p expression.

In summary, the ability of N6L to block the expression of L1-ORF1p suggests that LINE1 activity during NSCLC progression may be effectively regulated by pharmacological agents and emenable to precision therapeutics. N6L has already being tested in human clinical trials in other cancers, and clinical development efforts are ongoing. Therefore, it would be interesting to test whether N6L may be an effective therapeutic agent for NSCLC and whether the L1-ORF1p expression may serve as a biomarker to select patients for future N6L treatment.

Example 6

This example further demonstrates that cells export cellular LINE-1 mRNA and protein in extracellular vesicles and this cargo can be used as a biomarker of disease.

H460 lung epithelial cells were exposed to 1 uM benzo [a]pyrene (BaP) for 2 days before collection of culture media.

EV isolation: Media were centrifuged at 500×g for 5 min to remove cells and concentrated using a 100 kDa MWCO Amicon filter. Samples were then centrifuged at 25,000×g for 30 min to pellet apoptotic vesicles and cellular debris followed by ultracentrifugation at 100,000×g for 2 h. The EV pellet was washed in PBS and either re-centrifuged at 100,000×g or loaded onto an iodixanol gradient.

Iodixanol gradient: The exosome pellet was placed at the bottom of iodixanol gradient and centrifuged at 100,00×g for 18 h. Twelve one mL fractions were removed, diluted in 10 mL PBS, and EVs pelleted at 100,000×g for 2 h. Pellets were resuspended in PBS and used for RNA isolation or RIPA protein extraction.

Total RNA was harvested (Zymo) and subjected to post-elution DNAse digestion. A cDNA was created using oligo d (T) primers. Gene expression analysis was performed via qPCR using probe-based detection. Expression was expressed as a fold change from the EV-free medium (EFM).

Protein was extracted using RIPA buffer. 10 kDa MWCO centrifuge filters were used for buffer exchange to perform RNAseA treatment and cysteine capping via N-ethylmaleimide (NEM), where indicated.

Iodixanol buoyant density gradient ultracentrifugation demonstrated the presence of LINE-1 in extracellular vesicles (see, FIG. 16).

Extracellular vesicles were shown to be enriched with LINE-1 ORF1p multimers and LINE-1 ribonucleoproteins. FIG. 17 shows LINE-1 ORF1 protein form multimers that bind LINE-1 mRNA and ORF2p to create a ribonucleoprotein used for retrotransposition. Initial EV ORF1 Western blots suggested the presence of a large ORF1p polymer unique to EVs that could not enter the stacking phase (FIG. 18A). Detection of EV ORF1p by SDS-PAGE was shown to be maximized by RNAseA and cysteine capping (NEM) (FIG. 18B). The effects of antibody choice and treatment with β-ME, RNAseA, and cysteine capping (NEM) on ORF1 detection are shown in FIG. 18C.

LINE-1 mRNA levels in EVs were shown to be proportional to cellular levels across six cell lines (see, FIG. 19A), and Bap-mediated increases in cellular LINE-1 levels were mirrored within EVs (see, FIGS. 19B and 19C).

Example 7

Tp53 mutant lung cancer samples (5 male and S female) were provided by the tissue acquisition and cellular/molecular analysis shared resource (tacmasr) of the ua cancer center. Formalin-fixed paraffin-embedded tissues from 5 male and 5 female lung cancers were processed for immunihistochemical detection of orf-1p using a custom-made antibody polyclonal antibody. Five different fields were examined per subject for a total of 50 assessments. Digital photomicrographs were acquired and analyzed with commercial image software to quantify signals. Statistical analysis revealed major differences in orf-1p expression, with females showing markedly increased signal intensities compared to males (see FIG. 20).

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

INCORPORATION BY REFERENCE

The entire disclosure of each of the patent documents and scientific articles referred to herein is incorporated by reference for all purposes.

What is claimed is:

1. A method for treating a human subject having lung cancer, comprising
   (a) obtaining a blood sample from a human subject, wherein the human subject has lung cancer,
   (b) obtaining lung cancer cell exosomes from the blood sample,
   (c) assaying the lung cancer exosomes to detect an increased level of LINE-1 ORF1 polypeptide relative to LINE-1 ORF1 polypeptide levels in non-cancerous lung cell exosomes, and
   (d) administering a nucleolin antagonist to the human subject having an increased level of LINE-1 ORF1 polypeptide in the lung cancer cell exosomes relative to the non-cancerous lung cell exosomes, wherein the nucleolin antagonist is N6L.

2. A method for treating lung cancer in a human subject, wherein the method comprises administering to a subject having lung cancer a pharmaceutical composition comprising a nucleolin antagonist, wherein the nucleolin antagonist is N6L, wherein the human subject having lung cancer has an increased level of LINE-1 ORF1 polypeptide in lung cancer cell exosomes obtained from the human subject relative to LINE-1 ORF1 polypeptide levels in non-cancerous lung cell exosomes.

3. The method of claim 1,
   wherein the assaying comprises detecting LINE-1 ORF1 polypeptide in the exosomes by Western blot or immunoelectron microscopy.

4. The method of claim 1, wherein the nucleolin antagonist N6L is administered intraperitoneally at a dosage of about 10 mg/kg/day.

* * * * *